US008198258B2

(12) United States Patent
Mor et al.

(10) Patent No.: US 8,198,258 B2
(45) Date of Patent: Jun. 12, 2012

(54) OLIGORIBONUCLEOTIDES AND METHODS OF USE THEREOF FOR TREATMENT OF FIBROTIC CONDITIONS AND OTHER DISEASES

(75) Inventors: Orna Mor, Kiryat Ono (IL); Elena Feinstein, Rehovot (IL)

(73) Assignee: Quark Pharmaceuticals Inc., Fremont, CA (US)

( * ) Notice: Subject to any disclaimer, the term of this patent is extended or adjusted under 35 U.S.C. 154(b) by 0 days.

(21) Appl. No.: 13/092,501

(22) Filed: Apr. 22, 2011

(65) Prior Publication Data

US 2011/0201670 A1  Aug. 18, 2011

Related U.S. Application Data

(60) Division of application No. 12/072,941, filed on Feb. 28, 2008, now Pat. No. 7,939,652, which is a continuation of application No. 11/045,780, filed on Jan. 27, 2005, now abandoned.

(60) Provisional application No. 60/540,687, filed on Jan. 30, 2004, provisional application No. 60/641,522, filed on Jan. 4, 2005.

(51) Int. Cl.
- *A61K 31/70* (2006.01)
- *C07H 21/02* (2006.01)
- *C07H 21/04* (2006.01)
- *C12Q 1/68* (2006.01)

(52) U.S. Cl. ...... 514/44 A; 435/375; 435/377; 536/23.1; 536/24.1; 536/24.5

(58) Field of Classification Search ............ None
See application file for complete search history.

(56) References Cited

U.S. PATENT DOCUMENTS

| | | | |
|---|---|---|---|
| 6,506,559 B1 | 1/2003 | Fire et al. | |
| 6,773,916 B1 | 8/2004 | Thiel et al. | |
| 7,452,987 B2 | 11/2008 | Giese et al. | |
| 2003/0143732 A1 | 7/2003 | Fosnaugh et al. | |
| 2004/0259247 A1 | 12/2004 | Tuschl et al. | |
| 2005/0197310 A1 | 9/2005 | Mor et al. | |
| 2007/0021360 A1 | 1/2007 | Nyce et al. | |

FOREIGN PATENT DOCUMENTS

| | | |
|---|---|---|
| EP | 1144623 B1 | 10/2001 |
| GB | 2 397 818 B | 3/2005 |
| WO | WO 98/04245 | 2/1998 |
| WO | WO 2000/024885 A2 | 5/2000 |
| WO | WO 2000/024885 A3 | 5/2000 |
| WO | WO 02/44321 A2 | 6/2002 |
| WO | WO 02/44321 A3 | 6/2002 |
| WO | WO 02/85308 | 10/2002 |
| WO | WO 02/85309 A2 | 10/2002 |
| WO | WO 03/70197 A2 | 8/2003 |
| WO | WO 03/70197 A3 | 8/2003 |
| WO | WO 2004/009769 A2 | 1/2004 |
| WO | WO 2004/113496 A2 | 12/2004 |
| WO | WO 2004/113496 A3 | 12/2004 |

OTHER PUBLICATIONS

European Extended Search Report and Opinion issued on Jul. 18, 2011 in connection with European Patent Application No. 10179637.3 filed Jan. 27, 2005.

Bernstein, E. et al. (2001) "Role for a Bidentate Ribonuclease in the Initiation Step of RNA Interference" *Nature* 409:363-366.

Bartel, P. D. (2004) "MicroRNAs: Genomics, Biogenesis, Mechanism, and Function" *Cell* 116:281-297.

Chalk, M. A. et al. (2004) "Improved and Automated Prediction of Effective siRNA" *Biochemical and Biophysical Research Communication* 319:264-274.

Chen, J.S.K. et al. (1999) "Tissue Transglutaminase: An Enzyme with a Split Personality" *Int. Jour. of Biochem. & Cell Biology* 31:817-836.

Citron, B.A. et al. (2002) "Protein Crosslinking, Tissue Transglutaminase, Alternative Splicing and Neurodegeneration" *Neurochemistry International* 40:69-78.

Dieterich, W. et al. (1997) "Identification of Tissue Transglutaminase as the Autoantigen of Celiac Disease" *Nature Medicine* 3(7):797-801.

Elbashir, S.M. et al (2001) "Duplexes of 21-Nucleotides RNAs Mediate RNA Interference in Cultured Mammalian Cells" *Nature* 411:494-498.

Elbashir SM, et al. (2001) Functional anatomy of siRNAs for mediating efficient RNAi in *Drosophila melanogaster* embryo lysate. *EMBO J.* 20(23):6877-6888.

Fire, A. et al. (1998) "Potent and Specific Genetic Interference by Double-Stranded RNA in *Caenorhabditis elegans*" *Nature* 391:806-811.

Fraij BM, et al. (1992) A retinoic acid-inducible mRNA from human erythroleukemia cells encodes a novel tissue transglutaminase homologue. *J. Biol. Chem.* 267(31):22616-22623.

Greenberg, B. (2001) "Treatment of Heart Failure: State of the Art and Prospective" *Journal of Cardiovascular Pharmacology* 38:S59-S63.

(Continued)

*Primary Examiner* — Sean McGarry
(74) *Attorney, Agent, or Firm* — John P. White; Cooper & Dunham LLP

(57) ABSTRACT

The invention relates to a double-stranded compound, preferably an oligoribonucleotide (siRNA), which down-regulates the expression of a human TGaseII gene at the post-transcriptional level. The invention also relates to a pharmaceutical composition comprising the compound, or a vector capable of expressing the oligoribonucleotide compound, and a pharmaceutically acceptable carrier. The present invention also contemplates a method of treating a patient suffering from a fibrotic disease such as pulmonary, kidney and liver fibrosis or ocular, scarring comprising administering to the patient the pharmaceutical composition in a therapeutically effective dose so as to thereby treat the patient. The invention also relates to treatment of fibrotic and other diseases by use of antibodies to TGaseII polypeptide.

20 Claims, 3 Drawing Sheets

OTHER PUBLICATIONS

Grenard, P. (2001) "Transglutaminase-Mediated Cross-Linking is Involved in the Stabilization of Extracellular Matrix in Human Liver Fibrosis" *Journal of Hepatology* 35:367-375.

Griffin, M. et al. (1979) "Chances in Transglutaminase Activity in an Experimental Model of Pulmonary Fibrosis Induced by Paraquat" *Br. J. Exp. Path.* 60:653-661.

Hwang, K.C. et al. (1996) "α1-Adrenergic Receptor Coupling With $G_h$ in the Failing Human Heart" *American heart Association, Inc.* 94:718-726.

Hannon, G. J. (2002) "RNA Interference" *Nature* 418:244-251.

Johnson, T.S. et al. (1997) "The Role of Transglutaminase in the Rat Subtotal Nephrectomy Model of Renal Fibrosis" *J. Clin. Invest.* 99(12):2950-2960.

Johnson, T.S. et al. (1999) "Transglutaminase Transcription and Antigen Translocation in Experimental Renal Scarring" *J. Am. Soc. Nephrol.* 10:2146-2157.

Karpuj, M.V. et al. (2002) "Prolonged Survival and Decreased Abnormal Movements in Transgenic Model of Huntington Disease, with Administration of the Transglutaminase Inhibitor Cystamine" *Nature Medicine* 8(2):143-149.

Lesort, M. et al. (2000) "Tissue Transglutaminase: A Possible Role in Neurodegenerative Diseases" *Progress in Neurobiology* 61:439-463.

Levenkova, N. et al. (2004) "Gene Specific siRNA Selector" *Bioinformatics* 20(3):430-432.

McManus, T. M. (2002) "Gene Silencing in Mammals by Small Interfering RNAs" *Nature Reviews* 3:737-747.

Mirza, A. et al. (1997) "A Role for Tissue Transglutaminase in Hepatic Injury and Fibrogenesis, and its Regulation by NF-kB" *The American Physiological Society* 281-288.

Piacentini, M. et al. (2002) "Transglutaminase Overexpression Sensitizes Neuronal Cell Lines to Apoptosis by Increasing Mitochondrial Membrane Potential and Cellular Oxidative Stress" *Journal of Neurochemistry* 81:1061-1072.

Reich, S.J., et al. "Small Interfering RNA (siRNA) Targeting *VEGF* Effectively Inhibits Ocular Neuvascularization in a Mouse Model" *Molecular Vision* 9:210-216.

Shin, D. M. et al. (2004) "Cell Type-Specific Activation of Intracellular Transglutaminase 2 by Oxidative Stress or ultraviolet Irradiation" *The Journal of Biological Chemistry* 279(15):15032-15039.

Shridas, P. et al. (2001) "Transglutaminase-Mediated Cross-Linking of α-Crystallin: Structural and Functional Consequences"*FEBS Letters* 499:245-250.

Sioud, M. et al. "Potential Design Rules and Enzymatic Synthesis of siRNAs" *Methods in Molecular Biology* 252:457-468, 2004.

Soutschek, J. et al. (2004) "Therapeutic Silencing of an Endogeneous Gene by Systemic Administration of Modified siRNAs" *Nature* 432:173-178.

Takeuchi, N. et al (2000) "Crystallin Proteins in Lenses of Hereditary Cataractous Rat, ICR/f" *Biol. Pharm. Bull.* 23(3):283-290.

Tolentino, M.J. (2004) "Intravitreal Injection of Vascular Endothelial Growth Factor Small Interfering RNA Inhibits Growth and Leakage in a Nonhuman Primate, Laser—Induced Model of Choroidal Neuvascularization" *Retina, The Journal of Retinal and Vitreous Disease* 24(1):132-138.

Ui-Tei K. et al. (2004) "Guidelines for the Selection of Highly Effective siRNA Sequences for Mammalian and Chick RNA Interference" *Nucleic Acids Research* 32(3):936-948.

Wan, X.H., et al. (2002) "Enhanced Expression of Transglutaminase 2 in Anterior Polar Cataracts and its Induction by TGB-β*in vitro*" *British Journal of Opthalmology* 86:1293-1298.

Zhang, Z. et al. (2003) "COX-2-Dependent Cardiac Failure in Gh/tTG Transgenic Mice" *Circulation Research* 92:1153-1161.

International Search Report issued by the International Searching Authority (ISA/US) on May 18, 2007 in connection with International Application No. PCT/IL05/00102.

Written Opinion of the International Searching Authority (ISA/US) issued on May 18, 2007 in connection with International Application No. PCT/IL05/00102.

International Preliminary Report on Patentability issued by the International Bureau of WIPO on Jun. 19, 2007 in connection with International Application No. PCT/IL05/00102.

U.S. Appl. No. 11/045,780, claims at time of abandonment Mar. 3, 2008.

Fesus L, et al. (2002) "Transglutaminase 2: an enigmatic enzyme with diverse functions," *Trends in Biochem. Sci.*; 27(10):534-539.

Mastroberardino PG, et al., (2002) "'Tissue' transglutaminase ablation reduces neuronal death and prolongs survival in a mouse model of Huntington's disease," *Cell Death and Differentiation*, 9(9):873-880.

Zhu J, et al., (1999) "Rapamycin inhibits hepatic stellate cell proliferation in vitro and limits fibrogenesis in an in vivo model of liver fibrosis," *Gastroenterology*, 5:1198-1204.

Supplementary European Search Report issued by the European Patent Office on Jan. 22, 2008 in connection with European Application No. 05703145.2-2405.

Vickers et al., (2003) "Efficient Reduction of Target RNAs by Small Interfering RNA and RNase H-dependent Antisense Agents," *The Journal of Biological Chemistry*, 278(9):7108-7118.

Edited by Beers et al., (1999), "The Merck Manual of Diagnosis and Therapy", 17 ed. Merck Research Laboratories, Whitehouse Station, NJ, Chapter 222, pp. 1845-1847.

Examination Report issued by the European Patent Office on Jun. 2, 2008 in connection with European Application No. 05703145.2.

Examination Report issued by the European Patent Office on Feb. 26, 2009 in connection with European Application No. 05703145.2.

Communication pursuant to Rule 71(3) EPC issued by the European Patent Office on Jun. 2, 2010 in connection with European Patent Application No. 05703145.2.

Response to the Communication Under Rule 71(3) EPC and Request for Amendments pursuant to Rule 71(4) EPC submitted Sep. 7, 2010 in connection with European Patent Application No. 05703145.2.

Office Action issued Sep. 17, 2009 in connection with U.S. Appl. No. 12/072,941, filed Feb. 28, 2008.

Office Action issued Apr. 19, 2010 in connection with U.S. Appl. No. 12/072,941, filed Feb. 28, 2008.

FIGURE 1.

```
ATGGCCGAGG AGCTGGTCTT AGAGAGGTGT GATCTGGAGC TGGAGACCAA TGGCCGAGAC CACCACACGG  70
CCGACCTGTG CCGGGAGAAG CTGGTGGTGC GACGGGGCCA GCCCTTCTGG CTGACCCTGC ACTTTGAGGG  140
CCGCAACTAC GAGGCCAGTG TAGACAGTCT CACCTTCAGT GTCGTGACCG GCCCAGCCCC TAGCCAGGAG  210
GCCGGGACCA AGGCCCGTTT CCACTAAGA GATGCTGTGG AGGAGGGTGA CTGGACAGCC ACCGTGGTGG  280
ACCAGCAAGA CTGCACCCTC TCGCTGCAGC TCACCACCCC GGCCAACGCC CCATCGGCC TGTATCGCCT  350
CAGCCTGGAG GCCTCCACTG GCTACCAGGG ATCCAGCTTT GTGCTGGGCC ACTTCATTTT GCTCTTCAAC  420
GCCTGGTGCC CAGCGGATGC TGTGTACCTG GACTCGGAAG AGGAGCGGCA GGAGTATGTC CTCACCCAGC  490
AGGGCTTTAT CTACCAGGGC TCGGCCAAGT TCATCAAGAA CATACCTTGG AATTTTGGGC AGTTTGAAGA  560
TGGGATCCTA GACATCTGCC TGATCCTTCT AGATGTCAAC CCCAAGTTCC TGAAGAACGC CGGCCGTGAC  630
TGCTCCCGCC GCAGCAGCCC CGTCTACGTG GGCCGGGTGG TGAGTGGCAT GGTCAACTGC AACGATGACC  700
AGGGTGTGCT GCTGGGACGC TGGACAACA ACTACGGGGA CGGCGTCAGC CCCATGTCCT GGATCGGCAG  770
CGTGGACATC CTGCGGCGCT GGAAGAACCA CGGCTGCCAG CGCGTCAAGT ATGGCCAGTG CTGGGTCTTC  840
GCCGCCGTGG CCTGCACAGT GCTGAGGTGC CTGGGCATCC CTACCCGCGT CGTGACCAAC TACAACTCGG  910
CCCATGACCA GAACAGCAAC CTTCTCATCG AGTACTTCCG CAATGAGTTT GGGGAGATCC AGGGTGACAA  980
GAGCGAGATG ATCTGGAACT TCCACTGCTG GGTGGAGTCG TGGATGACCA GGCCGGACCT GCAGCCGGGG  1050
TACGAGGGCT GGCAGGCCCT GGACCCAACG CCCCAGGAGA AGAGCGAAGG GACGTACTGC TGTGGCCCAG  1120
TTCCAGTTCG TGCCATCAAG GAGGGCGACC TGAGCACCAA GTACGATGCG CCCTTTGTCT TTGCGGAGGT  1190
CAATGCCGAC GTGGTAGACT GGATCCAGCA GGACGATGGG TCTGTGCACA AATCCATCAA CCGTTCCCTG  1260
ATCGTTGGGC TGAAGATCAG CACTAAGAGC GTGGGCCGAG ACGAGCGGGA GGATATCACC CACACCTACA  1330
AATACCCAGA GGGGTCCTCA GAGGAGAGGG AGGCCTTCAC AAGGGCGAAC CACCTGAACA AACTGGCCGA  1400
GAAGGAGGAG ACAGGGATGG CCATGCGGAT CCGTGTGGGC CAGAGCATGA ACATGGGCAG TGACTTTGAC  1470
GTCTTTGCCC ACATCACCAA CAACACCGCT GAGGAGTACG TCTGCCGCCT CCTGCTCTGT GCCCGCACCG  1540
TCAGCTACAA TGGGATCTTG GGGCCCGAGT GTGGCACCAA GTACCTGCTC AACCTCAACC TGGAGCCTTT  1610
CTCTGAGAAG AGCGTTCCTC TTTGCATCCT CTATGAGAAA TACCGTGACT GCCTTACGGA GTCCAACCTC  1680
ATCAAGGTGC GGGCCCTCCT CGTGGAGCCA GTTATCAACA GCTACCTGCT GGCTGAGAGG GACCTCTACC  1750
TGGAGAATCC AGAAATCAAG ATCCGGATCC TTGGGGAGCC CAAGCAGAAA CGCAAGCTGG TGGCTGAGGT  1820
GTCCCTGCAG AACCCGCTCC CTGTGGCCCT GGAAGGCTGC ACCTTCACTG TGGAGGGGGC CGGCCTGACT  1890
GAGGAGCAGA AGACGGTGGA GATCCCAGAC CCCGTGGAGG CAGGGGAGGA AGTTAAGGTG AGAATGGACC  1960
TGCTGCCGCT CCACATGGGC CTCCACAAGC TGGTGGTGAA CTTCGAGAGC GACAAGCTGA AGGCTGTGAA  2030
GGGCTTCCGG AATGTCATCA TTGGCCCCGC CTAA  2064
```

FIGURE 2.

```
MAEELVLERC DLELETNGRD HHTADLCREK LVVRRGQPFW LTLHFEGRNY EASVDSLTFS VVTGPAPSQE  70
AGTKARFPLR DAVEEGDWTA TVVDQQDCTL SLQLTTPANA PIGLYRLSLE ASTGYQGSSF VLGHFILLFN 140
AWCPADAVYL DSEEERQEYV LTQQGFIYQG SAKFIKNIPW NFGQFEDGIL DICLILLDVN PKFLKNAGRD 210
CSRRSSPVYV GRVVSGMVNC NDDQGVLLGR WDNNYGDGVS PMSWIGSVDI LRRWKNHGCQ RVKYGQCWVF 280
AAVACTVLRC LGIPTRVVTN YNSAHDQNSN LLIEYFRNEF GEIQGDKSEM IWNFHCWVES WMTRPDLQPG 350
YEGWQALDPT PQEKSEGTYC CGPVPVRAIK EGDLSTKYDA PFVFAEVNAD VVDWIQQDDG SVHKSINRSL 420
IVGLKISTKS VGRDEREDIT HTYKYPEGSS EEREAFTRAN HLNKLAEKEE TGMAMRIRVG QSMNMGSDFD 490
VFAHITNNTA EEYVCRLLLC ARTVSYNGIL GPECGTKYLL NLNLEPFSEK SVPLCILYEK YRDCLTESNL 560
IKVRALLVEP VINSYLLAER DLYLENPEIK IRILGEPKQK RKLVAEVSLQ NPLPVALEGC TFTVEGAGLT 630
EEQKTVEIPD PVEAGEEVKV RMDLLPLHMG LHKLVVNFES DKLKAVKGFR NVIIGPA 687
```

OLIGORIBONUCLEOTIDES AND METHODS OF USE THEREOF FOR TREATMENT OF FIBROTIC CONDITIONS AND OTHER DISEASES

This application is a divisional of U.S. Ser. No. 12/072,941, filed Feb. 28, 2008, now U.S. Pat. No. 7,939,652 which is a continuation of U.S. Ser. No. 11/045,780, filed Jan. 27, 2005, now abandoned, which claims the benefit of U.S. Provisional Application Nos. 60/540,687, filed Jan. 30, 2004 and No. 60/641,522, filed Jan. 4, 2005, the contents of each of which is hereby incorporated by reference into this application.

Throughout this application various patent and scientific publications are cited. The disclosures of these publications in their entireties are hereby incorporated by reference into this application to more fully describe the state of the art to which this invention pertains.

BACKGROUND OF THE INVENTION siRNAs and RNA Interference

RNA interference (RNAi) is a phenomenon involving double-stranded (ds) RNA-dependent gene specific posttranscriptional silencing. Originally, attempts to study this phenomenon and to manipulate mammalian cells experimentally were frustrated by an active, non-specific antiviral defense mechanism which was activated in response to long dsRNA molecules; see Gil et al. 2000, Apoptosis, 5:107-114. Later it was discovered that synthetic duplexes of 21 nucleotide RNAs could mediate gene specific RNAi in mammalian cells, without the stimulation of the generic antiviral defence mechanisms see Elbashir et al. Nature 2001, 411:494-498 and Caplen et al. Proc Natl Acad Sci 2001, 98:9742-9747. As a result, small interfering RNAs (siRNAs), which are short double-stranded RNAs, have become powerful tools in attempting to understand gene function.

Thus, RNA interference (RNAi) refers to the process of sequence-specific post-transcriptional gene silencing in mammals mediated by small interfering RNAs (siRNAs) (Fire et al, 1998, Nature 391, 806) or microRNAs (miRNAs) (Ambros V. Nature 431:7006, 350-355 (2004); and Bartel D P. Cell. 2004 Jan. 23; 116(2): 281-97 *MicroRNAs: genomics, biogenesis, mechanism, and function*). The corresponding process in plants is commonly referred to as specific post-transcriptional gene silencing or RNA silencing and is also referred to as quelling in fungi. An siRNA is a double-stranded RNA molecule which down-regulates or silences (prevents) the expression of a gene/mRNA of its endogenous (cellular) counterpart. RNA interference is based on the ability of dsRNA species to enter a specific protein complex, where it is then targeted to the complementary cellular RNA and specifically degrades it. Thus, the RNA interference response features an endonuclease complex containing an siRNA, commonly referred to as an RNA-induced silencing complex (RISC), which mediates cleavage of single-stranded RNA having a sequence complementary to the antisense strand of the siRNA duplex. Cleavage of the target RNA may take place in the middle of the region complementary to the antisense strand of the siRNA duplex (Elbashir et al 2001, Genes Dev., 15, 188). In more detail, longer dsRNAs are digested into short (17-29 bp) dsRNA fragments (also referred to as short inhibitory RNAs—"siRNAs") by type III RNAses (DICER, DROSHA, etc., Bernstein et al., Nature, 2001, v. 409, p. 363-6; Lee et al., Nature, 2003, 425, p. 415-9). The RISC protein complex recognizes these fragments and complementary mRNA. The whole process is culminated by endonuclease cleavage of target mRNA (McManus&Sharp, Nature Rev Genet, 2002, v. 3, p. 737-47; Paddison &Hannon, Curr Opin Mol Ther, 2003 June; 5(3): 217-24). For information on these terms and proposed mechanisms, see Bernstein E., Denli A M. Hannon G J: 2001 *The rest is silence*. RNA. 1; 7(11): 1509-21; Nishikura K.: 2001 *A short primer on RNAi: RNA-directed RNA polymerase acts as a key catalyst*. Cell. 116; 107(4): 415-8 and PCT publication WO 01/36646 (Glover et al).

The selection and synthesis of siRNA corresponding to known genes has been widely reported; see for example Chalk A M, Wahlestedt C, Sonnhammer E L, 2004 *Improved and automated prediction of effective siRNA* Biochem. Biophys. Res. Commun. June 18; 319(1): 264-74; Sioud M, Leirdal M., 2004, *Potential design rules and enzymatic synthesis of siRNAs*, Methods Mol. Biol.; 252:457-69; Levenkova N, Ga Q, Rux J J. 2004, *Gene specific siRNA selector* Bioinformatics. 1 12; 20(3): 430-2. and Ui-Tei K, Naito Y, Takahashi F, Haraguchi T. Ohki-Hamazaki H, Juni A, Ueda R, Saigo K., *Guidelines for the selection of highly effective siRNA sequences for mammalian and chick RNA interference* Nucleic Acids Res. 2004 I 9; 32(3):936-48. See also Liu Y, Braasch D A, Nulf C J, Corey D R. *Efficient and isoform-selective inhibition of cellular gene expression by peptide nucleic acids*, Biochemistry, 2004 I 24; 43(7):1921-7. See also PCT publications WO 2004/015107 (Atugen) and WO 02/44321 (Tuschl et al), and also Chiu Y L, Rana T M. *siRNA function in RNAi: a chemical modification analysis*, RNA 2003 September; 9(9):1034-48 and U.S. Pat. Nos. 5,898,031 and 6,107,094 (Crooke) for production of modified/more stable siRNAs.

Several groups have described the development of DNA-based vectors capable of generating siRNA within cells. The method generally involves transcription of short hairpin RNAs that are efficiently processed to form siRNAs within cells. Paddison et al. *PNAS* 2002, 99:1443-1448; Paddison et al. *Genes & Dev* 2002, 16:948-958; Sui et al. *PNAS* 2002, 8:5515-5520; and Brummelkamp et al. *Science* 2002, 296: 550-553. These reports describe methods to generate siRNAs capable of specifically targeting numerous endogenously and exogenously expressed genes.

siRNA has recently been successfully used for inhibition in primates; for further details see Tolentino et al., Retina 24(1) February 2004 I 132-138.

Transglutaminase (TGase) Family

Transglutaminases (EC 2.3.2.13) are a family of enzymes that catalyze the crosslinking of proteins by epsilon-gamma glutamyl lysine isopeptide bonds. The family comprises 9 different enzymes among which are the factor XIIIa (plasma transglutaminase), keratinocyte transglutaminase (TGaseI), epidermal transglutaminase (TGaseIII), prostate transglutaminase (TGaseIV), and tissue-type transglutaminase (TGaseII). Although the overall primary structure of these enzymes is different, they all share a common amino acid sequence at the active site (Y-G-Q-C—W) and a strict calcium dependence for their activity (Lesort M, Tucholski J, Miller M L, Johnson G V, Tissue transglutaminase: a possible role in neurodegenerative diseases. *Prog Neurobiol.* 2000 August; 61(5):439-63).

Transglutaminase II. Transglutaminase II (TGaseII) also known as Protein-glutamine gamma-glutamyltransferase, TGase C, TGC, TG(C), and tissue-type transglutaminase, is a unique multifunctional enzyme with dual enzymatic activity:
1) The enzyme acts as a TGase protein ($Ca^{2+}$ activated, GTP-inactivated) with crosslinking activities (i.e. it catalyzes reactions resulting in protein cross-links and/or covalent incorporation of biogenic amines). TGase further catalyzes the formation of a covalent glutamyl-lysyl bond, a unique isopeptide bond that is highly resistant to proteolysis and denaturants and that cannot be disrupted by any known vertebrate endopeptidase.

2) The enzyme also acts as a GTP-binding protein that transduces the activating signal from alpha 1B and alpha 1D adrenergic receptors, from TP alpha thromboxane A2 receptor and from oxytocin receptor to phospholipase C delta 1 (i.e. it activates inositol phosphate Production, $Ca^{2+}$ mobilization etc.). It has been shown that both alpha 1D adrenergic receptor and PLC act as guanine nucleotide exchanging factor for transglutaminase II (Baek K J, Kang S, Daimon D, Im M, *Phospholipase C-delta1 is a guanine nucleotide exchanging factor for transglutaminase II (G alpha h) and promotes alpha 1B-adrenoreceptor-mediated GTP binding and intracellular calcium release*. J Biol Chem. 2001 Feb. 23; 276(8):5591-7).

The dual function of this enzyme is separate and the active sites are located at different positions (Im M J, Russell M A, Feng J F, *Transglutaminase II: a new class al GTE-binding protein with new biological functions*. Cell Signal. 1997 November; 9(7):477-82), and inhibition of crosslinking activity of TGaseII may be achieved without the interference with its G-protein function.

TGaseII: Subcellular Localization and Fibrosis Related Intracellular Signaling Activity TGaseII is ubiquitously expressed and can be found in association with ECM and intracellularly, both as membrane bound and as cytosolic protein. The GTP-binding activity is higher in the membrane fraction of TGase and the cross-linking activity is higher in the cytosolic and extracellular fraction. On the cell surface, TGase binds to fibronectin via its 42 kDa gelatin-binding domain. The cross-linking of fibronectin with collagen contributes to structural stabilization of the ECM rendering the matrix resistant to proteolysis by matrix mettaloproteinases. Thus TGaseII, by favoring deposition of extracellular proteins and inhibiting breakdown of said proteins, contributes to ECM accumulation, a phenomenon that is central to the formation of tissue fibrosis.

In addition, TGase mediates the binding of latent TGF-beta to the ECM, a required step for a proper subsequent processing of this pro-fibrotic factor, which finally results in the release of active TGF-beta (Le et al., Connect Tissue Res. 2001; 42(4):245-51 Rosenthal et al., Arthritis Rheum. 2000 August; 43(8):1729-33).

In the cytoplasm, TGaseII may activate RhoA, a small G protein of the ras family known to have an important role in cytoskeletal rearrangement, regulation of cell morphology and differentiation. Activation of TGaseII results in an increased transamidation of RhoA, which then functions as a constitutively active G-protein showing increased binding to and activation of its downstream target ROCK-2 (Rho-associated kinase) (Singh et al. EMBO J. 2001 May 15; 20(10): 2413-23). The specific ROCK kinase inhibitor, Y-27632, showed anti-fibrotic effect in DUO model of renal fibrosis as well as in the models of liver or lung fibrosis (Nagatoya K, Moriyama T, Kawada N, Takeji M, Oseto S, Murozono T, Ando A, Imai E, Hori M. Y-27632 was found to prevent tubulointerstitial fibrosis in mouse kidneys with unilateral urethral obstruction. Kidney Int. 2002 May; 01(5): 1684-95; Murata T, Arii S, Nakamura T, Mori A, Kaido T, Furuyama H, Furumoto K, Nakao T, Isobe N, Imamura M, *Inhibitory effect of Y-27632, a ROCK inhibitor, on progression of rat liver fibrosis in association with inactivation of hepatic stellate cells*. J. Hepatol. 2001 October; 35(4):474-81; Shimizu Y, Dohashi K, Iizuka K, Horie T, Suzuki K, Tukagoshi H, Nakazawa T, Nakazato Y, Mori M, *Contribution of small GTPase Rho and its target protein ROCK in a marine model of lung fibrosis*. Am J Respir Crit Care Med, 2001 January; 163(1): 210-7). Recently, a unique function of TGaseII contributing to activation of NFkB, a transcription factor with a well-documented pro-fibrotic activity was described (Baud et al., J Soc Biol. 2002; 196(4):269-73, Lee at al. J Biol Chem. 2004 Dec. 17; 279(51):53725-35).

Fibrotic Diseases

Fibrotic diseases are all characterized by the excess deposition of a fibrous material within the extracellular matrix, which contributes to abnormal changes in tissue architecture and interferes with normal organ function. Unfortunately, although fibrosis is widely prevalent, debilitating and often life threatening, there is no effective treatment currently available.

All tissues damaged by trauma respond by the initiation of a wound-healing program. Fibrosis, a type of disorder characterized by excessive scarring, occurs when the normal self-limiting process of wound healing response is disturbed, and causes excessive production and deposition of collagen. As a result, normal organ tissue is replaced with scar tissue, which eventually leads to the functional failure of the organ.

Fibrosis may be initiated by diverse causes and in various organs. Liver cirrhosis, pulmonary fibrosis, sarcoidosis, keloids and kidney fibrosis are all chronic conditions associated with progressive fibrosis, thereby causing a continuous loss of normal tissue function.

Acute fibrosis (usually with a sudden and severe onset and of short duration) occurs as a common response to various forms of trauma including accidental injuries (particularly injuries to the spine and central nervous system), infections, surgery, ischemic illness (e.g. cardiac scarring following heart attack), burns, environmental pollutants, alcohol and other types of toxins, acute respiratory distress syndrome, radiation and chemotherapy treatments).

For further information on different types of fibrosis see: Molina V, Blank M, Shoenfeld Y. (2002), *"Fibrotic diseases"*, Harefuah, 141(11): 973-8, 1009; Yu L, Noble N A, Border W A (2002), *"Therapeutic strategies to halt renal fibrosis"*, Curr Opin Pharmacol. 2(2):177-81; Keane W F, Lyle P A. (2003), *"Recent advances in management of type 2 diabetes and nephropathy: lessons from the RENAAL study"*, Am J Kidney Dis. 41(3 Suppl 2): S22-5; Bohle A, Kressel G, Muller C A, Muller G A. (1989), *"The pathogenesis of chronic renal failure"*, Pathol Res Pract. 185(4):421-40; Kikkawa R, Togawa M, Isono M, Isshiki K, Haneda M. (1997), *"Mechanism of the progression of diabetic nephropathy to renal failure"*, Kidney Int Suppl. 62:S39-40; Bataller R, Brenner D A. (2001), *"Hepatic stellate cells as a target for the treatment of liver fibrosis"*, Semin Liver His. 21(3):437-51; Gross T J, Hunninghake G W, (2001) *"Idiopathic pulmonary fibrosis"*, N Engl J Med. 345(7):517-25; Frohlich E D. (2001) *"Fibrosis and ischemia: the real risks in hypertensive heart disease"*, Am J Hypertens; 14(6 Pt 2):194S-199S.

Liver Fibrosis

Liver fibrosis (LF) is a generally irreversible consequence of hepatic damage of several etiologies. In the Western world, the main etiologic categories are: alcoholic liver disease (30-50%), viral hepatitis (30%), biliary disease (5-10%), primary hemochromatosis (5%), and drug-related and cryptogenic cirrhosis of unknown etiology (10-15%). Wilson's disease, $\alpha_1$-antitrypsin deficiency and other rare diseases also have liver fibrosis as one of the symptoms Scheinberg I H, Sternlieb I., *Wilson disease and idiopathic copper toxicosis*. Am J Clin Nutr 1996 May; 63(5):842S-5S; Parfrey H, Mahadeva R, Lomas D A., *Alpha(1)-antitrypsin deficiency, liver disease and emphysema*. Int J Biochem Cell Biol. 2003 July; 35(7): 1009-14.

Liver cirrhosis, the end stage of liver fibrosis, frequently requires liver transplantation and is among the top ten causes of death in the Western world.

Anti-inflammatory agents, which cause inhibition of activation of hepatic stellate cells, stimulation of growth of hepatocytes and inhibition of post translational modification of collagen have all been used to treat liver fibrosis. However, due to the lack of selective targeting, these treatments suffer from, inter alia, the drawbacks of severe side effects.

For more information see Friedman S L. (2003), "*Liver fibrosis—from bench to bedside*", J Hepatol. 38 Suppl 1:S38-53; Albanis E, Safadi R, Friedman S L. (2003), "*Treatment of hepatic fibrosis: almost there*", Curr Gastroenterol Rep. 5(1): 48-56. See also Grenard P, Bresson-Hadni S, El Alaoui S, Chevallier M, Vuitton D A, Ricard-Blum S., *Transglutaminase-mediated cross-linking is involved in the stabilization of extracellular matrix in human liver fibrosis*. J Hepatol. 2001 September; 35(3):367-75; Mirza A, Liu S L, Frizell E, Zhu J, Maddukuri S, Martinez J, Davies P, Schwarting R, Norton P, Zern M A., *A role for tissue transglutaminase in hepatic injury and fibrogenesis, and its regulation by NF-kappaB*. Am J Physiol. 1997 February; 272(2 Pt 1):G28-8).

Kidney Fibrosis and Related Conditions
Chronic Renal Failure (CRF)

Chronic renal failure is a gradual and progressive loss of the ability of the kidneys to excrete wastes, concentrate urine, and conserve electrolytes. CRF is slowly progressive. It most often results from any disease that causes gradual loss of kidney function, and fibrosis is the main pathology that produces CRF.

Diabetic Nephropathy

Diabetic nephropathy, hallmarks of which are glomerulosclerosis and tubulointerstitial fibrosis, is the single most prevalent cause of end-stage renal disease in the modern world, and diabetic patients constitute the largest population on dialysis. Such therapy is costly and far from optimal. Transplantation offers a better outcome but suffers from a severe shortage of donors. More targeted therapies against diabetic nephropathy (as well as against other types of kidney pathologies) are not developed, since molecular mechanisms underlying these pathologies are largely unknown. Identification of an essential functional target gene that is modulated in the disease and affects the severity of the outcome of diabetes nephropathy has a high diagnostic as well as therapeutic value.

Origins of Kidney Pathology

Many pathological processes in the kidney (e.g., glomerular nephritis, physical obstructions, toxic injuries, metabolic and immunological diseases) eventually culminate in similar or identical morphological changes, namely glomerulosclerosis and tubulointerstitial fibrosis. Thus, different types of insults converge on the same single genetic program resulting in two hallmarks of fibrosis: the proliferation of fibroblasts and overproduction by them of various protein components of connective tissue. In addition, thickening of the basal membrane in the glomeruli accompanies interstitial fibrosis and culminates in glomerulosclerosis. See also Johnson T S, Skill N J, El Nahas A M, Oldroyd S D, Thomas G L, Douthwaite J A, Haylor J L, Griffin M, *Transglutaminase transcription and antigen translocation in experimental renal scarring*. J Am Soc Nephrol. 1999 October; 10(10):2146-57; Johnson T S, Griffin M, Thomas G L, Skill J, Cox A, Yang B, Nicholas B, Birckbichler P J, Muchaneta-Kubara C, Meguid El Nahas A, *The role of transglutaminase in the rat subtotal nephrectomy model of renal fibrosis*. J Clin Invest. 1997 Jun. 15; 99(2): 2950-60).

Pulmonary Fibrosis

Interstitial pulmonary fibrosis (IPE) is scarring of the lung caused by a variety of inhaled agents including mineral particles, organic dusts, and oxidant gases, or by unknown reasons (idiopathic lung fibrosis). The disease afflicts millions of individuals worldwide, and there are no effective therapeutic approaches. A major reason for the lack of useful treatments is that few of the molecular mechanisms of disease have been defined sufficiently to design appropriate targets for therapy (Lasky J A., Brody A R. (2000), "*Interstitial fibrosis and growth factors*", Environ Health Perspect.; 108 Suppl 4: 751-62).

The cellular substrate of pathogenesis of pulmonary fibrosis includes endothelial and epithelial cell injury, production of inflammatory cells and their mediators, and fibroblast activation., Fibrosis is believed to be related to a dysregulation in cross-talk between inflammatory and structural cells, mediated by various cytokines, chemokines and growth factors, which are responsible for the maintenance of tissue homeostasis and which coordinate the response to injury (Kelly M, Kolb M, Bonniatid P, Gauldie J. (2003), "*Re-evaluation of fibrogenic cytokines in lung fibrosis*", Curr Pharm Des. 9(1): 39-49).

Conventional therapy consisting of glucocorticoids or cytotoxic drugs is usually ineffective in preventing progression of the disease. It is believed that further understanding of the molecular mechanisms of endothelial and epithelial cell injury, inflammatory reaction, fibroblast proliferation, collagen deposition and lung repair, is necessary for the development of effective treatments against pulmonary fibrosis (Kuwano K, Hagimoto N, Hara N. (2001), "*Molecular mechanisms of pulmonary fibrosis and current treatment*", Curr Mol Med. 1(5):551-73). See also Griffin M, Smith L L, Wynne J., *Changes in transglutaminase activity in an experimental model of pulmonary fibrosis induced by Paraquat*. Br. J. Exp. Pathol. 1979 December; 60(6):653-61).

Cardiac Fibrosis

Heart Failure is unique among the major cardiovascular disorders in that it alone is increasing in prevalence while there has been a striking decrease in other conditions. Some of this can be attributed to the aging of the populations of the United States and Europe. The ability to salvage patients with myocardial damage is also a major factor, as these patients may develop progression of left ventricular dysfunction due to deleterious remodelling of the heart.

The normal myocardium is composed of a variety of cells, cardiac myocytes and noncardiomyocytes, which include endothelial and vascular smooth muscle cells and fibroblasts. (Weber K T. (2000), "*Fibrosis and hypertensive heart disease*", Curr Opin Cardiol. 15(4):264-72).

Structural remodeling of the ventricular wall is a key determinant of clinical outcome in heart disease. Such remodeling involves the production and destruction of extracellular matrix proteins, cell proliferation and migration, and apoptotic and necrotic cell death. Cardiac fibroblasts are crucially involved in these processes, producing growth factors and cytokines that act as autocrine and paracrine factors, as well as extracellular matrix proteins and proteinases. Recent studies have shown that the interactions between cardiac fibroblasts and cardiomyocytes are essential for the progression of cardiac remodeling of which the net effect is deterioration in cardiac function and the onset of heart failure (Manabe I, Shindo T, Nagai R. (2002), "*Gene expression in fibroblasts and fibrosis: involvement in cardiac hypertrophy*", Circ Res. 13; 91(12):1103-13).

The use of agents to block the renin-angiotensin-aldosterone and sympathetic nervous systems has been shown to inhibit (and sometimes even reverse) cardiac remodelling and to improve the clinical course of patients with cardiac dysfunction. However, drugs aiming at direct inhibition or reduction of fibrosis are not yet available. See also Greenberg B. (2001), "*Treatment of heart failure: state of the art and prospectives*", J Cardiovasc Pharmacol. 38 Suppl 2:S59-63, Zhang Z, Vezza R, Plappert T, McNamara P, Lawson J A, Austin S, Pratico D, Sutton M S, FitzGerald G A, *COX-2-dependent cardiac failure in Gh/tTG transgenic mice*. Circ Res. 2003 May 30; 92(10):1153-61. Epub 2003 April 17; Hwang K C, Gray C D, Sweet W E, Moravec C S, Im M J., *Alpha 1-adrenergic receptor coupling with Gh in the failing human heart*. Circulation. 1996 Aug. 15; 94(4):718-26.

Neurological Diseases

Polyglutamine diseases are a group of neurological diseases that are caused by expansion of CAG trinucleotide repeats coding for polyglutamine insert. Polyglutamine diseases include Huntington's disease (HD), spinobulbar muscular atrophy, dentatorubral-pallidoluysian atrophy and spinocerebellar ataxias (SCAs) 1, 2, 3, 6, 7 and 17. All these diseases are characterized by the presence of expansion of polyglutamine stretches (exceeding 35-40 glutamines), thus forming intranuclear aggregates, which leads to neuronal death. Alzheimer's disease (AD) is the most common cause of cognitive impairment in older patients and is expected to increase greatly in prevalence. Neurofibrillary degeneration, associated with the formation of paired helical filaments (PHF), is one of the critical neuropathological hallmarks of Alzheimer's disease (AD). Parkinson disease is a neurodegenerative disorder of aging characterized by a selective and progressive loss of dopaminergic neurons within the substantia nigra. See also Mastroberardino P G, Iannicola C, Nardacci R, Bernassola F, De Laurenzi V, Melino G, Moreno S. Pavone F, Oliverio S, Fesus L, Piacentini M. *Tissue transglutaminase ablation reduces neuronal death and prolongs survival in a mouse model of Huntington's disease*. Cell Death Differ, 2002 September; 9(9):873-80; Karpuj M V, Becher M W, Springer J F, Chabas D, Youssef S. Pedotli R. Mitchell D, Steinman L., *Prolonged survival and decreased abnormal movements in transgenic model of Huntington disease, with administration of the transglutaminase inhibitor cystamine*. Nat Med, 2002 February; 8(2):143-9; Citron B A, Suo Z, SantaCruz K, Davies P J, Qin F, Festoff B W., *Protein crosslinking, tissue transglutaminase, alternative splicing and neurodegeneration*. Neurochem Int. 2002 January; 40(1):69-78; Chen J S, Mehta K., *Tissue transglutaminase: an enzyme with a split personality*. Int J Biochem Cell Biol. 1999 August; 31(8):817-36.

Osteoarthritis

Among the main characteristics of osteoarthritis are the degradation of articular cartilage and the formation of new bone at the joint edges, so-called osteophytes. See Van den Berg W B., *Growth factors in experimental osteoarthritis: transforming growth factor beta pathogenic?* J Rheumatol Suppl. 1995 February; 43:143-5; Scharstuhl A, Glansbeek H L, Van Beuningen H M, Vitters E L, Van der Kraan P M, Van den Berg W B., *Inhibition of endogenous TGF-beta during experimental osteoarthritis prevents osteophyte formation and impairs cartilage repair*. J Immunol. 2002 Jul. 1; 169(1): 507-14; Karpouzas G A, Terkeltaub R S., *New developments in the pathogenesis of articular cartilage calcification*. Curr Rheumatol Rep. 1999 December; 1(2):121-7

Ocular Diseases

Age-related cataracts: Cataracts are characterized by aggregation and covalent cross-linking of the crystallins, the major structural proteins of the eye lens, resulting in increase light scattering, opacification and cataract. Disturbance of calcium homeostasis in the tissue is one of the factors implicated in cataractogenesis, see Shridas et al., FEBS Lett. 2001 Jun. 22; 499(3):245-50; Shin et al, J Biol Chem. 2004 Apr. 9; 279(15):15032-9; Wan et al., Br J Ophthalmol. 2002 November; 86(11):1293-8. and Takeuchi N, Kamei A. Biol Pharm Bull. 2000 March; 23(3):283-90.

Proliferative vitreoretinopathy Proliferative vitreoretinopathy (PVR) is the most common complication following retinal detachment and associated with a retinal hole or break. PVR refers to the growth of cellular membranes within the vitreous cavity and on the front and back surfaces of the retina containing retinal pigment epithelial (RPE) cells. These membranes, which are essentially scar tissues, exert traction on the retina and may result in recurrences of retinal detachment, even after an initially successful retinal detachment procedure.

Migration and adhesion of dislocated retinal pigment epithelial (RPE) cells to a fibronectin-rich extracellular matrix is an initial step in proliferative vitreoretinopathy (PVR). See also Casaroli-Marano R P et al Invest Ophthalmol V is Sci. 1999 August; 40(9):2062-72), and Priglinger S et al, Invest Ophthalmol Vis Sci. 2004 March; 45(3):955-63; Priglinger et al, Invest Ophthalmol Vis Sci. 2003 January; 44(1):355-64.

Fibrosis following glaucoma filtering operation. The goal of the glaucoma filtration procedure is to create a new passageway by which aqueous fluid inside the eye can escape, thereby lowering the pressure. The filter, therefore, allows the drainage of fluid from inside the anterior chamber of the eye to a "pocket" created between the conjuctiva, which is the outermost covering of the eye, and the sclera, which is the underlying white anatomical structure of the eye. The fluid is eventually absorbed by blood vessels. Unfortunately, due to postoperational scarring, the generated drainage system may be blocked requiring additional surgical intervention(s).

Current anti-scarring regimens (Mitomycin C or 5FU) are limited due to the complications involved (e.g. blindness) e.g. see Cordeiro M F, Gay J A, Khaw P T., *Human anti-transforming growth factor-beta2 antibody: a new glaucoma anti-scarring agent* Invest Ophthalmol Vis Sci. 1999 September; 40(10):2225-34.

In conclusion, there are no effective modes of therapy for the diseases described above, and there is a need, therefore, to develop novel effective compounds and methods of treatment for these purposes.

SUMMARY OF THE INVENTION

The invention provides novel double stranded oligoribonucleotides. These oligoribonucleotides inhibit human TGaseII via the mechanism of RNA interference. The invention also provides a pharmaceutical composition comprising such an oligoribonucleotide, and a vector capable of expressing the oligoribonucleotide. The present invention also provides a method of treating a patient suffering from a fibrosis-related pathology comprising administering to the patient the oligoribonucleotide typically as a pharmaceutical composition, in a therapeutically effective dose so as to thereby treat the patient. The present invention also contemplates treating other diseases and conditions. The invention also relates to treatment of fibrotic and other diseases by use of an antibody to TGaseII polypeptide.

BRIEF DESCRIPTION OF THE FIGURES

FIG. 1. This figure sets forth the nucleotide sequence of the human TGaseII cDNA-(gi|3653650|ref|XM_009482.3|-ORF)—SEQ ID NO: 1.

FIG. 2. This figure sets forth the amino acid sequence of the human TGaseII corresponding polypeptide—SEQ ID NO:2.

Figure 3:
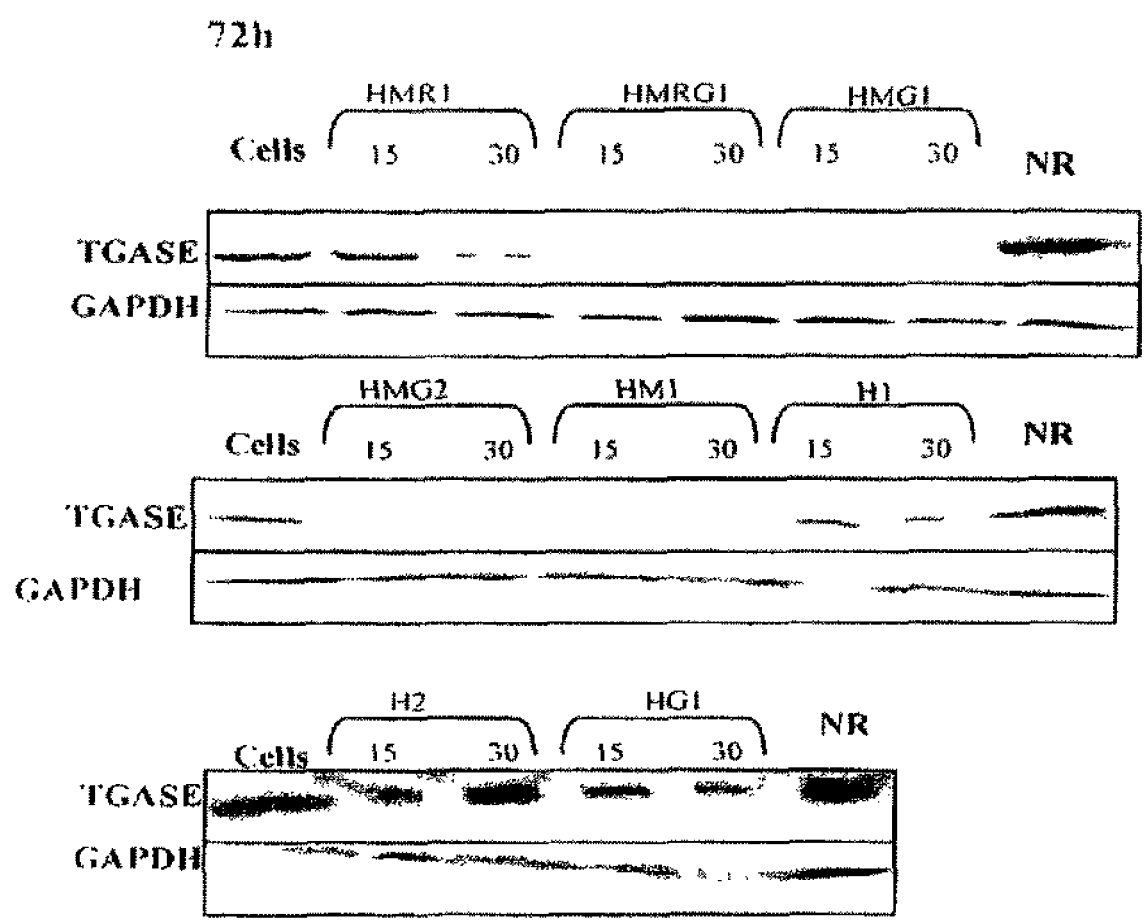
FIG. 3. Western Blot results demonstrating the effect of various TGaseII siRNAs on human TGaseII polypeptide expression.

The figure demonstrates the activity of various siRNAs in reducing expression of human TGase polypeptide in HeLa cells, 72 hr following siRNA transfection. GAPDH expression serves as control for protein loading. The numbers 15 and 30 represent concentration of the oligonucleotide in nM. "Cells" (first lane in each panel) stands for—nontransfected control cells. The last lane in each panel contains protein extracts from HeLa cells transfected with non-relevant (NR) siRNA, to ensure that the decrease in TGaseII expression is specific to the anti TGase siRNAs activity.

DETAILED DESCRIPTION OF THE INVENTION

The present invention provides a method for treatment of various pathologies, as recited below, in a subject in need of such treatment which comprises: administering to the subject an amount of an inhibitor of TGaseII polypeptide sufficient to effect a substantial inhibition of the TGaseII activity so as to thereby treat the subject. The TGaseII inhibitor may be L683685, an antibody to TGaseII polypeptide or an siRNA to TGaseII RNA or any of the TGaseII inhibitors known in the art (for further information on such inhibitors see for example: U.S. Pat. Nos. 5,021,440; 4,968,713 and 5,098,707). In particular the present invention relates to specific siRNAs targeting TGaseII RNA and the use thereof. The use of neutralizing antibodies against TGaseII is also disclosed.

The present invention relates generally to compounds which down-regulate expression of the human TGaseII gene particularly to novel small interfering RNAs (siRNAs), and to the use of these novel siRNAs in the treatment of various diseases and medical conditions in particular fibrotic diseases, diseases related to fibrotic scarring and other diseases related to aberrant expression of Transglutaminase II.

The present invention provides methods and compositions for inhibiting expression of the target TGaseII gene in vivo. In general, the method includes administering oligoribonucleotides, such as small interfering RNAs (i.e., siRNAs) that are targeted to a particular mRNA and hybridize to, or interact with, it under biological conditions (within the cell), or a nucleic acid material that can in produce siRNA in a cell, its an amount sufficient to down-regulate expression of a target gene by an RNA interference mechanism. In particular, the subject method can be used to inhibit expression of the TGaseII gene for treatment of disease.

Thus, the inhibitor of TGaseII expression (transcription or translation) or polypeptide activity may be inter alia siRNA, antibodies, preferably neutralizing antibodies or fragments thereof, including single chain antibodies, antisense oligonucleotides, antisense DNA or RNA molecules, proteins, polypeptides and peptides including peptide-mimetics and dominant negatives, and also expression vectors expressing all the above. Additional inhibitors may be small chemical molecules, which generally have a molecular weight of less than 2000 daltons, more preferably less than 1000 daltons, even more preferably less than 500 daltons. These inhibitors may act as follows: small molecules may affect expression and/or activity; antibodies may affect activity; all kinds of antisense may affect TGaseII expression; and dominant negative polypeptides and peptidomimetics may affect activity; expression vectors may be used inter alia for delivery of antisense or dominant-negative polypeptides or antibodies.

In accordance with the present invention, the siRNA molecules or inhibitors of Transglutaminase II, such as antibodies, may be used as drugs to treat various pathologies including fibrosis related pathologies (as defined below) and also to treat ocular diseases including cataract, cardiovascular diseases, neurological diseases, polyglutamine diseases (including Huntington's disease (HD), spinobulbar muscular atrophy, dentatorubral-pallidoluysian atrophy and spinocerebellar ataxias (SCAs) 1, 2, 3, 6, 7 and 17), Alzheimer's and Parkinson's disease, and osteoarthritis.

As used herein, the terms "Transglutaminase II gene", or "TGaseII gene", or "TGase gene" is defined as any homolog of TGaseII gene having preferably 90% homology, more preferably 95% homology, and even mom preferably 98% homology to the amino acid encoding region of SEQ ID NO:1, or nucleic acid sequences which bind to the TGaseII gene under conditions of highly stringent hybridization, which are well-known in the art (for example, see Ausubel et al., Current Protocols in Molecular Biology, John Wiley and Sons, Baltimore, Md. (1988), updated in 1995 and 1998).

As used herein, the term "Transglutaminase II polypeptide", or "TGaseII polypeptide", or "TGase" is defined as any homolog of TGaseII polypeptide having preferably 90% homology, more preferably 95% homology, and even more preferably 98% homology to SEQ ID NO:2, as either full-length or fragments or a domain thereof, as a mutant of the polypeptide encoded by a spliced variant nucleic acid sequence, as a chimera with other polypeptides, provided that any of the above has the same or substantially the same biological function as the TGaseII polypeptide. TGaseII polypeptide, or a TGaseII polypeptide homolog, may be present in different forms, including but not limited to soluble protein, membrane-bound (either in purified membrane preparations or on a cell surface), bead-bound, or any other form presenting TGaseII protein or fragments and polypeptides derived thereof.

As used herein, an "interactor" is a molecule with which TGaseII binds or interacts or activates in nature; for example, a molecule on the surface of a TGaseII polypeptide expressing cell, a molecule on the surface of a second cell or a cytoplasmic molecule. An interactor may be a ligand that is activated by TGaseII alone or by TGaseII as part of a complex with other components. An interactor may be a component of a signal transduction pathway that facilitates transduction of an extracellular signal from TGaseII through the cell membrane and into the cell. An interactor, for example, can be a second intercellular protein that mediates downstream signaling from TGaseII. The interactor is a molecule with which TGase binds in competition with a known TGase substrate (e.g. fibronectin).

As used herein, the term "lysyl donor" or "K donor" is defined as any polypeptide having the ability to donate a lysyl side chain to allow the formation of gamma-glutamyl-lysine bonds during transglutamination process.

As used herein, the term "glutamyl donor" or "Q donor" is defined as any polypeptide having the ability to donate glutamine side chain to allow the formation of gamma-glutamyl-lysine bonds during transglutamination process.

The present invention provides double-stranded oligoribonucleotides (siRNAs), which down-regulate the expression of TGaseII. The downregulation of the expression of transglutminase II can be measured by e.g., measuring the amount of the lysyl-glutamyl crosslinked material produced in the presence of the siRNAs or by direct assessment of the amounts of TGaseII mRNA or polypeptide. The amount of TGaseII mRNA may be measured by e.g., by Northern blotting, RNase protection, RT-PCR or real-time PCR. The amount of TGaseII polypeptide may be measured by immunoblotting or by immunoprecipitation or by ELISA with TGaseII-specific antibodies.

An siRNA of the invention is a duplex oligoribonucleotide in which the sense strand is derived from the mRNA sequence of gene TGaseII, and the antisense strand is complementary to the sense strand. In general, some deviation from the target mRNA sequence is tolerated without compromising the siRNA activity (see e.g. Czaudema et al 2003 Nucleic Acids Research 31(11), 2705-2716). An siRNA of the invention inhibits gene expression on a post-transcriptional level with or without destroying the mRNA. Without being bound by theory, siRNA may target the mRNA for specific cleavage and degradation and/or may inhibit translation from the targeted message.

There are at least two variant TGaseII polypeptides, for which the GeneBank references are variant 2 NM_198951.1 GI:39777598 and variant 1 NM_004613.2 GI:39777596. The sequence given in FIG. 1 is the nucleotide sequence of variant 2 (GI:39777598). Both variants and any other similar minor variants are included in the definition of TGaseII polypeptide and in the definition of the TGaseII genes encoding them.

As used herein, the term "TGaseII gene" is defined as the naturally-occurring human gene including any allelic variant thereof as well as any homolog of the TGaseII gene having preferably 90% homology, more preferably 95% homology, and even more preferably 98% homology to the amino acid encoding region of SEQ ID NO:1 or nucleic acid sequences which bind to the TGaseII gene under conditions of highly stringent hybridization, which are well-known in the art (for example, see Ausubel et al., Current Protocols in Molecular Biology, John Wiley and Sons, Baltimore, Md. (1988), updated in 1995 and 1998.

As used herein, the term "TGaseII", or "TGaseII polypeptide" is defined as the naturally-occurring polypeptide product of the gene including any allelic variant thereof as well as any homolog of the TGaseII polypeptide having preferably 90% homology, more preferably 95% homology, and even more preferably 98% homology to SEQ ID NO:2, as either full-length or a fragment or a domain thereof, as a mutant or the polypeptide encoded by a spliced variant nucleic acid sequence, as a chimera with other polypeptides, provided that any of the above has the same or substantially the same biological function as the TGaseII polypeptide.

More particularly, the invention provides a compound having the structure:

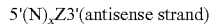

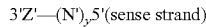

wherein each N and N' is a ribonucleotide which may be modified or unmodified in its sugar residue and $(N)_x$ and $(N')_y$ is oligomer in which each consecutive N or N' is joined to the next N or N' by a covalent bond;

wherein each of x and y is an integer between 19 and 40;

wherein each of Z and Z' may be present or absent, but if present is dTdT and is 2l1 covalently attached at the 3' terminus of the strand in which it is present;

and wherein the sequence of $(N)_x$, comprises any one of the antisense sequences present in Tables A, B and C It will be readily understood by those skilled in the art that the compounds of the present invention consist of a plurality of nucleotides which are linked through covalent linkages. Each such covalent linkage may be a phosphodiester linkage, a phosphothioate linkage, or a combination of both, along the length of the nucleotide sequence of the individual strand. Other possible backbone modifications are described inter alia in U.S. Pat. Nos. 5,587,361; 6,242,589; 6,277,967; 6,326,358; 5,399,676; 5,489,677; and 5,596,086.

In particular embodiments, x and y are preferably an integer between about 19 to about 27, most preferably from about 19 to about 23. In a particular embodiment of the compound of the invention, x may be equal to y (viz., x=y) and in preferred embodiments x=y=19 or x=y=21. In a particularly preferred embodiment x=y=19.

In one embodiment of the compound of the invention, Z and Z' are both absent; in another embodiment one of Z or Z' is present.

In one embodiment of the compound of the invention, all of the ribonucleotides of the compound are unmodified in their sugar residues.

In some embodiments of the compound of the invention, at least one ribonucleotide is modified in its sugar residue, preferably a modification at the 2' position. The modification at the 2' position results in the presence of a moiety which is preferably selected from the group comprising amino, fluoro, methoxy, alkoxy and alkyl groups. En a presently most preferred embodiment the moiety at the 2' position is methoxy (2'-0-methyl).

In some embodiments of the invention, alternating ribonucleotides are modified in both the antisense and the sense strands of the compound.

In particularly preferred embodiments of the invention, the antisense strand is phosphorylated at the 5' terminus, and may or may not be phosphorylated at the 3' terminus; and the sense strand may or may not be phosphorylated at the 5' terminus and at the 3' terminus.

In another embodiment of the compound of the invention, the ribonucleotides at the 5' and 3' termini of the antisense strand are modified in their sugar residues, and the ribonucleotides at the 5' and 3' termini of the sense strand are unmodified in their sugar residues.

The invention further provides a vector capable of expressing any of the aforementioned oligoribonucleotides in unmodified form in a cell after which appropriate modification may be made.

The invention also provides a composition comprising one or more of the compounds of the invention in a carrier, preferably a pharmaceutically acceptable carrier.

The invention also provides a composition comprising a carrier and one or more of the compounds of the invention in an amount effective to down-regulate expression in a cell of a human TGaseII gene, which compound comprises a sequence substantially complementary to the sequence of $(N)_x$.

The invention also provides a method of down-regulating the expression of a human TGaseII gene by at least 50% as compared to a control comprising contacting an mRNA transcript of the gene with one or more of the compounds of the invention.

In one embodiment the compound is down-regulating TGaseII, whereby the down-regulation of TGaseII is selected from the group comprising down-regulation of TGaseII function (which may be examined by an enzymatic assay or a binding assay with a known interactor of the native gene/polypeptide, inter alia), down-regulation of TGaseII protein (which may be examined by Western blotting, ELISA or immuno-precipitation, inter alia) and down-regulation of TGaseII mRNA expression (which may be examined by Northern blotting, quantitative RT-PCR, in-situ hybridisation or microarray hybridisation, inter alia).

The invention also provides a method of treating a patient suffering from fibrosis or a fibrosis-related pathology, comprising administering to the patient a composition of the invention in a therapeutically effective dose so as to thereby treat the patient.

The invention also provides a method of treating a patient suffering from a pathology related to aberrant cross-linking of cellular proteins via Transglutaminase II comprising administering to the patient a composition of the invention in a therapeutically effective dose so as to thereby treat the patient.

The invention also provides a use of a therapeutically effective dose of one or more compounds of the invention for the preparation of a composition for promoting recovery in a patient suffering from fibrosis or a fibrosis-related pathology or a pathology related to aberrant crosslinking of cellular proteins via Transglutaminase II.

Fibrotic diseases or diseases in which fibrosis is evident (fibrosis-related pathology) include both acute and chronic forms of fibrosis of organs, including all etiological variants of the following: pulmonary fibrosis, including interstitial lung disease and fibrotic lung disease, liver fibrosis, cardiac fibrosis including myocardial fibrosis, kidney fibrosis including chronic renal failure, skin fibrosis including scleroderma, keloids and hypertrophic scars; myelofibrosis (bone marrow so fibrosis); all types of ocular scarring including proliferative vitreoretinopathy (PVR) and scarring resulting from surgery to treat cataract or glaucoma; inflammatory bowel disease of variable etiology, macular degeneration, Grave's ophthalmopathy, drug induced ergotism, psoriasis, glioblastoma in Li-Fraumeni syndrome, sporadic glioblastoma, myleoid leukemia, acute myelogenous leukemia, myelodysplastic syndrome, myeloproferative syndrome, gynecological cancer, Kaposi's sarcoma, Hansen's disease, and collagenous colitis.

The compounds of the invention may be used to treat many other diseases and conditions apart from fibrotic diseases. Other indications may be ocular diseases including cataract, cardiovascular diseases especially cardiac hypertrophy, atherosclerosis/restenosis, neurological diseases, including polyglulaminc diseases (such as Huntington's disease), spinobulbar muscular atrophy, dentatortibral-pallidoluysian atrophy and spinocerebellar ataxias (SCAB) 1, 2, 3, 6, 7 and 17, Alzheimer's disease and Parkinson's disease.

The compound may have homologs wherein up to two of the ribonucleotides in each terminal region base is altered; the terminal region refers to the four terminal ribonucleotides e.g. refers to bases 1-4 and/or 16-19 in a 19-mer sequence and to bases 1-4 and/or 18-21 in a 21-mer sequence.

The preferred oligonucleotides of the invention are the oligonucleotides listed in Tables A, B and C, preferably the oligonucleotides targeting human cDNA. The most preferred oligonucleotides of the invention are the oligonucleotides having inhibitory activity as demonstrated in Table D, preferably oligonucleotides targeting human TGaseII cDNA.

The presently most preferred compound of the invention is a blunt-ended 19-mer oligonucleotide, i.e. x=y=19 and Z and Z' are both absent; the oligonucleotide is phosphorylated at the 5' position of the antisense strand and at the 3' position of the sense strand wherein alternating ribonucleotides are modified at the 2' position in both the antisense and the sense strands, wherein the moiety at the 2' position is methoxy (2'-0-methyl) and wherein the ribonucleotides at the 5' and 3' termini of the antisense strand are modified in their sugar residues, and the ribonucleotides at the 5' and 3' termini of the sense strand are unmodified in their sugar residues. The presently most preferred such compound is TG_HMRG1. The antisense strand of TG_HMRG1 has SEQ ID NO: 22 and the sense strand has SEQ ID NO: 4. Other preferred compounds are TG_HMG1 and TG_HM1, which have the antisense strand represented by SEQ ID NOS: 23 and 25 respectively and the sense strand represented by SEQ ID NO: 5 and 7 respectively.

In one aspect of the invention the oligonucleotide comprises a double-stranded structure, whereby such double-stranded structure comprises
    a first strand and a second strand, whereby
        the first strand comprises a first stretch of contiguous nucleotides and the second strand comprises a second stretch of contiguous nucleotides, whereby
        the first stretches either complementary or identical to a nucleic acid sequence coding for TGaseII and whereby the second stretch is either identical or complementary to a nucleic acid sequence coding for TGaseII.

In an embodiment the first stretch and/or the second stretch comprises from about 14 to 40 nucleotides, preferably about 18 to 30 nucleotides, more preferably from about 19 to 27 nucleotides and most preferably from about 19 to 23 nucleotides, in particular from about 19 to 21 nucleotides. In such an aspect the oligonucleotide may be from 17-40 nucleotides in length.

Additionally, further nucleic acids according to the present invention comprise at least 14 contiguous nucleotides of any one of the SEQ. ID. NO. 3 to SEQ ID NO: 416 and more preferably 14 contiguous nucleotide base pairs at any end of the double-stranded structure comprised of the first stretch and second stretch as described above.

The term "treatment" as used herein refers to administration of a therapeutic substance effective to ameliorate symptoms associated with a disease or condition, to lessen the severity or cure the disease or condition, or to prevent the disease or condition from occurring.

In a particular embodiment, the administration comprises intravenous administration. In another particular embodiment the administration comprises topical or local administration.

Additionally, the present invention provides a method of regulating a pathology or disease (as recited above) in a patient in need of such treatment by administering to a patient a therapeutically effective dose of at least one antisense (AS) oligonucleotide or at least one siRNA against the nucleic acid sequences or a dominant negative peptide directed against the TGaseII sequences or TGaseII proteins or an antibody directed against the TGaseII polypeptide.

Delivery: Delivery systems aimed specifically at the enhanced and improved delivery of siRNA into mammalian cells have been developed, see, for example, Shen et al (FEBS letters 539: 111-114 (2003)), Xia et al., Nature Biotechnology 20: 1006-1010 (2002), Reich et al., Molecular Vision 9: 210-216 (2003), Sorensen et al. (J. Mol. Biol. 327: 761-766 (2003), Lewis et al., Nature Genetics 32: 107-108 (2002) and Simeoni et al., Nucleic Acids Research 31, 11: 2717-2724 (2003). siRNA has recently been successfully used for inhibition in primates; for further details see Tolentino et al., Retina 24(1) February 2004 I 132-138. Respiratory formulations for siRNA are described in U.S. patent application No. 2004/0063654 of Davis et al. Cholesterol-conjugated siRNAs (and other steroid and lipid conjugated siRNAs) can been used for delivery (see Soutschek et al Nature 432: 173-177 (2004) *Therapeutic silencing of an endogenous gene by systemic administration of modified siRNAs*; and Lorenz et al. Bioorg. Med. Chemistry. Lett. 14:4975-4977 (2004) *Steroid* and lipid conjugates of siRNAs to enhance cellular uptake and gene silencing in liver cells.

The siRNAs or pharmaceutical compositions of the present invention are administered and dosed in accordance with good medical practice, taking into account the clinical condition of the individual patient, the disease to be treated, the site and method of administration, scheduling of administration, patient age, sex, body weight and other factors known to medical practitioners.

The "therapeutically effective dose" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art. The compounds of the present invention can be administered by any of the conventional routes of administration. It should be noted that the compound can be administered as the compound or as pharmaceutically acceptable salt and can be administered alone or as an active ingredient in combination with pharmaceutically acceptable carriers, solvents, diluents, excipients, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. Liquid forms may be prepared for injection, the term including subcutaneous, transdermal, intravenous, intramuscular, intrathecal, and other parental routes of administration. The liquid compositions include aqueous solutions, with and without organic cosolvents, aqueous or oil suspensions, emulsions with edible oils, as well as similar pharmaceutical vehicles. In addition, under certain circumstances the compositions for use in the novel treatments of the present invention may be formed as aerosols, for intranasal and like administration. The patient being treated is a warm-blooded animal and, in particular, mammals including man. The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention and they include liposomes and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art. In one specific embodiment of this invention topical and transdermal formulations are particularly preferred.

In general, the active dose of compound for humans is in the range of from 1 ng/kg to about 20-100 mg/kg body weight per day, preferably about 0.01 mg to about 2-10 mg/kg body weight per day, in a regimen of one dose per day or twice or three or more times per day for a period of 1-4 weeks or longer. Treatment for many years or even lifetime treatment is also envisaged for some of the indications disclosed herein.

The present invention also provides for a process of preparing a pharmaceutical composition, which comprises:
  obtaining at least one double stranded siRNA compound of the invention; and
  admixing said compound with a pharmaceutically acceptable carrier.

The present invention also provides for a process of preparing a pharmaceutical composition, which comprises admixing a compound of the present invention with a pharmaceutically acceptable carrier.

In a preferred embodiment, the compound used in the preparation of a pharmaceutical composition is admixed with a carrier in a pharmaceutically effective dose. In a particular embodiment the compound of the present invention is conjugated to a steroid or to a lipid or to another suitable molecule e.g. to cholesterol.

Modifications or analogs of nucleotides can be introduced to improve the therapeutic properties of the nucleotides. Improved properties include increased nuclease resistance and/or increased ability to permeate cell membranes.

Accordingly, the present invention also includes all analogs of, or modifications to, a oligonucleotide of the invention that does not substantially affect the function of the polynucleotide or oligonucleotide. In a preferred embodiment such modification is related to the base moiety of the nucleotide, to the sugar moiety of the nucleotide and/or to the phosphate moiety of the nucleotide.

In embodiments of the invention, the nucleotides can be selected from naturally occurring or synthetically modified bases. Naturally occurring bases include adenine, guanine, cytosine, thymine and uracil. Modified bases of the oligonucleotides include inosine, xanthine, hypoxanthine, 2-aminoadenine, (1-methyl-, 2-propyl- and other alkyl-adenines, 5-halo uracil, 5-halo cytosine, 6-aza cytosine and 6-aza thymine, pseudo uracil, 4-thiuracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl in guanine and other substituted guanines, other aza and deaza adenines, other aza and deaza guanines, 5-trifluoromethyl uracil and 5-trifluoro cytosine.

In addition, analogs of nucleotides can be prepared wherein the structures of the nucleotides are fundamentally altered and are better suited as therapeutic or experimental reagents. An example of a nucleotide analog is a peptide nucleic acid (PNA) wherein the deoxyribose (or ribose) phosphate backbone in DNA (or RNA) is replaced with a polyamide backbone similar to that found in peptides. PNA analogs have been shown to be resistant to degradation by enzymes and to have extended lives in vivo and in vitro. Further. PNAs have been shown to bind more strongly to a complementary DNA sequence than to a DNA molecule. This observation is attributed to the lack of charge repulsion between the PNA strand and the DNA strand. Other modifications that can be made to oligonucleotides include polymer backbones, cyclic backbones, or acyclic backbones.

In one embodiment the modification is a modification of the phosphate moiety, whereby the modified phosphate moiety is selected from the group comprising phosphothioate.

The compounds of the present invention can be synthesized by any of the methods that are well-known in the art for synthesis of ribonucleic (or deoxyribonucleic) oligonucleotides. Such synthesis is, among others, described in Beaucage S. L. and Iyer R. P., Tetrahedron 1992; 48: 2223-2311, Beaucage S. L. and Iyer R. P., Tetrahedron 1993; 49: 6123-6194 and Caruthers M. H. et. al., Methods Enzymol. 1987; 154: 287-313, the synthesis of thioates is, among others, described in Eckstein F., Annu. Rev. Biochem. 1985; 54: 367-402, the synthesis of RNA molecules is described in Sproat B., in Humana Press 2005 Edited by Herdewijn P.; Kap. 2: 17-31 and respective downstream processes are, among others, described in Pingoud A. et. al., in IRL Press 1989 Edited by Oliver R. W A.; Kap. 7: 183-208 and Sproat B., in Humana Press 2005 Edited by Herdewijn P.; Kap. 2: 17-31 (supra).

Other synthetic procedures are known in the art e.g. the procedures as described in Usman et al., 1987, *J. Am. Chem.*

*Soc.*, 109, 7845; Scaringe et al., 1990. *Nucleic Acids Res.*, 18, 5433; Wincott et al, 1995, *Nucleic Acids Res,* 23, 2677-2684; and Wincort et al., 1997, *Methods Mol. Bio.*, 74, 59, and these procedures may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

The oligonucleotides of the present invention can be synthesized separately and joined together post-synthetically, for example, by ligation (Moore et al., 1992, *Science* 256, 9923; Draper et al., International PCT publication No. WO93/23569; Shabarova et al., 1991, *Nucleic Acids Research* 19, 4247; Belton et al., 1997. *Nucleosides & Nucleotides,* 16, 951; Benoit et al., 1997, *Bioconjugate Chem.* 8, 204), or by hybridization following synthesis and/or deprotection.

It is noted that a commercially available machine (available, inter alia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the siRNAs or siRNA fragments of the present invention, two or more such sequences can be synthesized and linked together for use in the present invention.

The compounds of the invention can also be synthesized via a tandem synthesis methodology, as described in US patent application publication No. US2004/0019001 (McSwiggen), wherein both siRNA strands are synthesized as a single contiguous oligonucleotide fragment or strand separated by a cleavable linker which is subsequently cleaved to provide separate siRNA fragments or strands that hybridize and permit purification of the siRNA duplex. The linker can be a polynucleotide linker or a non-nucleotide linker.

The compounds of the present invention can be delivered either directly or with viral or non-viral vectors. When delivered directly the sequences are generally rendered nuclease resistant.

Alternatively the sequences can be incorporated into expression cassettes or constructs such that the sequence is expressed in the cell as discussed herein below. Generally the construct contains the proper regulatory sequence or promoter to allow the sequence to be expressed in the targeted cell. Vectors optionally used for delivery of the compounds of the present invention are commercially available, and may be modified for the purpose of delivery of the compounds of the present invention by methods known to one of skill in the art.

It is also envisaged that a long double stranded oligonucleotide (typically 25-500 nucleotides in length) comprising one or more of the sequences of the oligonucleotides of the invention may be delivered and may be processed intracellularly by endogenous cellular complexes (e.g. by DICER as described above) to produce smaller double stranded oligonucleotides which are oligonucleotides of the invention.

As used herein, the term "polypeptide" refers to, in addition to a polypeptide, an oligopeptide, peptide and a full protein.

Animal model systems: Testing the active siRNAs of the invention may be done in predictive animal models. Several models for kidney fibrosis are described in Example 3.

Two models of liver fibrosis in rats are the Bile Duct Ligation (BDL) with sham operation as controls, and $CCl_4$ poisoning, with olive oil fed animals as controls, as described in the following references: Lotersztajn S, Julien B, Teixeira-Clere F, Grenard P, Mallat A, *Hepatic Fibrosis: Molecular Mechanisms and Drug Targets*. Annu Rev Pharmacol Toxicol. 2004 Oct. 7; Uchio K, Graham M, Dean N M, Rosenbaum J, Desmouliere A., *Down-regulation of connective tissue growth factor and type 1 collagen mRNA expression by connective tissue growth factor antisense oligonucleotide during experimental liver fibrosis*. Wound Repair Regen. 2004 January-February; 12(1):60-6; and Xu X Q, Leow C K, Lu X, Zhang X, Liu J S, Wong W H, Asperger A, Deininger S, Eastwood Leung B C., *Molecular classification of liver cirrhosis in a rat model by proteomics and bioinformatics* Proteomics. 2004 October; 4(10):3235-45.

Models for ocular scarring are well known in the art e.g. Sherwood M B et al., J Glaucoma. 2004 October; 13(5):407-12. *A new model of glaucoma filtering surgery in the rat*; Miller M H et al., Ophthalmic Surg. 1989 May; 20(5):350-7. *Wound healing in an animal model of glaucoma fistulizing surgery in the rabbit*; vanBockxmeer F M et al., Retina. 1985 Fall-Winter; 5(4): 239-52. *Models for assessing scar tissue inhibitors*; Wiedemann P et al., J Pharmacol Methods. 1984 August; 12(1): 69-78. *Proliferative vitreoretinopathy: the rabbit cell injection model for screening of antiproliferative drags*.

Models of cataract are described in the following publications: The role of Src family kinases in cortical cataract formation. Zhou J, Menko A S. Invest Ophthalmol V is Sci. 2002 July; 43(7):2293-300; Bioavailability and anticataract effects of a topical ocular drug delivery system containing disulfiram and hydroxypropyl-beta-cyclodextrin on selenite-treated rats. Wang S, Li D, Ito Y, Nahekura T, Wang S, Zhang J. Wu C. Curr Eye Res. 2004 July; 29(1):51-8; and Long-term organ culture system to study the effects of UV-Airradiation on lens transglutaminase. Weinreb O, Dovrat A.; Carr Eye Res. 2004 July; 29(1):51-8.

Antibody Production

By the term "antibody" as used in the present invention is meant both poly- and mono-clonal complete antibodies as well as fragments thereof, such as Fab, F(ab')2, and Fv, which are capable of binding the epitopic determinant. These antibody fragments retain the ability to selectively bind with its antigen or receptor and are exemplified as follows, inter alia:

(1) Fab, the fragment which contains a monovalent antigen-binding fragment of an antibody molecule can be produced by digestion of whole antibody with the enzyme papain to yield a light chain and a portion of the heavy chain;

(2) (Fab')2, the fragment of the antibody that can be obtained by treating whole antibody with the enzyme pepsin without subsequent reduction; F(ab'2) is a dimer of two Fab fragments held together by two disulfide bonds;

(3) Fv, defined as a genetically engineered fragment containing the variable region of the light chain and the variable region of the heavy chain expressed as two chains; and (4) Single chain antibody (SCA), defined as a genetically engineered molecule containing the variable region of the light chain and the variable region of the heavy chain linked by a suitable polypeptide linker as a genetically fused single chain molecule.

Such fragments having antibody functional activity can be prepared by methods known to those skilled in the art (e.g. Bird et al. (1988) Science 242:423-426)

Conveniently, antibodies may be prepared against the immunogen or portion thereof, for example, a synthetic peptide based on the sequence, or prepared recombinantly by cloning techniques or the natural gene product and/or portions thereof may be isolated and used as the immunogen. Immunogens can be used to produce antibodies by standard antibody production technology well known to those skilled in the art, as described generally in Harlow and Lane (1988), Antibodies: A Laboratory Manual, Cold Spring Harbor Laboratory, Cold Spring Harbor, N.Y., and Bonebaeck (1992), Antibody Engineering—A Practical Guide, W.H. Freeman and Co., NY.

For producing polyclonal antibodies a host, such as a rabbit or goat, is immunized with the immunogen or immunogen fragment, generally with an adjuvant and, if necessary, coupled to a carrier; antibodies to the immunogen are collected from the sera. Further, the polyclonal antibody can be absorbed such that it is monospecific; that is, the sera can be absorbed against related immunogens so that no cross-reactive antibodies remain in the sera, rendering it monospecific.

For producing monoclonal antibodies the technique involves hyperimmunization of an appropriate donor with the immunogen, generally a mouse, and isolation of splenic antibody-producing cells. These cells are fused to an immortal cell, such as a myeloma cell, to provide a fused cell hybrid that is immortal and secretes the required antibody. The cells are then cultured, in bulk, and the monoclonal antibodies harvested from the culture media for use.

For producing recombinant antibody see generally Huston et al. (1991) "Protein engineering of single-chain Fv analogs and fusion proteins" in Methods in Enzymology (J J Langone, ed., Academic Press, New York, N.Y.) 203:46-88; Johnson and Bird (1991) "Construction of single-chain Fat) derivatives of monoclonal antibodies and their production in Escherichia coli in Methods in Enzymology (J J Langone, ed.; Academic Press, New York, N.Y.) 203:88-99; Mernaugh and Mernaugh (1995) "An overview of phage-displayed recombinant antibodies" in Molecular Methods In Plant Pathology (R P Singh and U S Singh, eds.; CRC Press Inc., Boca Raton, Fla.:359-365). In particular scFv antibodies are described in WO 2004/007553 (Tedesco and Marzari). Additionally, messenger RNAs from antibody-producing B-lymphocytes of animals, or hybridoma can be reverse-transcribed to obtain complementary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

The antibody can be bound to a solid support substrate or conjugated with a detectable moiety or in be both bound and conjugated as is well known in the art. (For a general discussion of conjugation of fluorescent or enzymatic moieties see Johnstone & Thorpe (1982.), Immunochemistry in Practice, Blackwell Scientific Publications, Oxford). The binding of antibodies to a solid support substrate is also well known in the art (for a general discussion, see Harlow & Lane (1988) Antibodies: A Laboratory Manual, Cold Spring Harbor Laboratory Publications, New York; and Borrebaeck (1992), Antibody Engineering—A Practical Guide, W.H. Freeman and Co.). The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{14}C$ and iodination.

Additional compounds which are also considered to be useful in the treatment of the diseases and disorders discussed herein may be antisense DNA molecules (which can be generated using the sequence in FIG. 1 by methods known in the art), catalytic RNAs such as ribozymes, polypeptides such as dominant negative peptides (which can be generated using the sequence in FIG. 2 by methods known in the art) or other polypeptide inhibitors. Antisense DNA molecules which comprise the siRNA sequences disclosed herein (with the appropriate nucleic acid modifications stemming from the differences between DNA and RNA) are particularly desirable and may be used in the same capacity as their corresponding siRNAs for all uses and methods disclosed herein.

Screening of TGase Inactivating Compounds

Some of the compounds and compositions of the present invention may be used in a screening assay for identifying and isolating compounds that modulate the activity of TGaseII, in particular compounds that modulate fibrotic disease or fibrosis-related pathology. The compounds to be screened comprise inter cilia substances such as small chemical molecules, antibodies especially neutralizing antibodies, inhibitory polypeptides and dominant negative peptides.

The inhibitory activity of the compounds of the present invention on TGaseII polypeptide enzymatic activity or binding of the compounds of the present invention to TGaseII may be used to determine the interaction of an additional compound with the TGaseII polypeptide, e.g., if the additional compound competes with the antibodies or dominant-negative peptides of the present invention for TGaseII inhibition, or if the additional compound rescues said inhibition. The inhibition or activation can be tested by various means, such as, inter alia, assaying for the product of the activity of the TGaseII polypeptide or displacement of binding compound from the TGaseII polypeptide in radioactive or fluorescent competition assays.

The present invention additionally provides for a process of obtaining a compound capable of inhibiting the enzymatic activity of a TGaseII polypeptide, preferably a human TGaseII polypeptide, that comprises the steps of:
  (i) contacting the TGaseII polypeptide or cells expressing the TGaseII polypeptide with the compound, a lysyl donor and with a glutamyl donor which is a biological molecule;
  (ii) removing excess lysyl donor from the mixture of step (i);
  (iii) measuring the amount of the lysyl-glutamyl crosslinked material produced in the presence of the compound;
  (iv) comparing the amount of lysyl-glutamyl crosslinked material measured in step (iii) to that measured in the absence of the compound under controlled conditions, wherein a decrease in the amount of lysyl-glutamyl crosslinked material is indicative of inhibition of the TGaseII polypeptide activity by the compound; and
  (v) identifying the compound as an inhibitor of TGaseII polypeptide activity.

In one embodiment of all the processes described herein, the TGaseII polypeptide used in such process comprises consecutive amino acids, the sequence of which is set forth in SEQ ID NO: 2.

In another embodiment, the lysyl donor of step (i) is tagged and the measurement in step (iii) is of the tag related read-out, and wherein, a decrease in the read-out level is indicative of inhibition of the TGaseII polypeptide activity by the compound.

The glutamyl donor which is a biological molecule may be e.g. fibronectin, or collagen.

In another embodiment the lysyl donor used in such process is cadaverin tagged with a dansyl fluorescent tag.

In another embodiment the lysyl donor used in such process tagged with biotin, and in a specific embodiment, the lysyl donor is biotin cadaverine. Biotin is detected by streptavidin (or a modified streptavidin such as nutravidin) conjugated to readouts known in the art (e.g. conjugated to horseradish peroxidase, wherein the amount of horseradish peroxidase is quantified using tetramethylbenzidine as a substrate).

In yet another embodiment of the invention, the glutamyl donor in the provided process may be an extra-cellular matrix protein or a cellular protein. The extra cellular matrix protein is selected from the group consisting of: fibronectin, collagen, osteonectin, ECM-gel (e.g. Sigma E-1270), and the intracellular protein is selected inter alia from the group consisting of RhoA, fialmin, spectrin, vimentin, HSP90, HSP60, (see Orru S, Caputo I, D'Amato A, Ruoppolo M, Esposito C *Proteomics identification of acyl-receptor and acyl-donor substrates for transglutaminase in a human intestinal epithelial cell line. Implications for celiac disease*, J Biol Chem. 2003 Aug. 22; 278(34):31766-73).

In a different embodiment, the compound is contacted with cells expressing the TGaseII polypeptide. The cells that may be used in such process may either be separated or present in a tissue. The cells may express the TGaseII polypeptide naturally or as a result of having been transfected with TGaseII gene, either transiently or stably or may over-express the TGaseII gene and the activity of TGaseII will be compared between over-expressors to normal TGaseII expressing cells. In a further embodiment, the glutamyl donor is either a natural product of the cells or it is added from outside.

In a different embodiment, the TGaseII polypeptide is contacted with the compound. The TGaseII polypeptide can be either immobilized or free in a solution. In an embodiment of the provided screening process the glutamyl donor is immobilized.

In a further embodiment, the processes provided for obtaining a compound capable of inhibiting the activity of human TGaseII may comprise a further step in which prior to step (i) TGaseII is contacted with a second compound known to bind TGaseII.

In one embodiment of the invention, the tag read-out in the provided processes described herein is the interaction of biotin with neutravidin conjugated to horseradish peroxidase, wherein the amount of cell-bound horseradish peroxidase is quantified using TMB (tetramethylbenzidine) as a substrate.

In yet a further embodiment, the compound obtained by the provided process inhibits the activity of the TGaseII polypeptide at least 2-fold more effectively than it inhibits the activity of at least one other member of the TGase family, and more preferably the inhibition is at least 10-fold, 50-fold and even 100-fold more effective. In such process, either the TGaseII polypeptide or the second compound may be immobilized.

In one another embodiment, the compound obtained by any of the provided processes is an antibody.

The invention further provides a process of obtaining a compound which modulates the activity of a TGaseII polypeptide, preferably a human TGaseII polypeptide, which comprises the steps of:
 (i) contacting the TGaseII polypeptide with an interactor with which the TGaseII polypeptide interacts specifically in vivo;
 (ii) contacting the TGaseII polypeptide or the interactor with said compound; and
 (iii) measuring the effect of the compound on the interaction between TGaseII polypeptide and the interactor by measuring a parameter related to fibrosis; and
 (iv) comparing the effect measured in step (iii) with the effect measured in the absence of the compound, a change in the effect measured indicating that the compound modulates the activity of the human TGaseII polypeptide.

In one embodiment of the invention the compound obtained by the provided process inhibits the in activity of a human TGaseII polypeptide.

In another embodiment of the invention the TGaseII polypeptide in such process comprises consecutive amino acids, the sequence of which is set forth in SEQ ID NO: 2. In a further embodiment either the TGaseII polypeptide or the interactor are immobilized.

In a further embodiment of the invention, the parameter measured in any of the provided processes is related to a pathology characterized by TGaseII up-regulation in general and to fibrosis related pathologies as defined above, and also to cataract, cardiovascular diseases, neurological disorders, polyglutamine diseases including Huntington's disease (HD), spinobulbar muscular atrophy, dentatorubral-pallidoluysian atrophy and spinocerebellar ataxias (SCAs) 1, 2, 3, 6, 7 and 17), Alzheimer's and Parkinson's disease, coeliac disease and osteoarthritis. It is another 21) object of the present invention to provide a process of obtaining a compound capable of inhibiting the activity of a human TGaseII polypeptide that comprises the steps of:
 (i) contacting the TGaseII polypeptide or cells expressing the TGaseII polypeptide with a plurality of compounds, a tagged lysyl donor and with a glutamyl donor which is a biological molecule;
 (ii) washing excess tagged lysyl donor from the mixture of step (i); and
 (iii) measuring the tag related read-out in the presence of the plurality of compounds;
 (iv) comparing the tag read-out measured in step (iii) to that measured in the absence of the plurality of compounds under controlled conditions, wherein a decrease in the read-out level is indicative of inhibition of the TGaseII polypeptide activity by the plurality of compounds;
 (v) separately determining which compound or compounds present in the plurality inhibit the activity of a human TGaseII.

It is another aspect of the present invention to provide a cell-based process of obtaining a compound capable of inhibiting the activity of a TGaseII polypeptide, preferably human TGaseII polypeptide, that comprises the steps of:
 (i) contacting cells expressing active TGaseII polypeptide with the compound and with a lysyl donor;
 (ii) removing excess lysyl donor from the mixture of step (i);
 (iii) measuring the amount of lysyl-glutamyl crosslinked material produced in the presence of the compound;
 (iv) comparing the amount of lysyl-glutamyl crosslinked material measured in step (iii) to that measured in the absence of the compound under controlled conditions, wherein a decrease in the amount of lysyl-glutamyl crosslinked material is indicative of inhibition of the TGaseII polypeptide activity by the compound; and
 (v) identifying the compound as an inhibitor of TGaseII polypeptide It is another aspect of the present invention to provide a cell-based process of obtaining a compound capable of inhibiting the activity of a human TGaseII polypeptide that comprises the steps of
 a. contacting cells expressing the TGaseII polypeptide with a plurality of compounds and with a lysyl donor;
 b. removing excess lysyl donor from the mixture of step (i); and
 c. measuring the amount of the lysyl-glutamyl crosslinked material produced in the presence of the plurality of compounds;

d. comparing the amount of lysyl-glutamyl crosslinked material measured in step (iii) to that measured in the absence of the plurality of compounds under controlled conditions, wherein a decrease in the amount of lysyl-glutamyl crosslinked material is indicative of inhibition of the TGaseII polypeptide activity by the plurality of compounds; and (e) separately determining which compound or compounds present in the plurality inhibit the activity of a human TGaseII.

Methods

General Methods in Molecular Biology

Standard molecular biology techniques known in the art and not specifically described were generally followed as in Sambrook et al., Molecular Cloning: A Laboratory Manual, Cold Spring Harbor Laboratory Press, New York (1989), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In situ (in cell) PCR in combination with How Cytometry can be used for detection of cells containing specific DNA and mRNA sequences (e.g. Testoni et al., 1996, Blood 87:3822.) Methods of performing RT-PCR are also well known in the art.

The present invention is illustrated in detail below with reference to Examples, but is not to be construed as being limited thereto.

EXAMPLES

Example 1

Design of Active siRNA Compounds

Using proprietary algorithms and the known sequence of cDNA of TGaseII (SEQ ID NO:1), the sequences of many potential siRNAs were generated. These are shown in the Tables below. Note that the abbreviations for species are: H: human; M: mouse; R: rat; G: guinea pig; C: cow.

Table A shows 18 siRNAs that have so far been chemically synthesized and tested for activity (see Example 2). All these siRNAs are 19-mers. In Table A the sense strands of siRNAs 1-18 have SEQ ID NOS: 3-20 respectively, and the antisense strands of siRNAs 1-18 have SEQ ID NOS: 21-38 respectively.

Table B below shows 153 additional 19-mer siRNAs, which have been generated by the proprietary algorithms but not yet tested for activity. In Table B, the sense strands of siRNAs 1-153 have SEQ ID NOS: 39-191, respectively, and the antisense strands of siRNAs 1-153 have SEQ ID NOS: 192-344 respectively.

Table C below shows 36 additional 21-mer siRNAs that have been generated by the proprietary algorithms. In Table C, the sense strands of siRNAs 1-36 have SEQ ID NOS: 345-380 respectively, and the antisense strands of siRNAs 1-36 have SEQ ID NOS: 381-416, respectively.

TABLE A

| No. | name | Sense strand | Antisense strand | Species | NM_198951 (human) | NM_009373 (mouse) | NM1_98851 (RAT) | M19646.1 (GP) |
|---|---|---|---|---|---|---|---|---|
| 1 | TG_HMR1 | ACAAGAGCGAGAUGAUCUG | CAGAUCAUCUCGCUCUUGU | hum_mus_rat | [1077-1095] | [1069-1087] | [1033-1051] | |
| 2 | TG_HMRG1 | AGAGCGAGAUGAUCUGGAA | UUCCAGAUCAUCUCGCUCU | hum_mus_rat_GP | [1080-1098] | [1072-1090] | [1036-1054] | [1048-1066] |
| 3 | TG_HMG1 | ACCCCAAGUUCCUGAAGAA | UUCUUCAGGAACUUGGGGU | hum_mus_GP | [699-717] | [691-709] | | [667-685] |
| 4 | TG_HMG2 | GCGAGAUGAUCUGGAACUU | AAGUUCCAGAUCAUCUCGC | hum_mus_GP | [1083-1101] | [1075-1093] | | [1051-1069] |
| 5 | TG_HM1 | CAAAUCCAUCAACCGUUCC | GGAACGGUUGAUGGAUUUG | hum_mus | [1339-1357] | [1331-1349] | | |
| 6 | TG_M1 | GAACAUCCAUGAGAAACUU | AAGUUUCUCAUGGAUGUUC | mus | | 2599-2617 | | |
| 7 | TG_M2 | CGACCUAUGCCAAGAGAAA | UCUCUCUUGGCAUAGGUCG | mus | | 164-182 | | |
| 8 | TG_M3 | GGUGUGAUUUGGAGAUUCA | UGAAUCUCCAAAUCACACC | mus | | 118-136 | | |
| 9 | TG_M4 | CCAACCACCUGAACAAACU | AGUUUGUUCAGGUGGUUGG | mus_rat | | [1468-1486] | [1432-1450] | |
| 10 | TG_M5 | GAACAAACUGGCAGAGAAA | UUUCUCUGCCAGUUUGUUC | mus_rat | | [1478-1496] | [1442-1460] | |
| 11 | TG_M6 | GCUCUGUCAAGUUCAUCAA | GUGAUGAACUUGACAGAGC | mus_rat | | 601-619 | | |
| 12 | TG_M7 | GAUCCCUACUCUGAGAACA | UGUUCUCAGAGUAGGGAUC | mus_rat | | 1692-1637 | | |
| 13 | TG_M8 | CCAGAGUGGUGACCAACUA | UAGOUGGUCACCACUCUGG | mus_rat | | [976-994] | [940-958] | |
| 14 | TG_M9 | GCAACAAGAGCGAGAUGAU | AUCAUCUCGCUCUUGUUGC | mus_rat | | [1066-1084] | [1030-1048] | |
| 15 | TG_M10 | GCAACCUGCUCAUCGAGUA | UACUCGAUGAGCAGGUUGC | mus_rat | | [1018-1036] | [982-1000] | |

TABLE A-continued

| No. | name | Sense strand | Antisense strand | Species | NM_198951 (human) | NM_009373 (mouse) | NM1_98851 (RAT) | M19646.1 (GP) |
|---|---|---|---|---|---|---|---|---|
| 16 | TG_H1 | GUGACCUAACCACUUAGCA | UGCUAAGUGGUUAGGUCAC | hum | 1773-1791 | | | |
| 17 | TG_H2 | GUAGUGACCUAACCACUUA | UAAGUGGUCAGGUCACUAC | hum | 1770-1788 | | | |
| 18 | TG_HG1 | GACGCUGGGACAACAACUA | UAGUUGUUGUCCCAGCGUC | hum_GP | [816-834] | | | [784-802] |

TABLE B

| No. | Method | Sense siRNA | AntiSense siRNA | human GI 39777598 | Mouse GI 31543859 | Rat GI 42476286 | Guinea-pig GI 387604 | Cow GI 31343554 | species |
|---|---|---|---|---|---|---|---|---|---|
| 1 | Cross Sp | UUCCACUGCUGGGUGGAGU | ACUCCACCCAGCAGUGGAA | 1100-1118 | 1092-1110 | 1056-1074 | 1068-1086 | 1046-1064 | hmrgc |
| 2 | Cross Sp | AAGAGCGAGAUGAUCUGGA | UCCAGAUCAUCUCGCUCUU | 1079-1097 | 1071-1089 | 1035-1053 | 1047-1065 | 1025-1043 | hmrgc |
| 3 | Cross Sp | CAAGAGCGAGAUGAUCUGG | CCAGAUCAUCUCGCUCUUG | 1078-1096 | 1070-1088 | 1034-1052 | 1046-1064 | 1024-1042 | hmrgc |
| 4 | Cross Sp | AACCACCUGAACAAACUGG | CCAGUUUGUOCAGGUGGUU | 1478-1496 | 1470-1488 | 1434-1452 | — | 1424-1442 | hmr |
| 5 | Cross Sp | ACCACCUGAACAAACUGGC | GCCAGUUUGUUCAGGUGGU | 1479-1497 | 1471-1489 | 1435-1453 | — | 1425-1442 | hmr |
| 6 | Cross Sp | CUGGAACUUCCACUGCUGG | CCAGCAGUGGAAGUUCCAG | 1093-1111 | 1085-1103 | 1049-1067 | 1061-1079 | 1039-1057 | hm |
| 7 | Cross Sp | AACUUCCACUGCUGGGUGG | CCACCCAGCAGUGGAAGUU | 1097-1115 | 1089-1107 | 1056-1071 | 1065-1083 | 1043-1061 | hm |
| 8 | Cross Sp | AGGAGAAGAGCGAAGGGAC | GUCCCUUCGCUCUUCUCCU | 1185-1203 | 1177-1195 | 1141-1156 | — | 1131-1149 | hm |
| 9 | Cross Sp | UGAUCUGGAACUUCCACUG | CAGUGGAAGUUCCAGAUCA | 1089-1107 | 1081-1099 | — | 1057-1075 | 1035-1053 | hm |
| 10 | Cross Sp | GAGCGAGAUGAUCUGGAAC | GUUCCAGAUCAUCUCGCUC | 1081-1099 | 1073-1091 | 1037-1054 | 1049-1067 | 1027-1045 | hm |
| 11 | Cross Sp | UCUGGAACUUCCACUGCUG | CAGCAGUGGAAGUUCCAGA | 1092-1110 | 1084-1102 | 1048-1066 | 1060-1078 | 1038-1056 | hm |
| 12 | Cross Sp | GAUCUGGAACUUCCACUGC | GCAGUGGAAGUUCCAGAUC | 1090-1108 | 1082-1100 | — | 1058-1076 | 1036-1054 | hm |
| 13 | Cross Sp | GAGAUGAUCUGGAACUUCC | GGAAGUUCCAGAUUAUCUC | 1085-1103 | 1077-1095 | 1041-1059 | 1053-1071 | 1031-1049 | hm |
| 14 | Cross Sp | AGCGAGAUGAUCUGGAACU | AGUUCCAGAUCAUCUCGCU | 1082-1100 | 1074-1092 | 1038-1054 | 1050-1068 | 1028-1046 | hm |
| 15 | Cross Sp | AGAUGAUCUGGAACUUCCA | UGGAAGUUCCAGAUCAUCU | 1086-1104 | 1078-1096 | 1042-1060 | 1054-1072 | 1032-1050 | hm |
| 16 | Cross Sp | CCCCAAGUUCCUGAGAAC | GUUCUUCAGGAACUUGGGG | 700-718 | 692-710 | 656-671 | 668-685 | 649-659 | hm |
| 17 | Cross Sp | AUCUGGAACUUCCACUGCU | AGCAGUGGAAGUUCCAGAU | 1091-1109 | 1083-1101 | — | 1059-1077 | 1037-1055 | hm |
| 18 | Cross Sp | AGCUUUGUGCUGGGCCACU | AGUGGCCCAGCACAAAGCU | 485-503 | 477-495 | — | — | — | hm |
| 19 | Cross Sp | AACCCCAAGUUCCUGAAGA | UCUUCAGGAACUUGGGGUU | 698-716 | 690-708 | 654-671 | 666-684 | 644-659 | hm |
| 20 | Cross Sp | CAGGAGAAGAGCGAAGGGA | UCCCUUCGCUCUUCUCCUG | 1184-1202 | 1176-1194 | 1140-1156 | 1152-1170 | 1130-1148 | hm |
| 21 | Cross Sp | UUGUGCUGGGCCACUUCAU | AUGAAGUGGCCCAGCACAA | 489-507 | 481-499 | — | 462-475 | — | hm |

TABLE B-continued

| No. | Method | Sense siRNA | AntiSense siRNA | human GI 39777598 | Mouse GI 31543859 | Rat GI 42476286 | Guinea-pig GI 387604 | Cow GI 31343554 | species |
|---|---|---|---|---|---|---|---|---|---|
| 22 | Cross Sp | GAACUUCCACUGCUGGGUG | CACCCAGCAGUGGAAGUUC | 1096-1114 | 1088-1106 | 1056-1070 | 1064-1082 | 1042-1060 | hm |
| 23 | Cross Sp | GGAACUUCCACUGCUGGGU | ACCCAGCAGUGGAAGUUCC | 1095-1113 | 1087-1105 | 1051-1069 | 1063-1081 | 1041-1059 | hm |
| 24 | Cross Sp | ACUUCCACUGCUGGGUGGA | UCCACCCAGCAGUGGAAGU | 1098-1116 | 1090-1108 | 1056-1072 | 1066-1084 | 1044-1062 | hm |
| 25 | Cross Sp | CGAGAUGAUCUGGAACUUC | GAAGUUCCAGAUCAUCUCG | 1084-1102 | 1076-1094 | 1040-1054 | 1052-1070 | 1030-1048 | hm |
| 26 | Cross Sp | AUGAUCUGGAACUUCCACU | AGUGGAAGUUCCAGAUCAU | 1088-1106 | 1080-1098 | 1044-1062 | 1056-1074 | 1034-1052 | hm |
| 27 | Cross Sp | UUUGUGCUGGGCCACUUCA | UGAAGUGGCCCAGCACAAA | 488-506 | 480-498 | — | 462-474 | — | hm |
| 28 | Cross Sp | GAUGAUCUGGAACUUCCAC | GUGGAAGUUCCAGAUCAUC | 1087-1105 | 1079-1097 | 1043-1061 | 1055-1073 | 1033-1051 | hm |
| 29 | Cross Sp | UGGAACUUCCACUGUGGG | CCCAGCAGUGGAAGUUCCA | 1094-1112 | 1086-1104 | 1050-1068 | 1062-1080 | 1040-1058 | hm |
| 30 | Cross Sp | CUUUGUGCUGGGCCACUUC | GAAGUGGCCCAGCACAAAG | 487-505 | 479-497 | — | 462-473 | — | hm |
| 31 | Cross Sp | GCUUUGUGCUGGGCCACUU | AAGUGGCCCAGCACAAAGC | 486-504 | 478-496 | — | 462-472 | — | hm |
| 32 | Cross Sp | UCAGCACUAAGAGCGUGGG | CCCACGCUCUUAGUGCUGA | 1377-1395 | 1369-1387 | 1333-1351 | — | — | hr |
| 33 | Cross Sp | AGAUCAGCACUAAGAGCGU | ACGCUCUUAGUGCUGAUCU | 1374-1392 | 1366-1381 | 1330-1348 | — | — | hr |
| 34 | Cross Sp | GAAGAUCAGCACUAAGAGC | GCUCUUAGUGCUGAUCUUC | 1372-1390 | 1364-1381 | 1328-1346 | — | 1318-1329 | hr |
| 35 | Cross Sp | GAUCAGCACUAAGAGCGUG | CACGCUCUUAGUGCUGAUC | 1375-1393 | 1367-1381 | 1331-1349 | — | — | hr |
| 36 | Cross Sp | AGUAUGGCCAGUGCUGGGU | ACCCAGCACUGGCCAUACU | 918-936 | 918-928 | 874-892 | 886-904 | 864-882 | hr |
| 37 | Cross Sp | AAGUAUGGCCAGUGCUGGG | CCCAGCACUGGCCAUACUU | 917-935 | — | 873-891 | 885-903 | 863-881 | hr |
| 38 | Cross Sp | AUCAGCACUAAGAGCGUGG | CCACGCUCUUAGUGCUGAU | 1376-1394 | 1368-1386 | 1332-1350 | — | — | hr |
| 39 | Cross Sp | AAGAUCAGCACUAAGAGCG | CGCUCUUAGUGCUGAUCUU | 1373-1391 | 1365-1381 | 1329-1347 | — | 1319-1329 | hr |
| 40 | Cross Sp | GGAUCCUAGACAUCUGCCU | AGGCAGAUGUCUAGGAUCC | 663-681 | — | — | — | 609-627 | hc |
| 41 | Cross Sp | CGCUGGGACAACAACUACG | CGUAGUUGUUGUCCCAGCG | 818-836 | 810-826 | 774-787 | 786-803 | 764-782 | hc |
| 42 | Cross Sp | CUUGGAAUUUUGGGCAGUU | AACUGCCCAAAAUUCCAAG | 636-654 | 628-646 | 592-610 | — | 582-600 | hc |
| 43 | Cross Sp | GUCAACUGCAACGAUGACC | GGUCAUCGUUGCAGUUGAC | 782-800 | 774-792 | 738-756 | 750-760 | 728-746 | hc |
| 44 | Cross Sp | CAAGAACAUACCUUGGAAU | AUUCCAAGGUAUGUUCUUG | 625-643 | — | — | 599-610 | 571-589 | hc |
| 45 | Cross Sp | CUCAUCGAGUACUUCCGCA | UGCGGAAGUACUCGAUGAG | 1034-1052 | 1026-1042 | 990-1006 | 1002-1018 | 980-998 | hc |
| 46 | Cross Sp | GCAUGGUCAACUGCAACGA | UCGUUGCAGUUGACCAUGC | 777-795 | 770-784 | 733-748 | 746-760 | 723-741 | hc |

TABLE B-continued

| No. | Method | Sense siRNA | AntiSense siRNA | human GI 39777598 | Mouse GI 31543859 | Rat GI 42476286 | Guinea-pig GI 387604 | Cow GI 31343554 | species |
|---|---|---|---|---|---|---|---|---|---|
| 47 | Cross Sp | CGGAUGCUGUGUACCUGGA | UCCAGGUACACAGCAUCCG | 534-552 | — | — | — | 480-498 | hc |
| 48 | Cross Sp | CCAUGACCAGAACAGCAAC | GUUGCUGUUCUGGUCAUGG | 1012-1030 | 1008-1022 | 972-986 | 984-998 | 958-976 | hc |
| 49 | Cross Sp | ACAUACCUUGGAAUUUUGG | CCAAAAUUCCAAGGUAUGU | 630-648 | — | — | 599-610 | 576-594 | hc |
| 50 | Cross Sp | UCGAGUACUUCCGCAAUGA | UCAUUGCGGAAGUACUCGA | 1038-1056 | 1030-1048 | 994-1006 | 1006-1018 | 984-1002 | hc |
| 51 | Cross Sp | AUGGUCAACUGCAACGAUG | CAUCGUUGCAGUUGACCAU | 779-797 | 771-789 | 735-753 | 747-760 | 725-743 | hc |
| 52 | Cross Sp | ACCUUGGAAUUUUGGGCAG | CUGCCCAAAAUUCCAAGGU | 634-652 | — | — | — | 580-598 | hc |
| 53 | Cross Sp | CAAGUUCAUCAAGAACAUA | UAUGUUCUUGAUGAACUUG | 616-634 | 608-621 | 572-585 | 584-595 | 562-580 | hc |
| 54 | Cross Sp | UUCAUCAAGAACAUACCUU | AAGGUAUGUUCUUGAUGAA | 620-438 | — | — | — | 566-584 | hc |
| 55 | Cross Sp | AUACCUUGGAAUUUUGGGC | GCCCAAAAUUCCAAGGUAU | 632-650 | — | — | 600-610 | 578-596 | hc |
| 56 | Cross Sp | AGUACUUCCGCAAUGAGUU | AACUCAUUGCGGAAGUACU | 1041-1059 | — | — | — | 987-1005 | hc |
| 57 | Cross Sp | UGGGUGGAGUCUGUGAUGA | UCAUCCACGACUCCACCCA | 1109-1127 | 1101-1119 | 1065-1083 | 1077-1095 | 1055-1073 | hc |
| 58 | Cross Sp | CCCAUGACCAGAACAGCAA | UUGCUGUUCUGGUCAUGGG | 1011-1029 | 1003-1021 | 967-985 | 979-997 | 957-975 | hc |
| 59 | Cross Sp | CCAACUUCAUCAAGAACAU | AUGUUCUUGAUGAACUUGG | 615-633 | 608-621 | 572-585 | 583-595 | 561-579 | hc |
| 60 | Cross Sp | GUCAACCCCAAGUUCCUGA | UCAGGAACUUGGGGUUGAC | 695-713 | 690-705 | 654-669 | 665-681 | 641-659 | hc |
| 61 | Cross Sp | AUCAAGAACAUACCUUGGA | UCCAAGGUAUGUUCUUGAU | 623-641 | — | — | 599-609 | 569-587 | hc |
| 62 | Cross Sp | UGGUCAACUGCAACGAUGA | UCAUCGUUGCAGUUGACCA | 780-798 | 772-790 | 736-754 | 746-760 | 726-744 | hc |
| 63 | Cross Sp | CAUGGUCAACUGCAACGAU | AUCGUUGCAGUUGACCAUG | 778-796 | 770-784 | 734-748 | 746-760 | 724-742 | hC |
| 64 | Cross Sp | UGGAAUUUUGGGCAGUUUG | CAAACUGCCCAAAAUUCCA | 638-656 | 630-646 | 594-612 | — | 584-602 | hc |
| 65 | Cross Sp | ACUGCAACGAUGACAGGGG | CCCUGUCAUCGUUGCAGU | 786-804 | 778-796 | 742-760 | — | 732-750 | hc |
| 66 | Cross Sp | AUCCUAGACAUCUGCCUGA | UCAGGCAGAUGUCUAGGAU | 665-683 | — | — | — | 611-629 | hc |
| 67 | Cross Sp | CAACUGCAACGAUGACCAG | CUGGUCAUCGUUGCAGUUG | 784-802 | — | — | — | 730-748 | hc |
| 68 | Cross Sp | GGAUUUUGGGCAGUUUGA | UCAAACUGCCCAAAAUUCC | 639-657 | 631-646 | 595-613 | 615-625 | 585-603 | hc |
| 69 | Cross Sp | AGCGGAUGCUGUGUACCUG | CAGGUACACAGCAUCCGCU | 532-550 | — | — | 500-511 | 478-496 | hc |
| 70 | Cross Sp | UUUGCCCACAUCACCAACA | UGUUGGUGAUGUGGGCAAA | 1574-1592 | 1566-1577 | 1530-1541 | — | 1520-1538 | hc |
| 71 | Cross Sp | AAGAACAUACCUUGGAAUU | AAUUCCAAGGUAUGUUCUU | 626-644 | — | — | 599-610 | 572-590 | hc |

TABLE B-continued

| No. | Method | Sense siRNA | AntiSense siRNA | human GI 39777598 | Mouse GI 31543859 | Rat GI 42476286 | Guinea-pig GI 387604 | Cow GI 31343554 | species |
|---|---|---|---|---|---|---|---|---|---|
| 72 | Cross Sp | UCCUAGACAUCUGCCUGAU | AUCAGGCAGAUGUCUAGGA | 666-684 | — | — | — | 612-630 | hc |
| 73 | Cross Sp | CGAGUACUUCCGCAAUGAG | CUCAUUGCGGAAGUACUCG | 1039-1057 | 1031-1049 | 995-1006 | 1007-1018 | 985-1003 | hc |
| 74 | Cross Sp | UGUCAACCCCAAGUUCCUG | CAGGAACUUGGGGUUGACA | 694-712 | 690-704 | 654-668 | 665-680 | 640-658 | hc |
| 75 | Cross Sp | GACGUCUUUGCCCACAUCA | UGAUGUGGGCAAAGACGUC | 1568-1586 | 1560-1577 | 1524-1541 | — | 1514-1532 | hc |
| 76 | Cross Sp | GAUGCUGUGUACCUGGACU | AGUCCAGGUACACAGCAUC | 536-554 | — | — | — | 482-500 | hc |
| 77 | Cross Sp | AGAACAUACCUUGGAAUUU | AAAUUCCAAGGUAUGUUCU | 627-645 | — | — | 599-610 | 573-591 | hc |
| 78 | Cross Sp | ACGUCUUUGCCCACAUCAC | GUGAUGGGCAAAGACGU | 1569-1587 | 1561-1577 | 1525-1541 | — | 1515-1533 | hc |
| 79 | Cross Sp | AUCGAGUACUUCCGCAAUG | CAUUGCGGAAGUACUCGAU | 1037-1055 | 1029-1047 | 993-1006 | 1005-1018 | 983-1001 | hc |
| 80 | Cross Sp | AAGUUCAUCAAGAACAUAC | GUAUGUUCUUGAUGAACUU | 617-635 | 609-621 | 573-585 | 585-595 | 563-581 | hC |
| 81 | Cross Sp | UGGAGUCGUGGAUGACCAG | CUGGUCAUCCACGACUCCA | 1113-1131 | 1105-1123 | 1069-1087 | 1081-1099 | 1059-1077 | hc |
| 82 | Cross Sp | GUGACAAGAGCGAGAUGAU | AUCAUCUCGCUCUUGUCAC | 1074-1092 | 1069-1084 | 1033-1048 | 1045-1060 | 1020-1038 | hc |
| 83 | Cross Sp | UCAUCGAGUACUUCCGCAA | UUGCGGAAGUACUCGAUGA | 1035-1053 | 1027-1042 | 991-1006 | 1003-1018 | 981-999 | hc |
| 84 | Cross Sp | GUUCGUGCCAUCAAGGAGG | CCUCCUUGAUGGCACGAAC | 1226-1244 | 1224-1236 | 1188-1200 | 1194-1212 | 1172-1190 | hc |
| 85 | Cross Sp | CAUCAAGAACAUACCUUGG | CCAAGGUAUGUUCUUGAUG | 622-640 | — | — | — | 568-586 | hc |
| 86 | Cross Sp | UACCUUGGAAUUUUGGGCA | UGCCCAAAAUUCCAAGGUA | 633-651 | — | — | — | 579-597 | hc |
| 87 | Cross Sp | GACAAGAGCGAGAUGAUCU | AGAUCAUCUCGCUCUUGUC | 1076-1094 | 1069-1086 | 1033-1050 | 1045-1062 | 1022-1040 | hc |
| 88 | Cross Sp | CGUCUUUGCCCACAUCACC | GGUGAUGUGGGCAAAGACG | 1570-1588 | 1566-1577 | 1530-1541 | - | 1516-1534 | hc |
| 89 | Cross Sp | AUGCUGUGUACCUGGACUC | GAGUCCAGGUACACAGCAU | 537-555 | — | — | — | 483-501 | hc |
| 90 | Cross Sp | UUGGAAUUUUGGGCAGUUU | AAACUGCCCAAAAUUCCAA | 637-655 | 629-646 | 593-611 | - | 583-601 | hc |
| 91 | Cross Sp | GCCAAGUUCAUCAAGAACA | UGUUCUUGAUGAACUUGGC | 614-632 | 608-621 | 572-585 | 582-595 | 560-578 | hc |
| 92 | Cross Sp | AGUUCAUCAAGAACAUACC | GGUAUGUUCUUGAUGAACU | 618-636 | 610-621 | 574-585 | - | 564-582 | hc |
| 93 | Cross Sp | GUCUUUGCCCACAUCACCA | UGGUGAUGUGGGCAAAGAC | 1571-1589 | 1566-1577 | 1530-1541 | - | 1517-1535 | hc |
| 94 | Cross Sp | GGGAUCCUAGACAUCUGCC | GGCAGAUGUCUAGGAUCCC | 662-680 | — | — | - | 608-626 | hc |
| 95 | Cross Sp | GAUCCUAGACAUCUGCCUG | CAGGCAGAUGUCUAGGAUC | 664-682 | — | — | - | 610-628 | hc |
| 96 | Cross Sp | AUGUCAACCCCAAGUUCCU | AGGAACUUGGGGUUGACAU | 693-711 | 690-703 | 649-667 | 665-679 | 639-657 | hc |

TABLE B-continued

| No. | Method | Sense siRNA | AntiSense siRNA | human GI 39777598 | Mouse GI 31543859 | Rat GI 42476286 | Guinea-pig GI 387604 | Cow GI 31343554 | species |
|---|---|---|---|---|---|---|---|---|---|
| 97 | Cross Sp | UCAUCAAGAACAUA CCUUG | CAAGGUAUGUUCUUG AUGA | 621-639 | — | — | - | 567-585 | hc |
| 98 | Cross Sp | UCAAGAACAUACCU UGGAA | UUCCAAGGUAUGUUC UUGA | 624-642 | — | — | 599-610 | 570-588 | hc |
| 99 | Cross Sp | CAUCGAGUACUUCC GCAAU | AUUGCGGAAGUACUC GAUG | 1036-1054 | 1028-1042 | 992-1006 | 1004-1018 | 982-1000 | hc |
| 100 | Cross Sp | GGAUGCUGUGUACC UGGAC | GUCCAGGUACACAGC AUCC | 535-553 | — | — | - | 481-499 | hc |
| 101 | Cross Sp | GAUGUCAACCCCAA GUUCC | GGAACUUGGGGUUGA CAUC | 692-710 | 690-702 | 648-666 | 665-678 | 638-656 | hc |
| 102 | Cross Sp | CAUGACCAGAACAG CAACC | GGUUGCUGUUCUGGU CAUG | 1013-1031 | 1008-1023 | 972-987 | 984-999 | 959-977 | hc |
| 103 | Cross Sp | GCCCAUGACCAGAA CAGCA | UGCUGUUCUGGUCAU GGGC | 1010-1028 | 1002-1020 | 966-984 | 978-996 | 956-974 | hc |
| 104 | Cross Sp | GAACAUACCUUGGA AUUUU | AAAAUUCCAAGGUAU GUUC | 628-646 | — | — | 599-610 | 574-592 | hc |
| 105 | Cross Sp | GUGGAGUCGUGGAU GACCA | UGGUCAUCCACGACU CCAC | 1112-1130 | — | — | 1080-1098 | 1058-1076 | hc |
| 106 | Cross Sp | UCAACUGCAACGAU GACCA | UGGUCAUCGUUGCAG UUGA | 783-801 | — | — | — | 729-747 | hc |
| 107 | Cross Sp | AUUUUGGGCAGUUU GAAGA | UCUUCAAACUGCCCA AAAU | 642-660 | 636-646 | 600-613 | 615-628 | 588-606 | hc |
| 108 | Cross Sp | AACAUACCUUGGAA UUUUG | CAAAAUUCCAAGGUA UGUU | 629-647 | — | — | 599-610 | 575-593 | hc |
| 109 | Cross Sp | UGACAAGAGCGAGA UGAUC | GAUCAUCUCGCUCUU GUCA | 1075-1093 | 1069-1085 | 1033-1049 | 1045-1061 | 1021-1039 | hc |
| 110 | Cross Sp | UUCGUGCCAUCAAG GAGGG | CCCUCCUUGAUGGCA CGAA | 1227-1245 | 1224-1237 | 1188-1201 | 1195-1213 | 1173-1191 | hc |
| 111 | Cross Sp | UCAGCCCCAUGUCC UGGAU | AUCCAGGACAUGGGG CUGA | 846-864 | — | — | 814-832 | 792-810 | hc |
| 112 | Cross Sp | GGUCAACUGCAACG AUGAC | GUCAUCGUUGCAGUU GACC | 781-799 | 773-791 | 737-755 | 749-760 | 727-745 | hc |
| 113 | Cross Sp | AAUUUUGGGCAGUU UGAAG | CUUCAAACUGCCCAA AAUU | 641-659 | 636-646 | 600-613 | 615-627 | 587-605 | hc |
| 114 | Cross Sp | CAGCGGAUGCUGUG UACCU | AGGUACACAGCAUCC GCUG | 531-549 | — | — | 499-511 | 477-495 | hc |
| 115 | Cross Sp | AACUGCAACGAUGA CCAGG | CCUGGUCAUCGUUGC AGUU | 785-803 | — | — | — | 731-749 | hc |
| 116 | Gross Sp | AUGACCAGAACAGC AACCU | AGGUUGCUGUUCUGG UCAU | 1014-1032 | 1008-1024 | 972-988 | 984-1000 | 960-978 | hc |
| 117 | Gross Sp | CAUACCUUGGAAUU UGGG | CCCAAAAUUCCAAGG UAUG | 631-649 | — | — | 599-610 | 577-595 | hc |
| 118 | Cross Sp | CUUUGCCCACAUCA CCAAC | GUUGGUGAUGUGGGC AAAG | 1573-1591 | 1566-1577 | 1530-1541 | — | 1519-1537 | hc |
| 119 | Cross Sp | GAGUACUUCCGCAA UGAGU | ACUCAUUGCGGAAGU ACUC | 1040-1058 | 1032-1050 | 996-1006 | 1008-1018 | 986-1004 | hc |
| 120 | Cross Sp | GGCAUGGUCAACUG CAACG | CGUUGCAGUUGACCA UGCC | 776-794 | 770-784 | 732-748 | 746-760 | 722-740 | hc |
| 121 | Cross Sp | UCUUUGCCCACAUC ACCAA | UUGGUGAUGUGGGCA AAGA | 1572-1590 | 1566-1577 | 1530-1541 | — | 1518-1536 | hc |

TABLE B-continued

| No. | Method | Sense siRNA | AntiSense siRNA | human GI 39777598 | Mouse GI 31543859 | Rat GI 42476286 | Guinea-pig GI 387604 | Cow GI 31343554 | species |
|---|---|---|---|---|---|---|---|---|---|
| 122 | Cross Sp | GAAUUUUGGGCAGUUUGAA | UUCAAACUGCCCAAAAUUC | 640-658 | 636-646 | 600-613 | 615-626 | 586-604 | hc |
| 123 | Cross Sp | CCUUGGAAUUUUGGGCAGU | ACUGCCCAAAAUUCCAAGG | 635-653 | — | — | — | 581-599 | hc |
| 124 | Cross Sp | GUUCAUCAAGAACAUACCU | AGGUAUGUUCUUGAUGAAC | 619-637 | 611-621 | 575-585 | — | 565-583 | hc |
| 125 | Cross Sp | UGUAUCGCCUCAGCCUGGA | UCCAGGCUGAGGCGAUACA | 441-459 | — | 402-415 | 409-427 | 3571-3582 | hg |
| 126 | Cross Sp | GCUCGGCCAAGUUCAUCAA | UUGAUGAACUUGGCCGAGC | 609-627 | 608-619 | 572-583 | 577-595 | 555-573 | hg |
| 127 | Cross Sp | GGCUCGGCCAAGUUCAUCA | UGAUGAACUUGGCCGAGCC | 608-626 | 608-618 | 572-582 | 576-594 | 554-572 | hg |
| 128 | Cross Sp | GGACGCUGGGACAACAACU | AGUUGUUGUCCCAGCGUCC | 815-833 | 810-825 | 774-787 | 783-801 | 764-779 | hg |
| 129 | Cross Sp | GGCAGUUUGAAGAUGGGAU | AUCCCAUCUUCAAACUGCC | 648-666 | — | — | 616-634 | 594-612 | hg |
| 130 | Cross Sp | AGUUUGAAGAUGGGAUCCU | AGGAUCCCAUCUUCAAACU | 651-669 | — | 607-625 | 619-637 | — | hg |
| 131 | Cross Sp | CAGUUUGAAGAUGGGAUCC | GGAUCCCAUCUUCAAACUG | 650-668 | — | — | 618-636 | 596-614 | hg |
| 132 | Cross Sp | AGGGCUCGGCCAAGUUCAU | AUGAACUUGGCCGAGCCCU | 606-624 | — | — | 574-592 | 552-570 | hg |
| 133 | Cross Sp | GCAGUUUGAAGAUGGGAUC | GAUCCCAUCUUCAAACUGC | 649-667 | — | — | 617-635 | 595-613 | hg |
| 134 | Cross Sp | CAACCCCAAGUUCCUGAAG | CUUCAGGAACUUGGGGUUG | 697-715 | 690-707 | 654-671 | 665-683 | 643-659 | hg |
| 135 | Cross Sp | GGGCAGUUUGAAGAUGGGA | UCCCAUCUUCAAACUGCCC | 647-665 | — | 603-621 | 615-633 | 593-611 | hg |
| 136 | Cross Sp | ACGCUGGGACAACAACUAC | GUAGUUGUUGUCCCAGCGU | 817-835 | 810-826 | 774-787 | 785-803 | 764-781 | hg |
| 137 | Cross Sp | UACUGCUGUGGCCCAGUUC | GAACUGGGCCACAGCAGUA | 1205-1223 | 1197-1213 | 1161-1177 | 1173-1191 | 1151-1169 | hg |
| 138 | Single Sp | UUGCCCACAUCACCAACAA | UUGUUGGUGAUGUGGGCAA | 1575-1593 | 1567-1577 | 1531-1541 | — | 1521-1538 | h |
| 139 | Single Sp | CCAAGUACCUGCUCAACCU | AGGUUGAGCAGGUACUUGG | 1677-1695 | — | — | 1660-1672 | — | h |
| 140 | Single Sp | CGGCCAAGUUCAUCAAGAA | UUCUUGAUGAACUUGGCCG | 612-630 | 608-621 | 572-585 | 580-595 | 560-576 | h |
| 141 | Single Sp | CGAUGGGUCUGUGCACAAA | UUUGUGCACAGACCCAUCG | 1324-1342 | 1317-1334 | 1281-1298 | — | — | h |
| 142 | Single Sp | CAGUGACUUUGACGUCUUU | AAAGACGUCAAAGUCACUG | 1558-1576 | — | 1517-1528 | 1535-1553 | — | h |
| 143 | Single Sp | GCAUGAACAUGGGCAGUGA | UCACUGCCCAUGUUCAUGC | 1545-1563 | — | — | 1530-1540 | — | h |
| 144 | Single Sp | CAACUACGAGGCCAGUGUA | UACACUGGCCUCGUAGUUG | 244-262 | 239-250 | — | — | — | h |
| 145 | Single Sp | CAUGGGCAGUGACUUUGAC | GUCAAAGUCACUGCCCAUG | 1552-1570 | — | — | 1530-1547 | — | h |
| 146 | Single Sp | GCCCACAUCACCAACAACA | UGUUGUUGGUGAUGUGGGC | 1577-1595 | — | — | — | 1523-1538 | h |

TABLE B-continued

| No. | Method | Sense siRNA | AntiSense siRNA | human GI 39777598 | Mouse GI 31543859 | Rat GI 42476286 | Guinea-pig GI 387604 | Cow GI 31343554 | species |
|---|---|---|---|---|---|---|---|---|---|
| 147 | Single Sp | CGAACCACCUGAACAAACU | AGUUUGUUCAGGUGGUUCG | 1476-1494 | 1470-1486 | 1434-1450 | — | 1424-1440 | |
| 148 | Single Sp | GGCCCGUUUUCCACUAAGA | UCUUAGUGGAAAACGGGCC | 322-340 | — | — | — | — | h |
| 149 | Single Sp | UGACGUCUUUGCCCACAUC | GAUGUGGGCAAAGACGUCA | 1567-1585 | 1560-1577 | 1523-1541 | — | 1514-1531 | h |
| 150 | Single Sp | GAACAUGGGCAGUGACUUU | AAAGUCACUGCCCAUGUUC | 1549-1567 | — | — | 1530-1544 | — | h |
| 151 | Single Sp | GCAGUGACUUUGACGUCUU | AAGACGUCAAAGUCACUGC | 1557-1575 | — | 1517-1528 | 1534-1552 | — | h |
| 152 | Single Sp | CUGUGUUCCUGGAGCAUUU | AAAUGCUCCAGGAACACAG | 1724-1742 | — | — | — | — | h |
| 153 | Single Sp | CAACCUGGAGCCUUUCUCU | AGAGAAAGGCUCCAGGUUG | 1696-1714 | — | 1105-1115 | — | — | h |

TABLE C

| No. | Method | Sense siRNA | AntiSense siRNA | human 39777598 | mouse 31543859 | rat 42476286 | Guinea-pig 387604 | Cow 31343554 | file |
|---|---|---|---|---|---|---|---|---|---|
| 1 | Single Sp | CUAGACAUCUGCUGAUCCUU | AAGGAUCAGGCAGAUGUCUAG | 668-688 | — | — | — | 614-630 | hmrgc |
| 2 | Single Sp | CAACUGACAACAUGCUAGGUA | UACCUAGCAUGUUGUCAGUUG | 1752-1772 | — | — | — | — | hmrgc |
| 3 | Single Sp | CCAAGUUCAUCAAGAACAUAC | GUAUGUUCUUGAUGAACUUGG | 615-635 | 608-621 | 572-585 | 583-595 | 561-581 | hmrgc |
| 4 | Single Sp | CCUGAUCCUUCUAGAUGUCAA | UUGACAUCUAGAAGGAUCAGG | 679-699 | — | — | — | — | hmrgc |
| 5 | Cross Sp | ACAAGAGCGAGAUGAUCUGGA | UCCAGAUCAUCUCGCUCUUGU | 1077-1097 | 1069-1089 | 1033-1053 | 1045-1065 | 1023-1043 | hmrgc |
| 6 | Single Sp | CAAGAACAUACCUUGGAAUUU | AAAUUCCAAGGUAUGUUCUUG | 625-645 | — | — | 599-610 | 571-591 | hmrgc |
| 7 | Single Sp | CGGCCAAGUUCAUCAAGAACA | UGUUCUUGAUGAACUUGGCCG | 612-632 | 608-621 | 572-585 | 580-595 | 560-578 | hmrgc |
| 8 | Single Sp | CUGUGUUCCUGGAGCAUUUGU | ACAAAUGCUCCAGGAACACAG | 1724-1744 | — | — | — | — | hmrgc |
| 9 | Cross Sp | CAAGAGCGAGAUGAUCUGGAA | UUCCAGAUCAUCUCGCUCUUG | | | | | | hmrgc |
| 10 | Single Sp | CAACUACGAGGCCAGUGUAGA | UCUACACUGGCCUCGUAGUUG | 244-264 | 239-250 | — | — | — | hmrgc |
| 11 | Single Sp | GGCCCGUUUUCCACUAAGAGA | UCUCUUAGUGGAAAACGGGCC | 322-342 | — | — | — | — | hmrgc |
| 12 | Single Sp | GCAACCUUCUCAUCGAGUACU | AGUACUCGAUGAGAAGGUUGC | 1026-1046 | 1018-1038 | 982-1002 | 994-1014 | 972-992 | hmrgc |
| 13 | Cross Sp | CGAGAUGAUCUGGAACUUCCA | UGGAAGUUCCAGAUCAUCUCG | 1084-1104 | 1076-1096 | 1040-1060 | 1052-1072 | 1030-1050 | hm |
| 14 | Cross Sp | ACUUCCACUGCUGGGUGGAGU | ACUCCACCCAGCAGUGGAAGU | 1098-1118 | 1090-1110 | 1056-1074 | 1066-1086 | 1044-1064 | hm |
| 15 | Cross Sp | AACCCCAAGUUCUGAAGAAC | GUUCUUCAGGAACUUGGGUU | 698-718 | 690-710 | 654-671 | 666-685 | 644-659 | hm |

TABLE C-continued

| No. | Method | Sense siRNA | AntiSense siRNA | human 39777598 | mouse 31543859 | rat 42476286 | Guinea-pig 387604 | Cow 31343554 | file |
|---|---|---|---|---|---|---|---|---|---|
| 16 | Cross Sp | AUGAUCUGGAACUUCCACUGC | GCAGUGGAAGUUCCAGAUCAU | 1088-1108 | 1080-1100 | 1044-1064 | 1056-1076 | 1034-1054 | hm |
| 17 | Cross Sp | GAACUUCCACUGCUGGGUGGA | UCCACCCAGCAGUGGAAGUUC | 1096-1116 | 1088-1108 | 1056-1072 | 1064-1084 | 1042-1062 | hm |
| 18 | Cross Sp | UGGAACUUCCACUGCUGGGUG | CACCCAGCAGUGGAAGUUCCA | 1094-1114 | 1086-1106 | 1050-1070 | 1062-1082 | 1040-1060 | hm |
| 19 | Cross Sp | AGCGAGAUGAUCUGGAACUUC | GAAGUUCCAGAUCAUCUCGCU | 1082-1102 | 1074-1094 | 1038-1054 | 1050-1070 | 1028-1048 | hm |
| 20 | Cross Sp | GAUGAUCUGGAACUUCCACUG | CAGUGGAAGUUCCAGAUCAUC | 1087-1107 | 1079-1099 | 1043-1063 | 1055-1075 | 1033-1053 | hm |
| 21 | Cross Sp | AGAGCGAGAUGAUCUGGAACU | AGUUCCAGAUCAUCUCGCUCU | 1080-1100 | 1072-1092 | 1036-1054 | 1048-1068 | 1026-1046 | hm |
| 22 | Cross Sp | CUGGAACUUCCACUGCUGGGU | ACCCAGCAGUGGAAGUUCCAG | 1093-1113 | 1085-1105 | 1049-1069 | 1061-1081 | 1039-1059 | hm |
| 23 | Cross Sp | UGAUCUGGAACUUCCACUGCU | AGCAGUGGAAGUUCCAGAUCA | 1089-1109 | 1081-1101 |  | 1057-1077 | 1035-1055 | hm |
| 24 | Cross Sp | AAGAGCGAGAUGAUCUGGAAC | GUUCCAGAUCAUCUCGCUCUU | 1079-1099 | 1071-1091 | 1035-1054 | 1047-1067 | 1025-1045 | hm |
| 25 | Cross Sp | CAGCUUUGUGCUGGGCCACUU | AAGUGGCCCAGCACAAAGCUG | 484-504 | 476-496 | — | 452-472 | — | hm |
| 26 | Cross Sp | GCUUUGUGCUGGGCCACUUCA | UGAAGUGGCCCAGCACAAAGC | 485-506 | 478-498 | — | 452-474 | — | hm |
| 27 | Cross Sp | AGAUGAUCUGGAACUUCCACU | AGUGGAAGUUCCAGAUCAUCU | 1086-1106 | 1078-1098 | 1042-1062 | 1054-1074 | 1032-1052 | hm |
| 28 | Cross Sp | CUUUGUGCUGGGCCACUUCAG | AUGAAGUGGCCCAGCACAAAG | 487-507 | 479-499 | — | 462-475 | — | hm |
| 29 | Cross Sp | GCGAGAUGAUCUGGAACUUCC | GGAAGUUCCAGAUCAUCUCGC | 1083-1103 | 1075-1095 | 1039-1059 | 1051-1071 | 1029-1049 | hm |
| 30 | Cross Sp | AUCUGGAACUUCCACUGCUGG | CCAGCAGUGGAAGUUCCAGAU | 1091-1111 | 1083-1103 | 1047-1067 | 1059-1079 | 1037-1057 | hm |
| 31 | Cross Sp | UCUGGAACUUCCACUGCUGGG | CCCAGCAGUGGAAGUUCCAGA | 1092-1112 | 1084-1104 | 1048-1068 | 1060-1080 | 1038-1058 | hm |
| 32 | Cross Sp | GAUCUGGAACUUCCACUGCUG | CAGCAGUGGAAGUUCCAGAUC | 1090-1110 | 1082-1102 | 1046-1066 | 1056-1078 | 1036-1056 | hm |
| 33 | Cross Sp | GAGAUGAUCUGGAACUUCCAC | GUGGAAGUUCCAGAUCAUCUC | 1085-1105 | 1077-1097 | 1041-1061 | 1053-1073 | 1031-1051 | hm |
| 34 | Cross Sp | AGCUUUGUGCUGGGCCACUUC | GAAGUGGCCCAGCACAAAGCU | 485-505 | 477-497 | — | 453-473 | — | hm |
| 35 | Cross Sp | GAGCGAGAUGAUCUGGAACUU | AAGUUCCAGAUCAUCUCGCUC | 1081-1101 | 1073-1093 | 1037-1054 | 1049-1069 | 1027-1047 | hm |
| 36 | Cross Sp | AACUUCCACUGCUGGGUGGAG | CUCCACCCAGCAGUGGAAGUU | 1097-1117 | 1089-1109 | 1056-1073 | 1065-1085 | 1043-1063 | hm |

Example 2

Testing the siRNA Compounds for Anti-TGaseII Activity

I. Preparation of Working Solutions of siRNAs (Double-Stranded Oligonucleotides)

Lyophilized oligonucleotides were dissolved in RNAse-free double-distilled water to produce a final concentration of 100 uM. The diluted oligonucleotides were kept at room temperature for 15 min and immediately frozen in liquid nitrogen. The oligonucleotides were stored at −80° C. and diluted before use with PBS.

II. Establishment of NRK49 Cell Line Stably Overexpressing Rat TGaseII

The full length cDNA of rat TGaseII cloned in PLXSN vector (CLONTECH) was used for transfection into a Rat1 fibroblast cell line. Lipofectamine reagent (Invitrogen) was used as the transfection reagent using the protocol described below. 48 hr following transfection, selection of stable clones was performed using G418 antibiotic (neomycin). The stable overexpression of TGaseII in this polyclonal population was verified by Western blotting and TGaseII activity assay. The cells were designated as NRK49-TGaseII (TGASE-OE®).

III Activity Assay for TGaseII in NRK49

$4 \times 10^3$ NRK49-ratTGASE-OE cells were seeded per well in a 96 well plate. TGaseII activity was measured using a cell-based assay for TGaseII activity. Briefly, the growth medium was replaced with cell labeling medium (DMEM in 0.1% BSA, 25 uM BC, 10 uM Calcimycin, 16.2 mM CaCl2) for 45 min at 37° C. 45 min later, the cells were fixed with 4% formaldehyde, treated with 0.6% $H_2O_2$ and stained with Netravidin-HRP Ab in order to test the cross-linking of biotin-labeled cadaverin. The absorbance was read at $\lambda=450$ nm. For normalization, the cells were stained with Hoechst dye solution. The activity of TGaseII is 75 fold higher in NRK49-TGaseII cells compared to NRK49 control cells.

IV. Transfection by siRNA Oligonucleotides Using Lipofectamine2000 Reagent $2 \times 10^5$ cells were seeded per well in 6 well plates. After 24 hrs, the cells were transfected with TGaseII specific siRNA oligonucleotides using Lipofectamine2000 reagent (Invitrogen) according to the following procedure:

1. Before transfection, the cell medium was replaced with 1500 ul of fresh medium without antibiotics.
2. In a sterile plastic tube, Lipofectamine2000 reagent (the amount is calculated according to 5 ul per well) was added to 250 ul of serum-free medium, and incubated for 5 min at room temperature.
3. In another rube, the siRNA oligonucleotides (varying amounts to fit the desired final concentration per well) were added to 250 ul of serum-free medium.
4. Lipofectamine2000 complex was combined with the siRNA solution and incubated for 20 min at room temperature.
5. The resulting mixture was added dropwise to the cells, and the cells were incubated at 37° C. until analysis of siRNA activity.

V. Testing the Activity of Anti TGaseII siRNAs in Transfected Human, Mouse and Rat Cells The activity of TGaseII siRNAs listed in Table A was tested in 3 different cell lines originating from different species:

1. Mouse-specific TGaseII siRNAs were tested in mouse cells, which express mouse TGaseII-NMUMG cells.
2. human-specific TGaseII siRNA were tested in human HeLa cells which express human TgaseII; see FIG. 3.
3. Rat-specific TGaseII siRNAs were tested in NRK49 overexpressing rat TGaseII (TGASE-OE® cells).

48 h to 6 days after transfection of siRNAs, the cells were harvested and expression of TGaseII protein was examined by Western blot analysis with specific antibodies. The decrease in TGaseII polypeptide expression in the cells transfected with siRNA oligonucleotides specific to TGaseII as compared to controls indicated that siRNAs elicited inhibitory effect on TGaseII protein expression, which can be quantified.

Table D below summarizes the information about TGaseII inhibitory activity of each siRNA oligonucleotide. The names of oligonucleotides in Table correspond to the names used in Table A. Note that the comparison is to the activity in each cell line transfected by different siRNAs, and not between cell lines. The presently most preferred human siRNA is TG_H-MRG1, which elicited high TGaseII inhibitory effect and also inhibited mouse, rat and guinea pig in TGaseII. Other preferred human siRNAs are TG_HMG1 and TG_HM1.

TABLE D

| name | Species | Human TGII | Mouse TGII | Rat TGII |
|---|---|---|---|---|
| TG_HMR1 | hum_mus_rat | + | − | + |
| TG_HMRG1 | hum_mus_rat_GP | ++++ | +++ | ++++ |
| TG_HMG1 | hum_mus_GP | ++++ | + | ND |
| TG_HMG2 | hum_mus_GP | ++++(toxic) | ++++(toxic) | ND |
| TG_HM1 | hum_mus | ++++ | + | ND |
| TG_M1 | Mus | + | +++ | ND |
| TG_M2 | Mus | − | +++ | ND |
| TG_M3 | Mus | +++ | ++++ | ND |
| TG_M4 | mus_rat | ND | ++ | ++ |
| TG_M5 | mus_rat | +++ | +++ | +++ |
| TG_M6 | mus_rat | ND | ++ | +++ |
| TG_M7 | mus_rat | ND | ++ | ++++ |
| TG_M8 | mus_rat | ND | ++ | ++ |
| TG_M9 | mus_rat | +++ | +++ | +++ |
| TG_M10 | mus_rat | ND | + | +++ |
| TG_H1 | Hum | − | ND | ND |
| TG_H2 | Hum | − | ND | ND |
| TG_HG1 | hum_GP | ++ | ND | ND |

Example 3

Animal Models of Kidney Fibrosis

Testing of the in vivo therapeutic activity of anti-TGaseII siRNAs, or of neutralizing antibodies against TGaseII or of other TGaseII inhibitors may be done in the following animal models of kidney fibrosis in which disease-associated overexpression of TGaseII was found (as detected by in situ hybridization; see below).

A. Rat Diabetic and Aging Models of Kidney Fibrosis

A1. ZDF Rats

Kidney samples of 9-month-old ZDF rats (Zucker diabetic fatty rats) presented hydronephrotic changes with dilated calyces. Microscopically these samples displayed the features of glomerulosclerosis and tubulointerstitial fibrosis. In accordance with these morphological changes, the expression of fibrosis marker genes (osteopontin (OPN), transforming growth factor β1 (TGF-β1) and procollagen α1(1) (Col1)), as measured by in situ hybridization, was significantly increased compared to normal kidneys. Strong OPN expression was detectable in all tubular structures in both kidney cortex and medulla. TGF-β1 expression was widespread throughout interstitial cells. Some epithelial cells also showed TGF-β1 expression. Col1 expression was detectable by in situ hybridization in most interstitial cells within the medulla, while cortical expression was "focal".

A2. Aged fa/fa (Obese Zucker) Rats

Fa/fa rats are genetically deficient for leptin receptor; and, as a result, develop insulin resistant diabetes (type II diabetes) with progressive diabetic nephropathy, Kidney samples of 12-month-old fa/fa rats presented with high degree glomerulosclerosis and diffuse tubulointerstitial fibrosis throughout both the cortex and the medulla. The pattern of fibrosis marker gene expression corresponded to the morphological changes. OPN was expressed in tubular structures in the cortex and in the medulla. Multiple interstitial cells expressed TGF-β1. Significantly, multiple foci and single interstitial cells showed strong Col1 expression in both cortex and medulla so that the number of Col1-expressing cells appeared to be higher in fa/fa kidney samples than in ZDF samples.

A3. Aged Sprague-Dawley (SD) (Normal) Rats

Kidney samples of aged SD rats also showed increased accumulation of collagen in glomeruli and interstitial space and increased expression of fibrosis marker genes. Significantly, the intensity of fibrotic changes varied among samples. Thus, one of the four samples studied displayed very few changes compared with young animals; in the second sample, fibrotic changes were confined only to "polar" regions, and the remaining two samples displayed uniform accumulation of collagen and elevated expression of marker genes throughout the sections A4. Goto Kakizaki (GK) 48-Week-Old Rats GK rats are an inbred strain derived from Wistar rats, selected for spontaneous development of NIDDM (diabetes type II). Kidney samples from both GK and control Wistar 48-week-old rats showed accumulation of collagen in glomeruli and interstitial space. This accumulation was more pronounced in the GK samples.

TGaseII Hybridization Pattern

TGaseII-specific hybridization signal was associated with fibrotic phenotype (diffuse or focal) in kidneys of both healthy and diabetic rats. Non-fibrotic kidney samples demonstrate a diffuse, low but detectable TGaseII-specific hybridisation signal over proximal tubules. By 12 months of age, a stronger signal is concentrated over interstitial cells and epithelial lining of distended tubules that show clear signs of atrophy. In chronic renal failure sample (kidney from two years old rat), a strong TGaseII expression is visible in tubular profiles lined by atrophic or proliferating epithelium cells within surrounding interstitium. Similarity, ZDF samples showed intensification of the hybridization signal along with the progression of the fibrosis (or aging).

B. Induced Models of Kidney Fibrosis

B1. Permanent Unilateral Ureteral Obstruction (UUO) Model

Unilateral ureteral obstruction (UUO) is a model of acute interstitial fibrosis occurring in healthy non-diabetic animals. Renal fibrosis develops within days following the obstruction.

To produce the model, rats were anaesthetized with Ketamin/Xylazine and the abdominal cavity was opened. After exposure, the right ureter was ligated with a suture at the level of the lower kidney pole. In sham-operated rats, the ureter was exposed but not ligated. The study was terminated at different timepoints following ureteral obstruction (e.g., at 24 hr, 5 days, 10 days, 15 days, 20 days and 25 days), and the kidneys were removed and examined.

Histological examination revealed that permanent UUO results in a rapid activation of collagen synthesis by interstitial cells in both medulla and cortex. By 20-25 days of UUO, significant amounts of interstitial collagen were deposited in the interstitial space, whereas glomerular accumulation of collagen was confined to the outer capsule.

In situ hybridization analysis of obstructed kidney samples indicated rapid and significant changes in the pattern of TGaseII expression dependent on the duration of UUO. After 24 hours of UUO, a very strong hybridization signal was detected over cortical tubular epithelium, whereas medullar epithelial cells showed much weaker signal. At 5 and 10 days of UUO, the "foci" of strong hybridization signal were associated with the areas of developing tubulointerstitial fibrosis where the signal was located to both epithelial and interstitial cells. Similar results were observed in mice exposed to the same UUO model.

B2. 5/6 Nephrectomy

5/6 nephrectomy is another useful animal model for chronic renal insufficiency (CRI) in which fibrosis is evident.

In summary, the results suggest that an increase in TGaseII expression and activity level accompanies fibrotic changes in the kidneys.

Example 4

Establishment of TGaseII Role in Renal Fibrosis Employing the UUO Model Using TGaseII Knock-Out Mice TgaseII knock-out mice were obtained from Dr. Melino (De Laurenzi V. Melino G., *Gene disruption of tissue transglutaminase*, Mol Cell Biol. 2001 January; 21(1):148-55). The mice appeared phenotypically normal. Also no morphological changes were observed in kidneys obtained from these mice.

TGaseII KO mice were then used for the analysis of the development of kidney fibrosis following induction of MO by assessing kidney collagen accumulation compared to normal mice The results clearly demonstrated that disruption of TGaseII results in statistically significant reduced collagen accumulation following both three (3) and seven (7) days of obstruction, as compared to collagen accumulation in obstructed kidneys of wild type mice, thus implicating TGaseII as a functionally important factor in kidney fibrosis. It is thus suggested that inhibition of TGaseII activity may have an anti-fibrotic therapeutic effect.

Example 5

Inhibition of TGaseII Activity Using Monoclonal Neutralizing Antibodies

Recombinant monoclonal human-anti-human antibodies against TGaseII were obtained by screening of a phage display library. 720 clones were screened for binding human TGaseII. Seven (7) clones were selected which showed intense binding to the enzyme. The activity assay demonstrated that these antibodies inhibited the crosslinking activity of human TGaseII enzyme at a range of concentrations (1-5 n M).

What is claimed is:

1. A double-stranded RNA compound having the structure:

5'(N)$_x$—Z3'(antisense strand)

3'Z'—(N')$_y$5'(sense strand)

wherein each of N and N' is a ribonucleotide which may independently be modified or unmodified in its sugar residue;
   wherein each of (N)$_x$ and (N')$_y$ is an oligomer in which each consecutive N or N' is joined to the next N or N' by a covalent bond;
   wherein each of x and y is an integer from 19 to 23;
   wherein each of Z and Z' may be present or absent, but if present is 1-5 consecutive nucleotides covalently attached at the 3' terminus of the strand in which it is present; and
   wherein the sequence of (N)$_x$ comprises a sequence selected from one of the following sequences:

(a) UUCUUCAGGAACUUGGGGU;   (SEQ ID NO: 23)

(b) GGAACGGUUGAUGGAUUUG.   (SEQ ID NO: 25)

2. The compound of claim 1, wherein the antisense strand comprises the sequence UUCUUCAGGAACUUGGGGU (SEQ ID NO: 23) and wherein the sense strand comprises the sequence ACCCCAAGUUCCUGAAGAA (SEQ ID NO: 5).

3. The compound of claim 1, wherein the antisense strand comprises the sequence GGAACGGUUGAUGGAUUUG (SEQ ID NO: 25) and wherein the sense strand comprises the sequence CAAAUCCAUCAACCGUUCC (SEQ ID NO: 7).

4. The compound of claim 1, wherein the covalent bond is a phosphodiester bond.

5. The compound of claim 1, wherein x=y.

6. The compound of claim 5, wherein x=y=19.

7. The compound of claim 1, wherein both Z and Z' are absent.

8. The compound of claim 1, wherein one of Z or Z' is present.

9. The compound of claim 1, wherein all of the ribonucleotides in (N)$_x$ or (N')$_y$ or both are unmodified in their sugar residues.

10. The compound of claim 1, wherein at least one ribonucleotide is modified in its sugar residue.

11. The compound of claim 10, wherein the modification of the sugar residue comprises a modification at the 2' position.

12. The compound of claim 11, wherein the modification at the 2' position of the sugar residue results in the presence of a moiety selected from the group consisting of an amino, a fluoro, an alkoxy and an alkyl group.

13. The compound of claim 12, wherein the moiety comprises an alkoxy group.

14. The compound of claim 13, wherein the alkoxy group is a methoxy (2'-O-methyl).

15. The compound of claim 10, wherein in alternating ribonucleotides in both the antisense strand and the sense strand their sugar residues are modified.

16. The compound of claim 15, wherein each of the modified alternating ribonucleotides is modified at the 2' position of its sugar moiety.

17. The compound of claim 15, wherein each ribonucleotide at the 5' terminus and at the 3' terminus of the antisense strand is modified in its sugar residue, and each ribonucleotide at the 5' terminus and at the 3' terminus of the sense strand is unmodified in its sugar residue.

18. A composition comprising the double-stranded RNA compound of claim 1, and a carrier.

19. The composition of claim 18, wherein the double-stranded RNA compound is present in an amount effective to down-regulate the expression of a human TGase II gene in a cell.

20. A method of treating a patient suffering from a disease or condition selected from an ocular disease especially cataract, a cardiovascular disease especially cardiac hypertrophy, atherosclerosis/restenosis, a neurological disease, including polyglutamine disease, spinobulbar muscular atrophy, dentatorubral-pallidoluysian atrophy, spinocerebellar ataxis (SCAs) 1, 2, 3, 6, 7 and 17, Alzheimer's disease, Parkinson's disease and fibrosis or a fibrotic disease, comprising administering to the patient a composition comprising a double stranded RNA compound having the structure:

$$5'(N)_x - Z3'(\text{antisense strand})$$

$$3'Z' - (N')_y 5'(\text{sense strand})$$

wherein each N and N' is a ribonucleotide which may independently be modified or unmodified in its sugar residue;

wherein each of $(N)_x$ and $(N')_y$ is an oligomer in which each consecutive N or N' is joined to the next N or N' by a covalent bond;

wherein each of x and y is an integer from 19 to 23;

wherein each of z and z' may be present or absent, but if present is 1-5 consecutive nucleotides covalently attached at the 3' terminus of the strand in which it is present;

wherein the sequence of (N), comprises a sequence selected from one of the following sequences:

| | | |
|---|---|---|
| (a) | UUCUUCAGGAACUUGGGGU; | (SEQ ID NO: 23) |
| (b) | GGAACGGUUGAUGGAUUUG; | (SEQ ID NO: 25) |
| (c) | UUCCAGAUCAUCUCGCUCU; | (SEQ ID NO: 22) | and wherein the compound is administered in an amount effective to treat the patient.

* * * * *

SEQUENCE LISTING

```
<160> NUMBER OF SEQ ID NOS: 416

<210> SEQ ID NO 1
<211> LENGTH: 2064
<212> TYPE: DNA
<213> ORGANISM: Homo sapiens
<220> FEATURE:
<221> NAME/KEY: CDS
<222> LOCATION: (1)..(2064)

<400> SEQUENCE: 1
```

```
atg gcc gag gag ctg gtc tta gag agg tgt gat ctg gag ctg gag acc      48
Met Ala Glu Glu Leu Val Leu Glu Arg Cys Asp Leu Glu Leu Glu Thr
1               5                   10                  15 aat ggc cga gac cac cac acg gcc gac ctg tgc cgg gag aag ctg gtg      96
Asn Gly Arg Asp His His Thr Ala Asp Leu Cys Arg Glu Lys Leu Val
            20                  25                  30 gtg cga cgg ggc cag ccc ttc tgg ctg acc ctg cac ttt gag ggc cgc     144
Val Arg Arg Gly Gln Pro Phe Trp Leu Thr Leu His Phe Glu Gly Arg
        35                  40                  45 aac tac gag gcc agt gta gac agt ctc acc ttc agt gtc gtg acc ggc     192
Asn Tyr Glu Ala Ser Val Asp Ser Leu Thr Phe Ser Val Val Thr Gly
    50                  55                  60 cca gcc cct agc cag gag gcc ggg acc aag gcc cgt ttt cca cta aga     240
Pro Ala Pro Ser Gln Glu Ala Gly Thr Lys Ala Arg Phe Pro Leu Arg
65              70                  75                  80 gat gct gtg gag gag ggt gac tgg aca gcc acc gtg gtg gac cag caa     288
Asp Ala Val Glu Glu Gly Asp Trp Thr Ala Thr Val Val Asp Gln Gln
            85                  90                  95 gac tgc acc ctc tcg ctg cag ctc acc acc ccg gcc aac gcc ccc atc     336
Asp Cys Thr Leu Ser Leu Gln Leu Thr Thr Pro Ala Asn Ala Pro Ile
        100                 105                 110 ggc ctg tat cgc ctc agc ctg gag gcc tcc act ggc tac cag gga tcc     384
Gly Leu Tyr Arg Leu Ser Leu Glu Ala Ser Thr Gly Tyr Gln Gly Ser
    115                 120                 125 agc ttt gtg ctg ggc cac ttc att ttg ctc ttc aac gcc tgg tgc cca     432
Ser Phe Val Leu Gly His Phe Ile Leu Leu Phe Asn Ala Trp Cys Pro
130                 135                 140 gcg gat gct gtg tac ctg gac tcg gaa gag gag cgg cag gag tat gtc     480
Ala Asp Ala Val Tyr Leu Asp Ser Glu Glu Glu Arg Gln Glu Tyr Val
145                 150                 155                 160 ctc acc cag cag ggc ttt atc tac cag ggc tcg gcc aag ttc atc aag     528
Leu Thr Gln Gln Gly Phe Ile Tyr Gln Gly Ser Ala Lys Phe Ile Lys
            165                 170                 175 aac ata cct tgg aat ttt ggg cag ttt gaa gat ggg atc cta gac atc     576
Asn Ile Pro Trp Asn Phe Gly Gln Phe Glu Asp Gly Ile Leu Asp Ile
        180                 185                 190 tgc ctg atc ctt cta gat gtc aac ccc aag ttc ctg aag aac gcc ggc     624
Cys Leu Ile Leu Leu Asp Val Asn Pro Lys Phe Leu Lys Asn Ala Gly
    195                 200                 205 cgt gac tgc tcc cgc cgc agc agc ccc gtc tac gtg ggc cgg gtg gtg     672
Arg Asp Cys Ser Arg Arg Ser Ser Pro Val Tyr Val Gly Arg Val Val
210                 215                 220 agt ggc atg gtc aac tgc aac gat gac cag ggt gtg ctg ctg gga cgc     720
Ser Gly Met Val Asn Cys Asn Asp Asp Gln Gly Val Leu Leu Gly Arg
225                 230                 235                 240 tgg gac aac aac tac ggg gac ggc gtc agc ccc atg tcc tgg atc ggc     768
Trp Asp Asn Asn Tyr Gly Asp Gly Val Ser Pro Met Ser Trp Ile Gly
            245                 250                 255 agc gtg gac atc ctg cgg cgc tgg aag aac cac ggc tgc cag cgc gtc     816
Ser Val Asp Ile Leu Arg Arg Trp Lys Asn His Gly Cys Gln Arg Val
        260                 265                 270 aag tat ggc cag tgc tgg gtc ttc gcc gcc gtg gcc tgc aca gtg ctg     864
Lys Tyr Gly Gln Cys Trp Val Phe Ala Ala Val Ala Cys Thr Val Leu
    275                 280                 285 agg tgc ctg ggc atc cct acc cgc gtc gtg acc aac tac aac tcg gcc     912
Arg Cys Leu Gly Ile Pro Thr Arg Val Val Thr Asn Tyr Asn Ser Ala
290                 295                 300 cat gac cag aac agc aac ctt ctc atc gag tac ttc cgc aat gag ttt     960
His Asp Gln Asn Ser Asn Leu Leu Ile Glu Tyr Phe Arg Asn Glu Phe
305                 310                 315                 320
```

```
ggg gag atc cag ggt gac aag agc gag atg atc tgg aac ttc cac tgc    1008
Gly Glu Ile Gln Gly Asp Lys Ser Glu Met Ile Trp Asn Phe His Cys
                325                 330                 335 tgg gtg gag tcg tgg atg acc agg ccg gac ctg cag ccg ggg tac gag    1056
Trp Val Glu Ser Trp Met Thr Arg Pro Asp Leu Gln Pro Gly Tyr Glu
            340                 345                 350 ggc tgg cag gcc ctg gac cca acg ccc cag gag aag agc gaa ggg acg    1104
Gly Trp Gln Ala Leu Asp Pro Thr Pro Gln Glu Lys Ser Glu Gly Thr
        355                 360                 365 tac tgc tgt ggc cca gtt cca gtt cgt gcc atc aag gag ggc gac ctg    1152
Tyr Cys Cys Gly Pro Val Pro Val Arg Ala Ile Lys Glu Gly Asp Leu
    370                 375                 380 agc acc aag tac gat gcg ccc ttt gtc ttt gcg gag gtc aat gcc gac    1200
Ser Thr Lys Tyr Asp Ala Pro Phe Val Phe Ala Glu Val Asn Ala Asp
385                 390                 395                 400 gtg gta gac tgg atc cag cag gac gat ggg tct gtg cac aaa tcc atc    1248
Val Val Asp Trp Ile Gln Gln Asp Asp Gly Ser Val His Lys Ser Ile
                405                 410                 415 aac cgt tcc ctg atc gtt ggg ctg aag atc agc act aag agc gtg ggc    1296
Asn Arg Ser Leu Ile Val Gly Leu Lys Ile Ser Thr Lys Ser Val Gly
            420                 425                 430 cga gac gag cgg gag gat atc acc cac acc tac aaa tac cca gag ggg    1344
Arg Asp Glu Arg Glu Asp Ile Thr His Thr Tyr Lys Tyr Pro Glu Gly
        435                 440                 445 tcc tca gag gag agg gag gcc ttc aca agg gcg aac cac ctg aac aaa    1392
Ser Ser Glu Glu Arg Glu Ala Phe Thr Arg Ala Asn His Leu Asn Lys
    450                 455                 460 ctg gcc gag aag gag gag aca ggg atg gcc atg cgg atc cgt gtg ggc    1440
Leu Ala Glu Lys Glu Glu Thr Gly Met Ala Met Arg Ile Arg Val Gly
465                 470                 475                 480 cag agc atg aac atg ggc agt gac ttt gac gtc ttt gcc cac atc acc    1488
Gln Ser Met Asn Met Gly Ser Asp Phe Asp Val Phe Ala His Ile Thr
                485                 490                 495 aac aac acc gct gag gag tac gtc tgc cgc ctc ctg ctc tgt gcc cgc    1536
Asn Asn Thr Ala Glu Glu Tyr Val Cys Arg Leu Leu Leu Cys Ala Arg
            500                 505                 510 acc gtc agc tac aat ggg atc ttg ggg ccc gag tgt ggc acc aag tac    1584
Thr Val Ser Tyr Asn Gly Ile Leu Gly Pro Glu Cys Gly Thr Lys Tyr
        515                 520                 525 ctg ctc aac ctc aac ctg gag cct ttc tct gag aag agc gtt cct ctt    1632
Leu Leu Asn Leu Asn Leu Glu Pro Phe Ser Glu Lys Ser Val Pro Leu
    530                 535                 540 tgc atc ctc tat gag aaa tac cgt gac tgc ctt acg gag tcc aac ctc    1680
Cys Ile Leu Tyr Glu Lys Tyr Arg Asp Cys Leu Thr Glu Ser Asn Leu
545                 550                 555                 560 atc aag gtg cgg gcc ctc ctc gtg gag cca gtt atc aac agc tac ctg    1728
Ile Lys Val Arg Ala Leu Leu Val Glu Pro Val Ile Asn Ser Tyr Leu
                565                 570                 575 ctg gct gag agg gac ctc tac ctg gag aat cca gaa atc aag atc cgg    1776
Leu Ala Glu Arg Asp Leu Tyr Leu Glu Asn Pro Glu Ile Lys Ile Arg
            580                 585                 590 atc ctt ggg gag ccc aag cag aaa cgc aag ctg gtg gct gag gtg tcc    1824
Ile Leu Gly Glu Pro Lys Gln Lys Arg Lys Leu Val Ala Glu Val Ser
        595                 600                 605 ctg cag aac ccg ctc cct gtg gcc ctg gaa ggc tgc acc ttc act gtg    1872
Leu Gln Asn Pro Leu Pro Val Ala Leu Glu Gly Cys Thr Phe Thr Val
    610                 615                 620 gag ggg gcc ggc ctg act gag gag cag aag acg gtg gag atc cca gac    1920
Glu Gly Ala Gly Leu Thr Glu Glu Gln Lys Thr Val Glu Ile Pro Asp
625                 630                 635                 640
```

```
ccc gtg gag gca ggg gag gaa gtt aag gtg aga atg gac ctg ctg ccg      1968
Pro Val Glu Ala Gly Glu Glu Val Lys Val Arg Met Asp Leu Leu Pro
                645                 650                 655 ctc cac atg ggc ctc cac aag ctg gtg gtg aac ttc gag agc gac aag      2016
Leu His Met Gly Leu His Lys Leu Val Val Asn Phe Glu Ser Asp Lys
            660                 665                 670 ctg aag gct gtg aag ggc ttc cgg aat gtc atc att ggc ccc gcc taa      2064
Leu Lys Ala Val Lys Gly Phe Arg Asn Val Ile Ile Gly Pro Ala
        675                 680                 685

<210> SEQ ID NO 2
<211> LENGTH: 687
<212> TYPE: PRT
<213> ORGANISM: Homo sapiens

<400> SEQUENCE: 2

Met Ala Glu Glu Leu Val Leu Glu Arg Cys Asp Leu Glu Leu Glu Thr
1               5                   10                  15

Asn Gly Arg Asp His His Thr Ala Asp Leu Cys Arg Glu Lys Leu Val
            20                  25                  30

Val Arg Arg Gly Gln Pro Phe Trp Leu Thr Leu His Phe Glu Gly Arg
        35                  40                  45

Asn Tyr Glu Ala Ser Val Asp Ser Leu Thr Phe Ser Val Val Thr Gly
    50                  55                  60

Pro Ala Pro Ser Gln Glu Ala Gly Thr Lys Ala Arg Phe Pro Leu Arg
65                  70                  75                  80

Asp Ala Val Glu Glu Gly Asp Trp Thr Ala Thr Val Val Asp Gln Gln
                85                  90                  95

Asp Cys Thr Leu Ser Leu Gln Leu Thr Thr Pro Ala Asn Ala Pro Ile
            100                 105                 110

Gly Leu Tyr Arg Leu Ser Leu Glu Ala Ser Thr Gly Tyr Gln Gly Ser
        115                 120                 125

Ser Phe Val Leu Gly His Phe Ile Leu Leu Phe Asn Ala Trp Cys Pro
    130                 135                 140

Ala Asp Ala Val Tyr Leu Asp Ser Glu Glu Glu Arg Gln Glu Tyr Val
145                 150                 155                 160

Leu Thr Gln Gln Gly Phe Ile Tyr Gln Gly Ser Ala Lys Phe Ile Lys
                165                 170                 175

Asn Ile Pro Trp Asn Phe Gly Gln Phe Glu Asp Gly Ile Leu Asp Ile
            180                 185                 190

Cys Leu Ile Leu Leu Asp Val Asn Pro Lys Phe Leu Lys Asn Ala Gly
        195                 200                 205

Arg Asp Cys Ser Arg Arg Ser Ser Pro Val Tyr Val Gly Arg Val Val
    210                 215                 220

Ser Gly Met Val Asn Cys Asn Asp Asp Gln Gly Val Leu Leu Gly Arg
225                 230                 235                 240

Trp Asp Asn Asn Tyr Gly Asp Gly Val Ser Pro Met Ser Trp Ile Gly
                245                 250                 255

Ser Val Asp Ile Leu Arg Arg Trp Lys Asn His Gly Cys Gln Arg Val
            260                 265                 270

Lys Tyr Gly Gln Cys Trp Val Phe Ala Ala Val Ala Cys Thr Val Leu
        275                 280                 285

Arg Cys Leu Gly Ile Pro Thr Arg Val Val Thr Asn Tyr Asn Ser Ala
    290                 295                 300

His Asp Gln Asn Ser Asn Leu Leu Ile Glu Tyr Phe Arg Asn Glu Phe
305                 310                 315                 320
```

-continued

Gly Glu Ile Gln Gly Asp Lys Ser Glu Met Ile Trp Asn Phe His Cys
                325                 330                 335

Trp Val Glu Ser Trp Met Thr Arg Pro Asp Leu Gln Pro Gly Tyr Glu
            340                 345                 350

Gly Trp Gln Ala Leu Asp Pro Thr Pro Gln Glu Lys Ser Glu Gly Thr
        355                 360                 365

Tyr Cys Cys Gly Pro Val Pro Val Arg Ala Ile Lys Glu Gly Asp Leu
    370                 375                 380

Ser Thr Lys Tyr Asp Ala Pro Phe Val Phe Ala Glu Val Asn Ala Asp
385                 390                 395                 400

Val Val Asp Trp Ile Gln Gln Asp Gly Ser Val His Lys Ser Ile
                405                 410                 415

Asn Arg Ser Leu Ile Val Gly Leu Lys Ile Ser Thr Lys Ser Val Gly
            420                 425                 430

Arg Asp Glu Arg Glu Asp Ile Thr His Thr Tyr Lys Tyr Pro Glu Gly
        435                 440                 445

Ser Ser Glu Glu Arg Glu Ala Phe Thr Arg Ala Asn His Leu Asn Lys
    450                 455                 460

Leu Ala Glu Lys Glu Glu Thr Gly Met Ala Met Arg Ile Arg Val Gly
465                 470                 475                 480

Gln Ser Met Asn Met Gly Ser Asp Phe Asp Val Phe Ala His Ile Thr
                485                 490                 495

Asn Asn Thr Ala Glu Glu Tyr Val Cys Arg Leu Leu Cys Ala Arg
            500                 505                 510

Thr Val Ser Tyr Asn Gly Ile Leu Gly Pro Glu Cys Gly Thr Lys Tyr
        515                 520                 525

Leu Leu Asn Leu Asn Leu Glu Pro Phe Ser Glu Lys Ser Val Pro Leu
    530                 535                 540

Cys Ile Leu Tyr Glu Lys Tyr Arg Asp Cys Leu Thr Glu Ser Asn Leu
545                 550                 555                 560

Ile Lys Val Arg Ala Leu Leu Val Glu Pro Val Ile Asn Ser Tyr Leu
                565                 570                 575

Leu Ala Glu Arg Asp Leu Tyr Leu Glu Asn Pro Glu Ile Lys Ile Arg
            580                 585                 590

Ile Leu Gly Glu Pro Lys Gln Lys Arg Lys Leu Val Ala Glu Val Ser
        595                 600                 605

Leu Gln Asn Pro Leu Pro Val Ala Leu Glu Gly Cys Thr Phe Thr Val
    610                 615                 620

Glu Gly Ala Gly Leu Thr Glu Glu Gln Lys Thr Val Glu Ile Pro Asp
625                 630                 635                 640

Pro Val Glu Ala Gly Glu Glu Val Lys Val Arg Met Asp Leu Leu Pro
                645                 650                 655

Leu His Met Gly Leu His Lys Leu Val Val Asn Phe Glu Ser Asp Lys
            660                 665                 670

Leu Lys Ala Val Lys Gly Phe Arg Asn Val Ile Ile Gly Pro Ala
        675                 680                 685

<210> SEQ ID NO 3
<211> LENGTH: 19
<212> TYPE: RNA
<213> ORGANISM: Homo sapiens

<400> SEQUENCE: 3
acaagagcga gaugaucug                                                19

```
<210> SEQ ID NO 4
<211> LENGTH: 19
<212> TYPE: RNA
<213> ORGANISM: Homo sapiens

<400> SEQUENCE: 4
agagcgagau gaucuggaa                                                  19

<210> SEQ ID NO 5
<211> LENGTH: 19
<212> TYPE: RNA
<213> ORGANISM: Homo sapiens

<400> SEQUENCE: 5
accccaaguu ccugaagaa                                                  19

<210> SEQ ID NO 6
<211> LENGTH: 19
<212> TYPE: RNA
<213> ORGANISM: Homo sapiens

<400> SEQUENCE: 6
gcgagaugau cuggaacuu                                                  19

<210> SEQ ID NO 7
<211> LENGTH: 19
<212> TYPE: RNA
<213> ORGANISM: Homo sapiens

<400> SEQUENCE: 7
caaauccauc aaccguucc                                                  19

<210> SEQ ID NO 8
<211> LENGTH: 19
<212> TYPE: RNA
<213> ORGANISM: Mus musculus

<400> SEQUENCE: 8
gaacauccau gagaaacuu                                                  19

<210> SEQ ID NO 9
<211> LENGTH: 19
<212> TYPE: RNA
<213> ORGANISM: Mus musculus

<400> SEQUENCE: 9
cgaccuaugc caagagaaa                                                  19

<210> SEQ ID NO 10
<211> LENGTH: 19
<212> TYPE: RNA
<213> ORGANISM: Mus musculus

<400> SEQUENCE: 10
ggugugauuu ggagauuca                                                  19

<210> SEQ ID NO 11
<211> LENGTH: 19
<212> TYPE: RNA
<213> ORGANISM: Mus musculus

<400> SEQUENCE: 11
ccaaccaccu gaacaaacu                                                  19
```

```
<210> SEQ ID NO 12
<211> LENGTH: 19
<212> TYPE: RNA
<213> ORGANISM: Mus musculus

<400> SEQUENCE: 12
gaacaaacug gcagagaaa                                                  19

<210> SEQ ID NO 13
<211> LENGTH: 19
<212> TYPE: RNA
<213> ORGANISM: Mus musculus

<400> SEQUENCE: 13
gcucugucaa guucaucaa                                                  19

<210> SEQ ID NO 14
<211> LENGTH: 19
<212> TYPE: RNA
<213> ORGANISM: Mus musculus

<400> SEQUENCE: 14
gaucccuacu cugagaaca                                                  19

<210> SEQ ID NO 15
<211> LENGTH: 19
<212> TYPE: RNA
<213> ORGANISM: Mus musculus

<400> SEQUENCE: 15
ccagaguggu gaccaacua                                                  19

<210> SEQ ID NO 16
<211> LENGTH: 19
<212> TYPE: RNA
<213> ORGANISM: Mus musculus

<400> SEQUENCE: 16
gcaacaagag cgagaugau                                                  19

<210> SEQ ID NO 17
<211> LENGTH: 19
<212> TYPE: RNA
<213> ORGANISM: Mus musculus

<400> SEQUENCE: 17
gcaaccugcu caucgagua                                                  19

<210> SEQ ID NO 18
<211> LENGTH: 19
<212> TYPE: RNA
<213> ORGANISM: Homo sapiens

<400> SEQUENCE: 18
gugaccuaac cacuuagca                                                  19

<210> SEQ ID NO 19
<211> LENGTH: 19
<212> TYPE: RNA
<213> ORGANISM: Homo sapiens

<400> SEQUENCE: 19
guagugaccu aaccacuua                                                  19
```

```
<210> SEQ ID NO 20
<211> LENGTH: 19
<212> TYPE: RNA
<213> ORGANISM: Homo sapiens

<400> SEQUENCE: 20
gacgcuggga caacaacua                                                19

<210> SEQ ID NO 21
<211> LENGTH: 19
<212> TYPE: RNA
<213> ORGANISM: Homo sapiens

<400> SEQUENCE: 21
cagaucaucu cgcucuugu                                                19

<210> SEQ ID NO 22
<211> LENGTH: 19
<212> TYPE: RNA
<213> ORGANISM: Homo sapiens

<400> SEQUENCE: 22
uuccagauca ucucgcucu                                                19

<210> SEQ ID NO 23
<211> LENGTH: 19
<212> TYPE: RNA
<213> ORGANISM: Homo sapiens

<400> SEQUENCE: 23
uucuucagga acuuggggu                                                19

<210> SEQ ID NO 24
<211> LENGTH: 19
<212> TYPE: RNA
<213> ORGANISM: Homo sapiens

<400> SEQUENCE: 24 aaguccaga ucaucucgc                                                 19

<210> SEQ ID NO 25
<211> LENGTH: 19
<212> TYPE: RNA
<213> ORGANISM: Homo sapiens

<400> SEQUENCE: 25
ggaacgguug auggauuug                                                19

<210> SEQ ID NO 26
<211> LENGTH: 19
<212> TYPE: RNA
<213> ORGANISM: Mus musculus

<400> SEQUENCE: 26
aaguuucuca uggauguuc                                                19

<210> SEQ ID NO 27
<211> LENGTH: 19
<212> TYPE: RNA
<213> ORGANISM: Mus musculus

<400> SEQUENCE: 27
uuucucuugg cauaggucg                                                19
```

```
<210> SEQ ID NO 28
<211> LENGTH: 19
<212> TYPE: RNA
<213> ORGANISM: Mus musculus

<400> SEQUENCE: 28
ugaaucucca aaucacacc                                                  19

<210> SEQ ID NO 29
<211> LENGTH: 19
<212> TYPE: RNA
<213> ORGANISM: Mus musculus

<400> SEQUENCE: 29
aguuuguuca ggugguugg                                                  19

<210> SEQ ID NO 30
<211> LENGTH: 19
<212> TYPE: RNA
<213> ORGANISM: Mus musculus

<400> SEQUENCE: 30
uuucucugcc aguuuguuc                                                  19

<210> SEQ ID NO 31
<211> LENGTH: 19
<212> TYPE: RNA
<213> ORGANISM: Mus musculus

<400> SEQUENCE: 31
uugaugaacu ugacagagc                                                  19

<210> SEQ ID NO 32
<211> LENGTH: 19
<212> TYPE: RNA
<213> ORGANISM: Mus musculus

<400> SEQUENCE: 32
uguucucaga guagggauc                                                  19

<210> SEQ ID NO 33
<211> LENGTH: 19
<212> TYPE: RNA
<213> ORGANISM: Mus musculus

<400> SEQUENCE: 33
uaguugguca ccacucugg                                                  19

<210> SEQ ID NO 34
<211> LENGTH: 19
<212> TYPE: RNA
<213> ORGANISM: Mus musculus

<400> SEQUENCE: 34
aucaucucgc ucuuguugc                                                  19

<210> SEQ ID NO 35
<211> LENGTH: 19
<212> TYPE: RNA
<213> ORGANISM: Mus musculus

<400> SEQUENCE: 35
uacucgauga gcagguugc                                                  19
```

-continued

```
<210> SEQ ID NO 36
<211> LENGTH: 19
<212> TYPE: RNA
<213> ORGANISM: Homo sapiens

<400> SEQUENCE: 36
ugcuaagugg uuaggucac                                               19

<210> SEQ ID NO 37
<211> LENGTH: 19
<212> TYPE: RNA
<213> ORGANISM: Homo sapiens

<400> SEQUENCE: 37
uaagugguua ggucacuac                                               19

<210> SEQ ID NO 38
<211> LENGTH: 19
<212> TYPE: RNA
<213> ORGANISM: Homo sapiens

<400> SEQUENCE: 38
uaguuguugu cccagcguc                                               19

<210> SEQ ID NO 39
<211> LENGTH: 19
<212> TYPE: RNA
<213> ORGANISM: Homo sapiens

<400> SEQUENCE: 39
uuccacugcu ggguggagu                                               19

<210> SEQ ID NO 40
<211> LENGTH: 19
<212> TYPE: RNA
<213> ORGANISM: Homo sapiens

<400> SEQUENCE: 40
aagagcgaga ugaucugga                                               19

<210> SEQ ID NO 41
<211> LENGTH: 19
<212> TYPE: RNA
<213> ORGANISM: Homo sapiens

<400> SEQUENCE: 41
caagagcgag augaucugg                                               19

<210> SEQ ID NO 42
<211> LENGTH: 19
<212> TYPE: RNA
<213> ORGANISM: Homo sapiens

<400> SEQUENCE: 42
aaccaccuga acaaacugg                                               19

<210> SEQ ID NO 43
<211> LENGTH: 19
<212> TYPE: RNA
<213> ORGANISM: Homo sapiens

<400> SEQUENCE: 43
accaccugaa caaacuggc                                               19
```

```
<210> SEQ ID NO 44
<211> LENGTH: 19
<212> TYPE: RNA
<213> ORGANISM: Homo sapiens

<400> SEQUENCE: 44
cuggaacuuc cacugcugg                                                    19

<210> SEQ ID NO 45
<211> LENGTH: 19
<212> TYPE: RNA
<213> ORGANISM: Homo sapiens

<400> SEQUENCE: 45
aacuuccacu gcugggugg                                                    19

<210> SEQ ID NO 46
<211> LENGTH: 19
<212> TYPE: RNA
<213> ORGANISM: Homo sapiens

<400> SEQUENCE: 46
aggagaagag cgaagggac                                                    19

<210> SEQ ID NO 47
<211> LENGTH: 19
<212> TYPE: RNA
<213> ORGANISM: Homo sapiens

<400> SEQUENCE: 47
ugaucuggaa cuuccacug                                                    19

<210> SEQ ID NO 48
<211> LENGTH: 19
<212> TYPE: RNA
<213> ORGANISM: Homo sapiens

<400> SEQUENCE: 48
gagcgagaug aucuggaac                                                    19

<210> SEQ ID NO 49
<211> LENGTH: 19
<212> TYPE: RNA
<213> ORGANISM: Homo sapiens

<400> SEQUENCE: 49
ucuggaacuu ccacugcug                                                    19

<210> SEQ ID NO 50
<211> LENGTH: 19
<212> TYPE: RNA
<213> ORGANISM: Homo sapiens

<400> SEQUENCE: 50
gaucuggaac uuccacugc                                                    19

<210> SEQ ID NO 51
<211> LENGTH: 19
<212> TYPE: RNA
<213> ORGANISM: Homo sapiens

<400> SEQUENCE: 51
gagaugaucu ggaacuucc                                                    19
```

```
<210> SEQ ID NO 52
<211> LENGTH: 19
<212> TYPE: RNA
<213> ORGANISM: Homo sapiens

<400> SEQUENCE: 52
agcgagauga ucuggaacu                                                 19

<210> SEQ ID NO 53
<211> LENGTH: 19
<212> TYPE: RNA
<213> ORGANISM: Homo sapiens

<400> SEQUENCE: 53
agaugaucug gaacuucca                                                 19

<210> SEQ ID NO 54
<211> LENGTH: 19
<212> TYPE: RNA
<213> ORGANISM: Homo sapiens

<400> SEQUENCE: 54
ccccaaguuc cugaagaac                                                 19

<210> SEQ ID NO 55
<211> LENGTH: 19
<212> TYPE: RNA
<213> ORGANISM: Homo sapiens

<400> SEQUENCE: 55
aucuggaacu uccacugcu                                                 19

<210> SEQ ID NO 56
<211> LENGTH: 19
<212> TYPE: RNA
<213> ORGANISM: Homo sapiens

<400> SEQUENCE: 56
agcuuugugc ugggccacu                                                 19

<210> SEQ ID NO 57
<211> LENGTH: 19
<212> TYPE: RNA
<213> ORGANISM: Homo sapiens

<400> SEQUENCE: 57
aaccccaagu uccugaaga                                                 19

<210> SEQ ID NO 58
<211> LENGTH: 19
<212> TYPE: RNA
<213> ORGANISM: Homo sapiens

<400> SEQUENCE: 58
caggagaaga gcgaaggga                                                 19

<210> SEQ ID NO 59
<211> LENGTH: 19
<212> TYPE: RNA
<213> ORGANISM: Homo sapiens

<400> SEQUENCE: 59
uugugcuggg ccacuucau                                                 19
```

-continued

```
<210> SEQ ID NO 60
<211> LENGTH: 19
<212> TYPE: RNA
<213> ORGANISM: Homo sapiens

<400> SEQUENCE: 60
gaacuuccac ugcugggug                                                   19

<210> SEQ ID NO 61
<211> LENGTH: 19
<212> TYPE: RNA
<213> ORGANISM: Homo sapiens

<400> SEQUENCE: 61
ggaacuucca cugcugggu                                                   19

<210> SEQ ID NO 62
<211> LENGTH: 19
<212> TYPE: RNA
<213> ORGANISM: Homo sapiens

<400> SEQUENCE: 62
acuuccacug cugggugga                                                   19

<210> SEQ ID NO 63
<211> LENGTH: 19
<212> TYPE: RNA
<213> ORGANISM: Homo sapiens

<400> SEQUENCE: 63
cgagaugauc uggaacuuc                                                   19

<210> SEQ ID NO 64
<211> LENGTH: 19
<212> TYPE: RNA
<213> ORGANISM: Homo sapiens

<400> SEQUENCE: 64
augaucugga acuuccacu                                                   19

<210> SEQ ID NO 65
<211> LENGTH: 19
<212> TYPE: RNA
<213> ORGANISM: Homo sapiens

<400> SEQUENCE: 65
uuugugcugg gccacuuca                                                   19

<210> SEQ ID NO 66
<211> LENGTH: 19
<212> TYPE: RNA
<213> ORGANISM: Homo sapiens

<400> SEQUENCE: 66
gaugaucugg aacuuccac                                                   19

<210> SEQ ID NO 67
<211> LENGTH: 19
<212> TYPE: RNA
<213> ORGANISM: Homo sapiens

<400> SEQUENCE: 67
uggaacuucc acugcuggg                                                   19
```

```
<210> SEQ ID NO 68
<211> LENGTH: 19
<212> TYPE: RNA
<213> ORGANISM: Homo sapiens

<400> SEQUENCE: 68
cuuugugcug ggccacuuc                                                    19

<210> SEQ ID NO 69
<211> LENGTH: 19
<212> TYPE: RNA
<213> ORGANISM: Homo sapiens

<400> SEQUENCE: 69
cuuugugcug ggccacuuc                                                    19

<210> SEQ ID NO 70
<211> LENGTH: 19
<212> TYPE: RNA
<213> ORGANISM: Homo sapiens

<400> SEQUENCE: 70
ucagcacuaa gagcguggg                                                    19

<210> SEQ ID NO 71
<211> LENGTH: 19
<212> TYPE: RNA
<213> ORGANISM: Homo sapiens

<400> SEQUENCE: 71
agaucagcac uaagagcgu                                                    19

<210> SEQ ID NO 72
<211> LENGTH: 19
<212> TYPE: RNA
<213> ORGANISM: Homo sapiens

<400> SEQUENCE: 72
gaagaucagc acuaagagc                                                    19

<210> SEQ ID NO 73
<211> LENGTH: 19
<212> TYPE: RNA
<213> ORGANISM: Homo sapiens

<400> SEQUENCE: 73
gaucagcacu aagagcgug                                                    19

<210> SEQ ID NO 74
<211> LENGTH: 19
<212> TYPE: RNA
<213> ORGANISM: Homo sapiens

<400> SEQUENCE: 74
aguauggcca gugcugggu                                                    19

<210> SEQ ID NO 75
<211> LENGTH: 19
<212> TYPE: RNA
<213> ORGANISM: Homo sapiens

<400> SEQUENCE: 75
aaguauggcc agugcuggg                                                    19
```

-continued

```
<210> SEQ ID NO 76
<211> LENGTH: 19
<212> TYPE: RNA
<213> ORGANISM: Homo sapiens

<400> SEQUENCE: 76
aucagcacua agagcgugg                                                19

<210> SEQ ID NO 77
<211> LENGTH: 19
<212> TYPE: RNA
<213> ORGANISM: Homo sapiens

<400> SEQUENCE: 77
aagaucagca cuaagagcg                                                19

<210> SEQ ID NO 78
<211> LENGTH: 19
<212> TYPE: RNA
<213> ORGANISM: Homo sapiens

<400> SEQUENCE: 78
ggauccuaga caucugccu                                                19

<210> SEQ ID NO 79
<211> LENGTH: 19
<212> TYPE: RNA
<213> ORGANISM: Homo sapiens

<400> SEQUENCE: 79
cgcugggaca acaacuacg                                                19

<210> SEQ ID NO 80
<211> LENGTH: 19
<212> TYPE: RNA
<213> ORGANISM: Homo sapiens

<400> SEQUENCE: 80
cuuggaauuu ugggcaguu                                                19

<210> SEQ ID NO 81
<211> LENGTH: 19
<212> TYPE: RNA
<213> ORGANISM: Homo sapiens

<400> SEQUENCE: 81
gucaacugca acgaugacc                                                19

<210> SEQ ID NO 82
<211> LENGTH: 19
<212> TYPE: RNA
<213> ORGANISM: Homo sapiens

<400> SEQUENCE: 82
caagaacaua ccuuggaau                                                19

<210> SEQ ID NO 83
<211> LENGTH: 19
<212> TYPE: RNA
<213> ORGANISM: Homo sapiens

<400> SEQUENCE: 83
cucaucgagu acuuccgca                                                19
```

```
<210> SEQ ID NO 84
<211> LENGTH: 19
<212> TYPE: RNA
<213> ORGANISM: Homo sapiens

<400> SEQUENCE: 84
gcauggucaa cugcaacga                                                  19

<210> SEQ ID NO 85
<211> LENGTH: 19
<212> TYPE: RNA
<213> ORGANISM: Homo sapiens

<400> SEQUENCE: 85
cggaugcugu guaccugga                                                  19

<210> SEQ ID NO 86
<211> LENGTH: 19
<212> TYPE: RNA
<213> ORGANISM: Homo sapiens

<400> SEQUENCE: 86
ccaugaccag aacagcaac                                                  19

<210> SEQ ID NO 87
<211> LENGTH: 19
<212> TYPE: RNA
<213> ORGANISM: Homo sapiens

<400> SEQUENCE: 87
acauaccuug gaauuuugg                                                  19

<210> SEQ ID NO 88
<211> LENGTH: 19
<212> TYPE: RNA
<213> ORGANISM: Homo sapiens

<400> SEQUENCE: 88
ucgaguacuu ccgcaauga                                                  19

<210> SEQ ID NO 89
<211> LENGTH: 19
<212> TYPE: RNA
<213> ORGANISM: Homo sapiens

<400> SEQUENCE: 89
auggucaacu gcaacgaug                                                  19

<210> SEQ ID NO 90
<211> LENGTH: 19
<212> TYPE: RNA
<213> ORGANISM: Homo sapiens

<400> SEQUENCE: 90
accuuggaau uuugggcag                                                  19

<210> SEQ ID NO 91
<211> LENGTH: 19
<212> TYPE: RNA
<213> ORGANISM: Homo sapiens

<400> SEQUENCE: 91
caaguucauc aagaacaua                                                  19
```

-continued

<210> SEQ ID NO 92
<211> LENGTH: 19
<212> TYPE: RNA
<213> ORGANISM: Homo sapiens

<400> SEQUENCE: 92
uucaucaaga acauaccuu                                                      19

<210> SEQ ID NO 93
<211> LENGTH: 19
<212> TYPE: RNA
<213> ORGANISM: Homo sapiens

<400> SEQUENCE: 93
auaccuugga auuugggc                                                       19

<210> SEQ ID NO 94
<211> LENGTH: 19
<212> TYPE: RNA
<213> ORGANISM: Homo sapiens

<400> SEQUENCE: 94
aguacuuccg caaugaguu                                                      19

<210> SEQ ID NO 95
<211> LENGTH: 19
<212> TYPE: RNA
<213> ORGANISM: Homo sapiens

<400> SEQUENCE: 95
uggguggagu cguggauga                                                      19

<210> SEQ ID NO 96
<211> LENGTH: 19
<212> TYPE: RNA
<213> ORGANISM: Homo sapiens

<400> SEQUENCE: 96
cccaugacca gaacagcaa                                                      19

<210> SEQ ID NO 97
<211> LENGTH: 19
<212> TYPE: RNA
<213> ORGANISM: Homo sapiens

<400> SEQUENCE: 97
ccaaguucau caagaacau                                                      19

<210> SEQ ID NO 98
<211> LENGTH: 19
<212> TYPE: RNA
<213> ORGANISM: Homo sapiens

<400> SEQUENCE: 98
gucaacccca aguccuga                                                       19

<210> SEQ ID NO 99
<211> LENGTH: 19
<212> TYPE: RNA
<213> ORGANISM: Homo sapiens

<400> SEQUENCE: 99
aucaagaaca uaccuugga                                                      19

```
<210> SEQ ID NO 100
<211> LENGTH: 19
<212> TYPE: RNA
<213> ORGANISM: Homo sapiens

<400> SEQUENCE: 100
uggucaacug caacgauga                                                    19

<210> SEQ ID NO 101
<211> LENGTH: 19
<212> TYPE: RNA
<213> ORGANISM: Homo sapiens

<400> SEQUENCE: 101
cauggucaac ugcaacgau                                                    19

<210> SEQ ID NO 102
<211> LENGTH: 19
<212> TYPE: RNA
<213> ORGANISM: Homo sapiens

<400> SEQUENCE: 102
uggaauuuug ggcaguuug                                                    19

<210> SEQ ID NO 103
<211> LENGTH: 19
<212> TYPE: RNA
<213> ORGANISM: Homo sapiens

<400> SEQUENCE: 103
acugcaacga ugaccaggg                                                    19

<210> SEQ ID NO 104
<211> LENGTH: 19
<212> TYPE: RNA
<213> ORGANISM: Homo sapiens

<400> SEQUENCE: 104
auccuagaca ucugccuga                                                    19

<210> SEQ ID NO 105
<211> LENGTH: 19
<212> TYPE: RNA
<213> ORGANISM: Homo sapiens

<400> SEQUENCE: 105
caacugcaac gaugaccag                                                    19

<210> SEQ ID NO 106
<211> LENGTH: 19
<212> TYPE: RNA
<213> ORGANISM: Homo sapiens

<400> SEQUENCE: 106
ggaauuuugg gcaguuuga                                                    19

<210> SEQ ID NO 107
<211> LENGTH: 19
<212> TYPE: RNA
<213> ORGANISM: Homo sapiens

<400> SEQUENCE: 107
agcggaugcu guguaccug                                                    19
```

-continued

```
<210> SEQ ID NO 108
<211> LENGTH: 19
<212> TYPE: RNA
<213> ORGANISM: Homo sapiens

<400> SEQUENCE: 108
uuugcccaca ucaccaaca                                                  19

<210> SEQ ID NO 109
<211> LENGTH: 19
<212> TYPE: RNA
<213> ORGANISM: Homo sapiens

<400> SEQUENCE: 109
aagaacauac cuuggaauu                                                  19

<210> SEQ ID NO 110
<211> LENGTH: 19
<212> TYPE: RNA
<213> ORGANISM: Homo sapiens

<400> SEQUENCE: 110
uccuagacau cugccugau                                                  19

<210> SEQ ID NO 111
<211> LENGTH: 19
<212> TYPE: RNA
<213> ORGANISM: Homo sapiens

<400> SEQUENCE: 111
cgaguacuuc cgcaaugag                                                  19

<210> SEQ ID NO 112
<211> LENGTH: 19
<212> TYPE: RNA
<213> ORGANISM: Homo sapiens

<400> SEQUENCE: 112
ugucaacccc aaguuccug                                                  19

<210> SEQ ID NO 113
<211> LENGTH: 19
<212> TYPE: RNA
<213> ORGANISM: Homo sapiens

<400> SEQUENCE: 113
gacgucuuug cccacauca                                                  19

<210> SEQ ID NO 114
<211> LENGTH: 19
<212> TYPE: RNA
<213> ORGANISM: Homo sapiens

<400> SEQUENCE: 114
gaugcugugu accuggacu                                                  19

<210> SEQ ID NO 115
<211> LENGTH: 19
<212> TYPE: RNA
<213> ORGANISM: Homo sapiens

<400> SEQUENCE: 115
agaacauacc uuggaauuu                                                  19
```

<210> SEQ ID NO 116
<211> LENGTH: 19
<212> TYPE: RNA
<213> ORGANISM: Homo sapiens

<400> SEQUENCE: 116
acgucuuugc ccacaucac                                                        19

<210> SEQ ID NO 117
<211> LENGTH: 19
<212> TYPE: RNA
<213> ORGANISM: Homo sapiens

<400> SEQUENCE: 117
aucgaguacu uccgcaaug                                                        19

<210> SEQ ID NO 118
<211> LENGTH: 19
<212> TYPE: RNA
<213> ORGANISM: Homo sapiens

<400> SEQUENCE: 118
aaguucauca agaacauac                                                        19

<210> SEQ ID NO 119
<211> LENGTH: 19
<212> TYPE: RNA
<213> ORGANISM: Homo sapiens

<400> SEQUENCE: 119
uggagucgug gaugaccag                                                        19

<210> SEQ ID NO 120
<211> LENGTH: 19
<212> TYPE: RNA
<213> ORGANISM: Homo sapiens

<400> SEQUENCE: 120
gugacaagag cgagaugau                                                        19

<210> SEQ ID NO 121
<211> LENGTH: 19
<212> TYPE: RNA
<213> ORGANISM: Homo sapiens

<400> SEQUENCE: 121
ucaucgagua cuuccgcaa                                                        19

<210> SEQ ID NO 122
<211> LENGTH: 19
<212> TYPE: RNA
<213> ORGANISM: Homo sapiens

<400> SEQUENCE: 122
guucgugcca ucaaggagg                                                        19

<210> SEQ ID NO 123
<211> LENGTH: 19
<212> TYPE: RNA
<213> ORGANISM: Homo sapiens

<400> SEQUENCE: 123
caucaagaac auaccuugg                                                        19

```
<210> SEQ ID NO 124
<211> LENGTH: 19
<212> TYPE: RNA
<213> ORGANISM: Homo sapiens

<400> SEQUENCE: 124
uaccuuggaa uuuugggca                                               19

<210> SEQ ID NO 125
<211> LENGTH: 19
<212> TYPE: RNA
<213> ORGANISM: Homo sapiens

<400> SEQUENCE: 125
gacaagagcg agaugaucu                                               19

<210> SEQ ID NO 126
<211> LENGTH: 19
<212> TYPE: RNA
<213> ORGANISM: Homo sapiens

<400> SEQUENCE: 126
cgucuuugcc cacaucacc                                               19

<210> SEQ ID NO 127
<211> LENGTH: 19
<212> TYPE: RNA
<213> ORGANISM: Homo sapiens

<400> SEQUENCE: 127
augcugugua ccuggacuc                                               19

<210> SEQ ID NO 128
<211> LENGTH: 19
<212> TYPE: RNA
<213> ORGANISM: Homo sapiens

<400> SEQUENCE: 128
uuggaauuuu gggcaguuu                                               19

<210> SEQ ID NO 129
<211> LENGTH: 19
<212> TYPE: RNA
<213> ORGANISM: Homo sapiens

<400> SEQUENCE: 129
gccaaguuca ucaagaaca                                               19

<210> SEQ ID NO 130
<211> LENGTH: 19
<212> TYPE: RNA
<213> ORGANISM: Homo sapiens

<400> SEQUENCE: 130
aguucaucaa gaacauacc                                               19

<210> SEQ ID NO 131
<211> LENGTH: 19
<212> TYPE: RNA
<213> ORGANISM: Homo sapiens

<400> SEQUENCE: 131
gucuuugccc acaucacca                                               19
```

-continued

```
<210> SEQ ID NO 132
<211> LENGTH: 19
<212> TYPE: RNA
<213> ORGANISM: Homo sapiens

<400> SEQUENCE: 132
gggauccuag acaucugcc                                                  19

<210> SEQ ID NO 133
<211> LENGTH: 19
<212> TYPE: RNA
<213> ORGANISM: Homo sapiens

<400> SEQUENCE: 133
gauccuagac aucugccug                                                  19

<210> SEQ ID NO 134
<211> LENGTH: 19
<212> TYPE: RNA
<213> ORGANISM: Homo sapiens

<400> SEQUENCE: 134
augucaaccc caaguuccu                                                  19

<210> SEQ ID NO 135
<211> LENGTH: 19
<212> TYPE: RNA
<213> ORGANISM: Homo sapiens

<400> SEQUENCE: 135
ucaucaagaa cauaccuug                                                  19

<210> SEQ ID NO 136
<211> LENGTH: 19
<212> TYPE: RNA
<213> ORGANISM: Homo sapiens

<400> SEQUENCE: 136
ucaagaacau accuuggaa                                                  19

<210> SEQ ID NO 137
<211> LENGTH: 19
<212> TYPE: RNA
<213> ORGANISM: Homo sapiens

<400> SEQUENCE: 137
caucgaguac uuccgcaau                                                  19

<210> SEQ ID NO 138
<211> LENGTH: 19
<212> TYPE: RNA
<213> ORGANISM: Homo sapiens

<400> SEQUENCE: 138
ggaugcugug uaccuggac                                                  19

<210> SEQ ID NO 139
<211> LENGTH: 19
<212> TYPE: RNA
<213> ORGANISM: Homo sapiens

<400> SEQUENCE: 139
gaugucaacc ccaaguucc                                                  19
```

```
<210> SEQ ID NO 140
<211> LENGTH: 19
<212> TYPE: RNA
<213> ORGANISM: Homo sapiens

<400> SEQUENCE: 140
caugaccaga acagcaacc                                              19

<210> SEQ ID NO 141
<211> LENGTH: 19
<212> TYPE: RNA
<213> ORGANISM: Homo sapiens

<400> SEQUENCE: 141
gcccaugacc agaacagca                                              19

<210> SEQ ID NO 142
<211> LENGTH: 19
<212> TYPE: RNA
<213> ORGANISM: Homo sapiens

<400> SEQUENCE: 142
gaacauaccu uggaauuuu                                              19

<210> SEQ ID NO 143
<211> LENGTH: 19
<212> TYPE: RNA
<213> ORGANISM: Homo sapiens

<400> SEQUENCE: 143
guggagucgu ggaugacca                                              19

<210> SEQ ID NO 144
<211> LENGTH: 19
<212> TYPE: RNA
<213> ORGANISM: Homo sapiens

<400> SEQUENCE: 144
ucaacugcaa cgaugacca                                              19

<210> SEQ ID NO 145
<211> LENGTH: 19
<212> TYPE: RNA
<213> ORGANISM: Homo sapiens

<400> SEQUENCE: 145
auuuugggca guuugaaga                                              19

<210> SEQ ID NO 146
<211> LENGTH: 19
<212> TYPE: RNA
<213> ORGANISM: Homo sapiens

<400> SEQUENCE: 146
aacauaccuu ggaauuuug                                              19

<210> SEQ ID NO 147
<211> LENGTH: 19
<212> TYPE: RNA
<213> ORGANISM: Homo sapiens

<400> SEQUENCE: 147
ugacaagagc gagaugauc                                              19
```

```
<210> SEQ ID NO 148
<211> LENGTH: 19
<212> TYPE: RNA
<213> ORGANISM: Homo sapiens

<400> SEQUENCE: 148
uucgugccau caaggaggg                                                  19

<210> SEQ ID NO 149
<211> LENGTH: 19
<212> TYPE: RNA
<213> ORGANISM: Homo sapiens

<400> SEQUENCE: 149
ucagccccau guccuggau                                                  19

<210> SEQ ID NO 150
<211> LENGTH: 19
<212> TYPE: RNA
<213> ORGANISM: Homo sapiens

<400> SEQUENCE: 150
ggucaacugc aacgaugac                                                  19

<210> SEQ ID NO 151
<211> LENGTH: 19
<212> TYPE: RNA
<213> ORGANISM: Homo sapiens

<400> SEQUENCE: 151
aauuuugggc aguuugaag                                                  19

<210> SEQ ID NO 152
<211> LENGTH: 19
<212> TYPE: RNA
<213> ORGANISM: Homo sapiens

<400> SEQUENCE: 152
cagcggaugc uguguaccu                                                  19

<210> SEQ ID NO 153
<211> LENGTH: 19
<212> TYPE: RNA
<213> ORGANISM: Homo sapiens

<400> SEQUENCE: 153
aacugcaacg augaccagg                                                  19

<210> SEQ ID NO 154
<211> LENGTH: 19
<212> TYPE: RNA
<213> ORGANISM: Homo sapiens

<400> SEQUENCE: 154
augaccagaa cagcaaccu                                                  19

<210> SEQ ID NO 155
<211> LENGTH: 19
<212> TYPE: RNA
<213> ORGANISM: Homo sapiens

<400> SEQUENCE: 155
cauaccuugg aauuuuggg                                                  19
```

-continued

```
<210> SEQ ID NO 156
<211> LENGTH: 19
<212> TYPE: RNA
<213> ORGANISM: Homo sapiens

<400> SEQUENCE: 156
cuuugcccac aucaccaac                                                 19

<210> SEQ ID NO 157
<211> LENGTH: 19
<212> TYPE: RNA
<213> ORGANISM: Homo sapiens

<400> SEQUENCE: 157
gaguacuucc gcaaugagu                                                 19

<210> SEQ ID NO 158
<211> LENGTH: 19
<212> TYPE: RNA
<213> ORGANISM: Homo sapiens

<400> SEQUENCE: 158
ggcaugguca acugcaacg                                                 19

<210> SEQ ID NO 159
<211> LENGTH: 19
<212> TYPE: RNA
<213> ORGANISM: Homo sapiens

<400> SEQUENCE: 159
ucuuugccca caucaccaa                                                 19

<210> SEQ ID NO 160
<211> LENGTH: 19
<212> TYPE: RNA
<213> ORGANISM: Homo sapiens

<400> SEQUENCE: 160
gaauuugggg caguuugaa                                                 19

<210> SEQ ID NO 161
<211> LENGTH: 19
<212> TYPE: RNA
<213> ORGANISM: Homo sapiens

<400> SEQUENCE: 161
ccuuggaauu uugggcagu                                                 19

<210> SEQ ID NO 162
<211> LENGTH: 19
<212> TYPE: RNA
<213> ORGANISM: Homo sapiens

<400> SEQUENCE: 162
guucaucaag aacauaccu                                                 19

<210> SEQ ID NO 163
<211> LENGTH: 19
<212> TYPE: RNA
<213> ORGANISM: Homo sapiens

<400> SEQUENCE: 163
uguaucgccu cagccugga                                                 19
```

-continued

```
<210> SEQ ID NO 164
<211> LENGTH: 19
<212> TYPE: RNA
<213> ORGANISM: Homo sapiens

<400> SEQUENCE: 164
gcucggccaa guucaucaa                                                  19

<210> SEQ ID NO 165
<211> LENGTH: 19
<212> TYPE: RNA
<213> ORGANISM: Homo sapiens

<400> SEQUENCE: 165
ggcucggcca aguucauca                                                  19

<210> SEQ ID NO 166
<211> LENGTH: 19
<212> TYPE: RNA
<213> ORGANISM: Homo sapiens

<400> SEQUENCE: 166
ggacgcuggg acaacaacu                                                  19

<210> SEQ ID NO 167
<211> LENGTH: 19
<212> TYPE: RNA
<213> ORGANISM: Homo sapiens

<400> SEQUENCE: 167
ggcaguuuga agaugggau                                                  19

<210> SEQ ID NO 168
<211> LENGTH: 19
<212> TYPE: RNA
<213> ORGANISM: Homo sapiens

<400> SEQUENCE: 168
aguuugaaga uggggauccu                                                 19

<210> SEQ ID NO 169
<211> LENGTH: 19
<212> TYPE: RNA
<213> ORGANISM: Homo sapiens

<400> SEQUENCE: 169
caguuugaag augggaucc                                                  19

<210> SEQ ID NO 170
<211> LENGTH: 19
<212> TYPE: RNA
<213> ORGANISM: Homo sapiens

<400> SEQUENCE: 170
agggcucggc caaguucau                                                  19

<210> SEQ ID NO 171
<211> LENGTH: 19
<212> TYPE: RNA
<213> ORGANISM: Homo sapiens

<400> SEQUENCE: 171
gcaguuugaa gaugggauc                                                  19
```

```
<210> SEQ ID NO 172
<211> LENGTH: 19
<212> TYPE: RNA
<213> ORGANISM: Homo sapiens

<400> SEQUENCE: 172
caaccccaag uuccugaag                                                    19

<210> SEQ ID NO 173
<211> LENGTH: 19
<212> TYPE: RNA
<213> ORGANISM: Homo sapiens

<400> SEQUENCE: 173
gggcaguuug aagauggga                                                    19

<210> SEQ ID NO 174
<211> LENGTH: 19
<212> TYPE: RNA
<213> ORGANISM: Homo sapiens

<400> SEQUENCE: 174
acgcugggac aacaacuac                                                    19

<210> SEQ ID NO 175
<211> LENGTH: 19
<212> TYPE: RNA
<213> ORGANISM: Homo sapiens

<400> SEQUENCE: 175
uacugcugug gcccaguuc                                                    19

<210> SEQ ID NO 176
<211> LENGTH: 19
<212> TYPE: RNA
<213> ORGANISM: Homo sapiens

<400> SEQUENCE: 176
uugcccacau caccaacaa                                                    19

<210> SEQ ID NO 177
<211> LENGTH: 19
<212> TYPE: RNA
<213> ORGANISM: Homo sapiens

<400> SEQUENCE: 177
ccaaguaccu gcucaaccu                                                    19

<210> SEQ ID NO 178
<211> LENGTH: 19
<212> TYPE: RNA
<213> ORGANISM: Homo sapiens

<400> SEQUENCE: 178
cggccaaguu caucaagaa                                                    19

<210> SEQ ID NO 179
<211> LENGTH: 19
<212> TYPE: RNA
<213> ORGANISM: Homo sapiens

<400> SEQUENCE: 179
cgaugggucu gugcacaaa                                                    19
```

```
<210> SEQ ID NO 180
<211> LENGTH: 19
<212> TYPE: RNA
<213> ORGANISM: Homo sapiens

<400> SEQUENCE: 180
cagugacuuu gacgucuuu                                                19

<210> SEQ ID NO 181
<211> LENGTH: 19
<212> TYPE: RNA
<213> ORGANISM: Homo sapiens

<400> SEQUENCE: 181
gcaugaacau gggcaguga                                                19

<210> SEQ ID NO 182
<211> LENGTH: 19
<212> TYPE: RNA
<213> ORGANISM: Homo sapiens

<400> SEQUENCE: 182
caacuacgag gccagugua                                                19

<210> SEQ ID NO 183
<211> LENGTH: 19
<212> TYPE: RNA
<213> ORGANISM: Homo sapiens

<400> SEQUENCE: 183
caugggcagu gacuuugac                                                19

<210> SEQ ID NO 184
<211> LENGTH: 19
<212> TYPE: RNA
<213> ORGANISM: Homo sapiens

<400> SEQUENCE: 184
gcccacauca ccaacaaca                                                19

<210> SEQ ID NO 185
<211> LENGTH: 19
<212> TYPE: RNA
<213> ORGANISM: Homo sapiens

<400> SEQUENCE: 185
cgaaccaccu gaacaaacu                                                19

<210> SEQ ID NO 186
<211> LENGTH: 19
<212> TYPE: RNA
<213> ORGANISM: Homo sapiens

<400> SEQUENCE: 186
ggcccguuuu ccacuaaga                                                19

<210> SEQ ID NO 187
<211> LENGTH: 19
<212> TYPE: RNA
<213> ORGANISM: Homo sapiens

<400> SEQUENCE: 187
ugacgucuuu gcccacauc                                                19
```

```
<210> SEQ ID NO 188
<211> LENGTH: 19
<212> TYPE: RNA
<213> ORGANISM: Homo sapiens

<400> SEQUENCE: 188
gaacaugggc agugacuuu                                                    19

<210> SEQ ID NO 189
<211> LENGTH: 19
<212> TYPE: RNA
<213> ORGANISM: Homo sapiens

<400> SEQUENCE: 189
gcagugacuu ugacgucuu                                                    19

<210> SEQ ID NO 190
<211> LENGTH: 19
<212> TYPE: RNA
<213> ORGANISM: Homo sapiens

<400> SEQUENCE: 190
cuguguuccu ggagcauuu                                                    19

<210> SEQ ID NO 191
<211> LENGTH: 19
<212> TYPE: RNA
<213> ORGANISM: Homo sapiens

<400> SEQUENCE: 191
caaccuggag ccuuucucu                                                    19

<210> SEQ ID NO 192
<211> LENGTH: 19
<212> TYPE: RNA
<213> ORGANISM: Homo sapiens

<400> SEQUENCE: 192
acuccaccca gcaguggaa                                                    19

<210> SEQ ID NO 193
<211> LENGTH: 19
<212> TYPE: RNA
<213> ORGANISM: Homo sapiens

<400> SEQUENCE: 193
uccagaucau cucgcucuu                                                    19

<210> SEQ ID NO 194
<211> LENGTH: 19
<212> TYPE: RNA
<213> ORGANISM: Homo sapiens

<400> SEQUENCE: 194
ccagaucauc ucgcucuug                                                    19

<210> SEQ ID NO 195
<211> LENGTH: 19
<212> TYPE: RNA
<213> ORGANISM: Homo sapiens

<400> SEQUENCE: 195
ccaguuuguu caggugguu                                                    19
```

```
<210> SEQ ID NO 196
<211> LENGTH: 19
<212> TYPE: RNA
<213> ORGANISM: Homo sapiens

<400> SEQUENCE: 196
gccaguuugu ucagguggu                                                       19

<210> SEQ ID NO 197
<211> LENGTH: 19
<212> TYPE: RNA
<213> ORGANISM: Homo sapiens

<400> SEQUENCE: 197
ccagcagugg aaguccag                                                        19

<210> SEQ ID NO 198
<211> LENGTH: 19
<212> TYPE: RNA
<213> ORGANISM: Homo sapiens

<400> SEQUENCE: 198
ccacccagca guggaaguu                                                       19

<210> SEQ ID NO 199
<211> LENGTH: 19
<212> TYPE: RNA
<213> ORGANISM: Homo sapiens

<400> SEQUENCE: 199
gucccuucgc ucuucuccu                                                       19

<210> SEQ ID NO 200
<211> LENGTH: 19
<212> TYPE: RNA
<213> ORGANISM: Homo sapiens

<400> SEQUENCE: 200
caguggaagu uccagauca                                                       19

<210> SEQ ID NO 201
<211> LENGTH: 19
<212> TYPE: RNA
<213> ORGANISM: Homo sapiens

<400> SEQUENCE: 201
guuccagauc aucucgcuc                                                       19

<210> SEQ ID NO 202
<211> LENGTH: 19
<212> TYPE: RNA
<213> ORGANISM: Homo sapiens

<400> SEQUENCE: 202
cagcagugga aguccaga                                                        19

<210> SEQ ID NO 203
<211> LENGTH: 19
<212> TYPE: RNA
<213> ORGANISM: Homo sapiens

<400> SEQUENCE: 203
gcaguggaag uuccagauc                                                       19
```

```
<210> SEQ ID NO 204
<211> LENGTH: 19
<212> TYPE: RNA
<213> ORGANISM: Homo sapiens

<400> SEQUENCE: 204
ggaaguucca gaucaucuc                                                    19

<210> SEQ ID NO 205
<211> LENGTH: 19
<212> TYPE: RNA
<213> ORGANISM: Homo sapiens

<400> SEQUENCE: 205
aguuccagau caucucgcu                                                    19

<210> SEQ ID NO 206
<211> LENGTH: 19
<212> TYPE: RNA
<213> ORGANISM: Homo sapiens

<400> SEQUENCE: 206
uggaaguucc agaucaucu                                                    19

<210> SEQ ID NO 207
<211> LENGTH: 19
<212> TYPE: RNA
<213> ORGANISM: Homo sapiens

<400> SEQUENCE: 207
guucuucagg aacuugggg                                                    19

<210> SEQ ID NO 208
<211> LENGTH: 19
<212> TYPE: RNA
<213> ORGANISM: Homo sapiens

<400> SEQUENCE: 208
agcaguggaa guuccagau                                                    19

<210> SEQ ID NO 209
<211> LENGTH: 19
<212> TYPE: RNA
<213> ORGANISM: Homo sapiens

<400> SEQUENCE: 209
aguggcccag cacaaagcu                                                    19

<210> SEQ ID NO 210
<211> LENGTH: 19
<212> TYPE: RNA
<213> ORGANISM: Homo sapiens

<400> SEQUENCE: 210
ucuucaggaa cuuggggguu                                                   19

<210> SEQ ID NO 211
<211> LENGTH: 19
<212> TYPE: RNA
<213> ORGANISM: Homo sapiens

<400> SEQUENCE: 211
ucccuucgcu cuucuccug                                                    19
```

-continued

```
<210> SEQ ID NO 212
<211> LENGTH: 19
<212> TYPE: RNA
<213> ORGANISM: Homo sapiens

<400> SEQUENCE: 212
augaaguggc ccagcacaa                                                    19

<210> SEQ ID NO 213
<211> LENGTH: 19
<212> TYPE: RNA
<213> ORGANISM: Homo sapiens

<400> SEQUENCE: 213
cacccagcag uggaaguuc                                                    19

<210> SEQ ID NO 214
<211> LENGTH: 19
<212> TYPE: RNA
<213> ORGANISM: Homo sapiens

<400> SEQUENCE: 214
acccagcagu ggaaguucc                                                    19

<210> SEQ ID NO 215
<211> LENGTH: 19
<212> TYPE: RNA
<213> ORGANISM: Homo sapiens

<400> SEQUENCE: 215
uccacccagc aguggaagu                                                    19

<210> SEQ ID NO 216
<211> LENGTH: 19
<212> TYPE: RNA
<213> ORGANISM: Homo sapiens

<400> SEQUENCE: 216
gaaguuccag aucaucucg                                                    19

<210> SEQ ID NO 217
<211> LENGTH: 19
<212> TYPE: RNA
<213> ORGANISM: Homo sapiens

<400> SEQUENCE: 217
aguggaaguu ccagaucau                                                    19

<210> SEQ ID NO 218
<211> LENGTH: 19
<212> TYPE: RNA
<213> ORGANISM: Homo sapiens

<400> SEQUENCE: 218
ugaaguggcc cagcacaaa                                                    19

<210> SEQ ID NO 219
<211> LENGTH: 19
<212> TYPE: RNA
<213> ORGANISM: Homo sapiens

<400> SEQUENCE: 219
guggaaguuc cagaucauc                                                    19
```

```
<210> SEQ ID NO 220
<211> LENGTH: 19
<212> TYPE: RNA
<213> ORGANISM: Homo sapiens

<400> SEQUENCE: 220
cccagcagug gaaguucca                                                  19

<210> SEQ ID NO 221
<211> LENGTH: 19
<212> TYPE: RNA
<213> ORGANISM: Homo sapiens

<400> SEQUENCE: 221
gaaguggccc agcacaaag                                                  19

<210> SEQ ID NO 222
<211> LENGTH: 19
<212> TYPE: RNA
<213> ORGANISM: Homo sapiens

<400> SEQUENCE: 222
aaguggccca gcacaaagc                                                  19

<210> SEQ ID NO 223
<211> LENGTH: 19
<212> TYPE: RNA
<213> ORGANISM: Homo sapiens

<400> SEQUENCE: 223
cccacgcucu uagugcuga                                                  19

<210> SEQ ID NO 224
<211> LENGTH: 19
<212> TYPE: RNA
<213> ORGANISM: Homo sapiens

<400> SEQUENCE: 224
acgcucuuag ugcugaucu                                                  19

<210> SEQ ID NO 225
<211> LENGTH: 19
<212> TYPE: RNA
<213> ORGANISM: Homo sapiens

<400> SEQUENCE: 225
gcucuuagug cugaucuuc                                                  19

<210> SEQ ID NO 226
<211> LENGTH: 19
<212> TYPE: RNA
<213> ORGANISM: Homo sapiens

<400> SEQUENCE: 226
cacgcucuua gugcugauc                                                  19

<210> SEQ ID NO 227
<211> LENGTH: 19
<212> TYPE: RNA
<213> ORGANISM: Homo sapiens

<400> SEQUENCE: 227
acccagcacu ggccauacu                                                  19
```

```
<210> SEQ ID NO 228
<211> LENGTH: 19
<212> TYPE: RNA
<213> ORGANISM: Homo sapiens

<400> SEQUENCE: 228
cccagcacug gccauacuu                                                      19

<210> SEQ ID NO 229
<211> LENGTH: 19
<212> TYPE: RNA
<213> ORGANISM: Homo sapiens

<400> SEQUENCE: 229
ccacgcucuu agugcugau                                                      19

<210> SEQ ID NO 230
<211> LENGTH: 19
<212> TYPE: RNA
<213> ORGANISM: Homo sapiens

<400> SEQUENCE: 230
cgcucuuagu gcugaucuu                                                      19

<210> SEQ ID NO 231
<211> LENGTH: 19
<212> TYPE: RNA
<213> ORGANISM: Homo sapiens

<400> SEQUENCE: 231
aggcagaugu cuaggaucc                                                      19

<210> SEQ ID NO 232
<211> LENGTH: 19
<212> TYPE: RNA
<213> ORGANISM: Homo sapiens

<400> SEQUENCE: 232
cguaguuguu gucccagcg                                                      19

<210> SEQ ID NO 233
<211> LENGTH: 19
<212> TYPE: RNA
<213> ORGANISM: Homo sapiens

<400> SEQUENCE: 233
aacugcccaa aauuccaag                                                      19

<210> SEQ ID NO 234
<211> LENGTH: 19
<212> TYPE: RNA
<213> ORGANISM: Homo sapiens

<400> SEQUENCE: 234
ggucaucguu gcaguugac                                                      19

<210> SEQ ID NO 235
<211> LENGTH: 19
<212> TYPE: RNA
<213> ORGANISM: Homo sapiens

<400> SEQUENCE: 235
auuccaaggu auguucuug                                                      19
```

```
<210> SEQ ID NO 236
<211> LENGTH: 19
<212> TYPE: RNA
<213> ORGANISM: Homo sapiens

<400> SEQUENCE: 236
ugcggaagua cucgaugag                                                  19

<210> SEQ ID NO 237
<211> LENGTH: 19
<212> TYPE: RNA
<213> ORGANISM: Homo sapiens

<400> SEQUENCE: 237
ucguugcagu ugaccaugc                                                  19

<210> SEQ ID NO 238
<211> LENGTH: 19
<212> TYPE: RNA
<213> ORGANISM: Homo sapiens

<400> SEQUENCE: 238
uccagguaca cagcauccg                                                  19

<210> SEQ ID NO 239
<211> LENGTH: 19
<212> TYPE: RNA
<213> ORGANISM: Homo sapiens

<400> SEQUENCE: 239
guugcuguuc uggucaugg                                                  19

<210> SEQ ID NO 240
<211> LENGTH: 19
<212> TYPE: RNA
<213> ORGANISM: Homo sapiens

<400> SEQUENCE: 240
ccaaaauucc aagguaugu                                                  19

<210> SEQ ID NO 241
<211> LENGTH: 19
<212> TYPE: RNA
<213> ORGANISM: Homo sapiens

<400> SEQUENCE: 241
ucauugcgga aguacucga                                                  19

<210> SEQ ID NO 242
<211> LENGTH: 19
<212> TYPE: RNA
<213> ORGANISM: Homo sapiens

<400> SEQUENCE: 242
caucguugca guugaccau                                                  19

<210> SEQ ID NO 243
<211> LENGTH: 19
<212> TYPE: RNA
<213> ORGANISM: Homo sapiens

<400> SEQUENCE: 243
cugcccaaaa uuccaaggu                                                  19
```

```
<210> SEQ ID NO 244
<211> LENGTH: 19
<212> TYPE: RNA
<213> ORGANISM: Homo sapiens

<400> SEQUENCE: 244
uauguucuug augaacuug                                              19

<210> SEQ ID NO 245
<211> LENGTH: 19
<212> TYPE: RNA
<213> ORGANISM: Homo sapiens

<400> SEQUENCE: 245
aagguauguu cuugaugaa                                              19

<210> SEQ ID NO 246
<211> LENGTH: 19
<212> TYPE: RNA
<213> ORGANISM: Homo sapiens

<400> SEQUENCE: 246
gcccaaaauu ccaagguau                                              19

<210> SEQ ID NO 247
<211> LENGTH: 19
<212> TYPE: RNA
<213> ORGANISM: Homo sapiens

<400> SEQUENCE: 247
aacucauugc ggaaguacu                                              19

<210> SEQ ID NO 248
<211> LENGTH: 19
<212> TYPE: RNA
<213> ORGANISM: Homo sapiens

<400> SEQUENCE: 248
ucauccacga cuccaccca                                              19

<210> SEQ ID NO 249
<211> LENGTH: 19
<212> TYPE: RNA
<213> ORGANISM: Homo sapiens

<400> SEQUENCE: 249
uugcuguucu ggucauggg                                              19

<210> SEQ ID NO 250
<211> LENGTH: 19
<212> TYPE: RNA
<213> ORGANISM: Homo sapiens

<400> SEQUENCE: 250
auguucuuga ugaacuugg                                              19

<210> SEQ ID NO 251
<211> LENGTH: 19
<212> TYPE: RNA
<213> ORGANISM: Homo sapiens

<400> SEQUENCE: 251
ucaggaacuu gggguugac                                              19
```

```
<210> SEQ ID NO 252
<211> LENGTH: 19
<212> TYPE: RNA
<213> ORGANISM: Homo sapiens

<400> SEQUENCE: 252
uccaagguau guucuugau                                                   19

<210> SEQ ID NO 253
<211> LENGTH: 19
<212> TYPE: RNA
<213> ORGANISM: Homo sapiens

<400> SEQUENCE: 253
ucaucguugc aguugacca                                                   19

<210> SEQ ID NO 254
<211> LENGTH: 19
<212> TYPE: RNA
<213> ORGANISM: Homo sapiens

<400> SEQUENCE: 254
aucguugcag uugaccaug                                                   19

<210> SEQ ID NO 255
<211> LENGTH: 19
<212> TYPE: RNA
<213> ORGANISM: Homo sapiens

<400> SEQUENCE: 255
caaacugccc aaaauucca                                                   19

<210> SEQ ID NO 256
<211> LENGTH: 19
<212> TYPE: RNA
<213> ORGANISM: Homo sapiens

<400> SEQUENCE: 256
cccuggucau cguugcagu                                                   19

<210> SEQ ID NO 257
<211> LENGTH: 19
<212> TYPE: RNA
<213> ORGANISM: Homo sapiens

<400> SEQUENCE: 257
ucaggcagau gucuaggau                                                   19

<210> SEQ ID NO 258
<211> LENGTH: 19
<212> TYPE: RNA
<213> ORGANISM: Homo sapiens

<400> SEQUENCE: 258
cuggucaucg uugcaguug                                                   19

<210> SEQ ID NO 259
<211> LENGTH: 19
<212> TYPE: RNA
<213> ORGANISM: Homo sapiens

<400> SEQUENCE: 259
ucaaacugcc caaaauucc                                                   19
```

```
<210> SEQ ID NO 260
<211> LENGTH: 19
<212> TYPE: RNA
<213> ORGANISM: Homo sapiens

<400> SEQUENCE: 260
cagguacaca gcauccgcu                                                    19

<210> SEQ ID NO 261
<211> LENGTH: 19
<212> TYPE: RNA
<213> ORGANISM: Homo sapiens

<400> SEQUENCE: 261
uguuggugau gugggcaaa                                                    19

<210> SEQ ID NO 262
<211> LENGTH: 19
<212> TYPE: RNA
<213> ORGANISM: Homo sapiens

<400> SEQUENCE: 262
aauuccaagg uauguucuu                                                    19

<210> SEQ ID NO 263
<211> LENGTH: 19
<212> TYPE: RNA
<213> ORGANISM: Homo sapiens

<400> SEQUENCE: 263
aucaggcaga ugucuagga                                                    19

<210> SEQ ID NO 264
<211> LENGTH: 19
<212> TYPE: RNA
<213> ORGANISM: Homo sapiens

<400> SEQUENCE: 264
cucauugcgg aaguacucg                                                    19

<210> SEQ ID NO 265
<211> LENGTH: 19
<212> TYPE: RNA
<213> ORGANISM: Homo sapiens

<400> SEQUENCE: 265
caggaacuug ggguugaca                                                    19

<210> SEQ ID NO 266
<211> LENGTH: 19
<212> TYPE: RNA
<213> ORGANISM: Homo sapiens

<400> SEQUENCE: 266
ugaugugggc aaagacguc                                                    19

<210> SEQ ID NO 267
<211> LENGTH: 19
<212> TYPE: RNA
<213> ORGANISM: Homo sapiens

<400> SEQUENCE: 267
aguccaggua cacagcauc                                                    19
```

<210> SEQ ID NO 268
<211> LENGTH: 19
<212> TYPE: RNA
<213> ORGANISM: Homo sapiens

<400> SEQUENCE: 268
aaauuccaag guauguucu					19

<210> SEQ ID NO 269
<211> LENGTH: 19
<212> TYPE: RNA
<213> ORGANISM: Homo sapiens

<400> SEQUENCE: 269
gugauguggg caaagacgu					19

<210> SEQ ID NO 270
<211> LENGTH: 19
<212> TYPE: RNA
<213> ORGANISM: Homo sapiens

<400> SEQUENCE: 270
cauugcggaa guacucgau					19

<210> SEQ ID NO 271
<211> LENGTH: 19
<212> TYPE: RNA
<213> ORGANISM: Homo sapiens

<400> SEQUENCE: 271
guauguucuu gaugaacuu					19

<210> SEQ ID NO 272
<211> LENGTH: 19
<212> TYPE: RNA
<213> ORGANISM: Homo sapiens

<400> SEQUENCE: 272
cuggucaucc acgacucca					19

<210> SEQ ID NO 273
<211> LENGTH: 19
<212> TYPE: RNA
<213> ORGANISM: Homo sapiens

<400> SEQUENCE: 273
aucaucucgc ucuugucac					19

<210> SEQ ID NO 274
<211> LENGTH: 19
<212> TYPE: RNA
<213> ORGANISM: Homo sapiens

<400> SEQUENCE: 274
uugcggaagu acucgauga					19

<210> SEQ ID NO 275
<211> LENGTH: 19
<212> TYPE: RNA
<213> ORGANISM: Homo sapiens

<400> SEQUENCE: 275
ccuccuugau ggcacgaac					19

<210> SEQ ID NO 276
<211> LENGTH: 19
<212> TYPE: RNA
<213> ORGANISM: Homo sapiens

<400> SEQUENCE: 276
ccaagguaug uucuugaug                                               19

<210> SEQ ID NO 277
<211> LENGTH: 19
<212> TYPE: RNA
<213> ORGANISM: Homo sapiens

<400> SEQUENCE: 277
ugcccaaaau uccaaggua                                               19

<210> SEQ ID NO 278
<211> LENGTH: 19
<212> TYPE: RNA
<213> ORGANISM: Homo sapiens

<400> SEQUENCE: 278
agaucaucuc gcucuuguc                                               19

<210> SEQ ID NO 279
<211> LENGTH: 19
<212> TYPE: RNA
<213> ORGANISM: Homo sapiens

<400> SEQUENCE: 279
ggugaugugg gcaaagacg                                               19

<210> SEQ ID NO 280
<211> LENGTH: 19
<212> TYPE: RNA
<213> ORGANISM: Homo sapiens

<400> SEQUENCE: 280
gaguccaggu acacagcau                                               19

<210> SEQ ID NO 281
<211> LENGTH: 19
<212> TYPE: RNA
<213> ORGANISM: Homo sapiens

<400> SEQUENCE: 281
aaacugccca aaauuccaa                                               19

<210> SEQ ID NO 282
<211> LENGTH: 19
<212> TYPE: RNA
<213> ORGANISM: Homo sapiens

<400> SEQUENCE: 282
uguucuugau gaacuuggc                                               19

<210> SEQ ID NO 283
<211> LENGTH: 19
<212> TYPE: RNA
<213> ORGANISM: Homo sapiens

<400> SEQUENCE: 283
gguauguucu ugaugaacu                                               19

```
<210> SEQ ID NO 284
<211> LENGTH: 19
<212> TYPE: RNA
<213> ORGANISM: Homo sapiens

<400> SEQUENCE: 284
uggugaugug ggcaaagac                                                  19

<210> SEQ ID NO 285
<211> LENGTH: 19
<212> TYPE: RNA
<213> ORGANISM: Homo sapiens

<400> SEQUENCE: 285
ggcagauguc uaggauccc                                                  19

<210> SEQ ID NO 286
<211> LENGTH: 19
<212> TYPE: RNA
<213> ORGANISM: Homo sapiens

<400> SEQUENCE: 286
caggcagaug ucuaggauc                                                  19

<210> SEQ ID NO 287
<211> LENGTH: 19
<212> TYPE: RNA
<213> ORGANISM: Homo sapiens

<400> SEQUENCE: 287
aggaacuugg gguugacau                                                  19

<210> SEQ ID NO 288
<211> LENGTH: 19
<212> TYPE: RNA
<213> ORGANISM: Homo sapiens

<400> SEQUENCE: 288
caagguaugu ucuugauga                                                  19

<210> SEQ ID NO 289
<211> LENGTH: 19
<212> TYPE: RNA
<213> ORGANISM: Homo sapiens

<400> SEQUENCE: 289
uuccaaggua uguucuuga                                                  19

<210> SEQ ID NO 290
<211> LENGTH: 19
<212> TYPE: RNA
<213> ORGANISM: Homo sapiens

<400> SEQUENCE: 290
auugcggaag uacucgaug                                                  19

<210> SEQ ID NO 291
<211> LENGTH: 19
<212> TYPE: RNA
<213> ORGANISM: Homo sapiens

<400> SEQUENCE: 291
guccagguac acagcaucc                                                  19
```

```
<210> SEQ ID NO 292
<211> LENGTH: 19
<212> TYPE: RNA
<213> ORGANISM: Homo sapiens

<400> SEQUENCE: 292
ggaacuuggg guugacauc                                                19

<210> SEQ ID NO 293
<211> LENGTH: 19
<212> TYPE: RNA
<213> ORGANISM: Homo sapiens

<400> SEQUENCE: 293
gguugcuguu cuggucaug                                                19

<210> SEQ ID NO 294
<211> LENGTH: 19
<212> TYPE: RNA
<213> ORGANISM: Homo sapiens

<400> SEQUENCE: 294
ugcuguucug gucaugggc                                                19

<210> SEQ ID NO 295
<211> LENGTH: 19
<212> TYPE: RNA
<213> ORGANISM: Homo sapiens

<400> SEQUENCE: 295
aaaauuccaa gguauguuc                                                19

<210> SEQ ID NO 296
<211> LENGTH: 19
<212> TYPE: RNA
<213> ORGANISM: Homo sapiens

<400> SEQUENCE: 296
uggucaucca cgacuccac                                                19

<210> SEQ ID NO 297
<211> LENGTH: 19
<212> TYPE: RNA
<213> ORGANISM: Homo sapiens

<400> SEQUENCE: 297
uggucaucgu ugcaguuga                                                19

<210> SEQ ID NO 298
<211> LENGTH: 19
<212> TYPE: RNA
<213> ORGANISM: Homo sapiens

<400> SEQUENCE: 298
ucuucaaacu gcccaaaau                                                19

<210> SEQ ID NO 299
<211> LENGTH: 19
<212> TYPE: RNA
<213> ORGANISM: Homo sapiens

<400> SEQUENCE: 299
caaaauucca agguauguu                                                19
```

```
<210> SEQ ID NO 300
<211> LENGTH: 19
<212> TYPE: RNA
<213> ORGANISM: Homo sapiens

<400> SEQUENCE: 300
gaucaucucg cucuuguca                                                       19

<210> SEQ ID NO 301
<211> LENGTH: 19
<212> TYPE: RNA
<213> ORGANISM: Homo sapiens

<400> SEQUENCE: 301
cccuccuuga uggcacgaa                                                       19

<210> SEQ ID NO 302
<211> LENGTH: 19
<212> TYPE: RNA
<213> ORGANISM: Homo sapiens

<400> SEQUENCE: 302
auccaggaca ugggcuga                                                        19

<210> SEQ ID NO 303
<211> LENGTH: 19
<212> TYPE: RNA
<213> ORGANISM: Homo sapiens

<400> SEQUENCE: 303
gucaucguug caguugacc                                                       19

<210> SEQ ID NO 304
<211> LENGTH: 19
<212> TYPE: RNA
<213> ORGANISM: Homo sapiens

<400> SEQUENCE: 304
cuucaaacug cccaaaauu                                                       19

<210> SEQ ID NO 305
<211> LENGTH: 19
<212> TYPE: RNA
<213> ORGANISM: Homo sapiens

<400> SEQUENCE: 305
agguacacag cauccgcug                                                       19

<210> SEQ ID NO 306
<211> LENGTH: 19
<212> TYPE: RNA
<213> ORGANISM: Homo sapiens

<400> SEQUENCE: 306 ccugucauc guugcaguu                                                        19

<210> SEQ ID NO 307
<211> LENGTH: 19
<212> TYPE: RNA
<213> ORGANISM: Homo sapiens

<400> SEQUENCE: 307
agguugcugu ucuggucau                                                       19
```

-continued

<210> SEQ ID NO 308
<211> LENGTH: 19
<212> TYPE: RNA
<213> ORGANISM: Homo sapiens

<400> SEQUENCE: 308
cccaaaauuc caagguaug                                                19

<210> SEQ ID NO 309
<211> LENGTH: 19
<212> TYPE: RNA
<213> ORGANISM: Homo sapiens

<400> SEQUENCE: 309
guuggugaug ugggcaaag                                                19

<210> SEQ ID NO 310
<211> LENGTH: 19
<212> TYPE: RNA
<213> ORGANISM: Homo sapiens

<400> SEQUENCE: 310
acucauugcg gaaguacuc                                                19

<210> SEQ ID NO 311
<211> LENGTH: 19
<212> TYPE: RNA
<213> ORGANISM: Homo sapiens

<400> SEQUENCE: 311
cguugcaguu gaccaugcc                                                19

<210> SEQ ID NO 312
<211> LENGTH: 19
<212> TYPE: RNA
<213> ORGANISM: Homo sapiens

<400> SEQUENCE: 312
uuggugaugu gggcaaaga                                                19

<210> SEQ ID NO 313
<211> LENGTH: 19
<212> TYPE: RNA
<213> ORGANISM: Homo sapiens

<400> SEQUENCE: 313
uucaaacugc ccaaaauuc                                                19

<210> SEQ ID NO 314
<211> LENGTH: 19
<212> TYPE: RNA
<213> ORGANISM: Homo sapiens

<400> SEQUENCE: 314
acugcccaaa auuccaagg                                                19

<210> SEQ ID NO 315
<211> LENGTH: 19
<212> TYPE: RNA
<213> ORGANISM: Homo sapiens

<400> SEQUENCE: 315
agguauguuc uugaugaac                                                19

```
<210> SEQ ID NO 316
<211> LENGTH: 19
<212> TYPE: RNA
<213> ORGANISM: Homo sapiens

<400> SEQUENCE: 316
uccaggcuga ggcgauaca                                                  19

<210> SEQ ID NO 317
<211> LENGTH: 19
<212> TYPE: RNA
<213> ORGANISM: Homo sapiens

<400> SEQUENCE: 317
uugaugaacu uggccgagc                                                  19

<210> SEQ ID NO 318
<211> LENGTH: 19
<212> TYPE: RNA
<213> ORGANISM: Homo sapiens

<400> SEQUENCE: 318
ugaugaacuu ggccgagcc                                                  19

<210> SEQ ID NO 319
<211> LENGTH: 19
<212> TYPE: RNA
<213> ORGANISM: Homo sapiens

<400> SEQUENCE: 319
aguuguuguc ccagcgucc                                                  19

<210> SEQ ID NO 320
<211> LENGTH: 19
<212> TYPE: RNA
<213> ORGANISM: Homo sapiens

<400> SEQUENCE: 320
aucccaucuu caaacugcc                                                  19

<210> SEQ ID NO 321
<211> LENGTH: 19
<212> TYPE: RNA
<213> ORGANISM: Homo sapiens

<400> SEQUENCE: 321
aggaucccau cuucaaacu                                                  19

<210> SEQ ID NO 322
<211> LENGTH: 19
<212> TYPE: RNA
<213> ORGANISM: Homo sapiens

<400> SEQUENCE: 322
ggaucccauc uucaaacug                                                  19

<210> SEQ ID NO 323
<211> LENGTH: 19
<212> TYPE: RNA
<213> ORGANISM: Homo sapiens

<400> SEQUENCE: 323
augaacuugg ccgagcccu                                                  19
```

```
<210> SEQ ID NO 324
<211> LENGTH: 19
<212> TYPE: RNA
<213> ORGANISM: Homo sapiens

<400> SEQUENCE: 324
gaucccaucu ucaaacugc                                                  19

<210> SEQ ID NO 325
<211> LENGTH: 19
<212> TYPE: RNA
<213> ORGANISM: Homo sapiens

<400> SEQUENCE: 325
cuucaggaac uuggguug                                                   19

<210> SEQ ID NO 326
<211> LENGTH: 19
<212> TYPE: RNA
<213> ORGANISM: Homo sapiens

<400> SEQUENCE: 326
ucccaucuuc aaacugccc                                                  19

<210> SEQ ID NO 327
<211> LENGTH: 19
<212> TYPE: RNA
<213> ORGANISM: Homo sapiens

<400> SEQUENCE: 327
guaguuguug ucccagcgu                                                  19

<210> SEQ ID NO 328
<211> LENGTH: 19
<212> TYPE: RNA
<213> ORGANISM: Homo sapiens

<400> SEQUENCE: 328
gaacugggcc acagcagua                                                  19

<210> SEQ ID NO 329
<211> LENGTH: 19
<212> TYPE: RNA
<213> ORGANISM: Homo sapiens

<400> SEQUENCE: 329
uuguugguga ugugggcaa                                                  19

<210> SEQ ID NO 330
<211> LENGTH: 19
<212> TYPE: RNA
<213> ORGANISM: Homo sapiens

<400> SEQUENCE: 330
agguugagca gguacuugg                                                  19

<210> SEQ ID NO 331
<211> LENGTH: 19
<212> TYPE: RNA
<213> ORGANISM: Homo sapiens

<400> SEQUENCE: 331
uucuugauga acuuggccg                                                  19
```

```
<210> SEQ ID NO 332
<211> LENGTH: 19
<212> TYPE: RNA
<213> ORGANISM: Homo sapiens

<400> SEQUENCE: 332
uuugugcaca gacccaucg                                                19

<210> SEQ ID NO 333
<211> LENGTH: 19
<212> TYPE: RNA
<213> ORGANISM: Homo sapiens

<400> SEQUENCE: 333
aaagacguca aagucacug                                                19

<210> SEQ ID NO 334
<211> LENGTH: 19
<212> TYPE: RNA
<213> ORGANISM: Homo sapiens

<400> SEQUENCE: 334
ucacugccca uguucaugc                                                19

<210> SEQ ID NO 335
<211> LENGTH: 19
<212> TYPE: RNA
<213> ORGANISM: Homo sapiens

<400> SEQUENCE: 335
uacacuggcc ucguaguug                                                19

<210> SEQ ID NO 336
<211> LENGTH: 19
<212> TYPE: RNA
<213> ORGANISM: Homo sapiens

<400> SEQUENCE: 336
gucaaaguca cugcccaug                                                19

<210> SEQ ID NO 337
<211> LENGTH: 19
<212> TYPE: RNA
<213> ORGANISM: Homo sapiens

<400> SEQUENCE: 337
uguuguuggu gaugugggc                                                19

<210> SEQ ID NO 338
<211> LENGTH: 19
<212> TYPE: RNA
<213> ORGANISM: Homo sapiens

<400> SEQUENCE: 338
aguuuguuca ggugguucg                                                19

<210> SEQ ID NO 339
<211> LENGTH: 19
<212> TYPE: RNA
<213> ORGANISM: Homo sapiens

<400> SEQUENCE: 339
ucuuagugga aaacgggcc                                                19
```

```
<210> SEQ ID NO 340
<211> LENGTH: 19
<212> TYPE: RNA
<213> ORGANISM: Homo sapiens

<400> SEQUENCE: 340 gauguggca aagacguca                                                   19

<210> SEQ ID NO 341
<211> LENGTH: 19
<212> TYPE: RNA
<213> ORGANISM: Homo sapiens

<400> SEQUENCE: 341
aaagucacug cccauguuc                                                  19

<210> SEQ ID NO 342
<211> LENGTH: 19
<212> TYPE: RNA
<213> ORGANISM: Homo sapiens

<400> SEQUENCE: 342
aagacgucaa agucacugc                                                  19

<210> SEQ ID NO 343
<211> LENGTH: 19
<212> TYPE: RNA
<213> ORGANISM: Homo sapiens

<400> SEQUENCE: 343
aaaugcucca ggaacacag                                                  19

<210> SEQ ID NO 344
<211> LENGTH: 19
<212> TYPE: RNA
<213> ORGANISM: Homo sapiens

<400> SEQUENCE: 344
agagaaaggc uccagguug                                                  19

<210> SEQ ID NO 345
<211> LENGTH: 21
<212> TYPE: RNA
<213> ORGANISM: Homo sapiens

<400> SEQUENCE: 345
cuagacaucu gccugauccu u                                               21

<210> SEQ ID NO 346
<211> LENGTH: 21
<212> TYPE: RNA
<213> ORGANISM: Homo sapiens

<400> SEQUENCE: 346
caacugacaa caugcuaggu a                                               21

<210> SEQ ID NO 347
<211> LENGTH: 21
<212> TYPE: RNA
<213> ORGANISM: Homo sapiens

<400> SEQUENCE: 347
ccaaguucau caagaacaua c                                               21
```

```
<210> SEQ ID NO 348
<211> LENGTH: 21
<212> TYPE: RNA
<213> ORGANISM: Homo sapiens

<400> SEQUENCE: 348
ccugauccuu cuagauguca a                                              21

<210> SEQ ID NO 349
<211> LENGTH: 21
<212> TYPE: RNA
<213> ORGANISM: Homo sapiens

<400> SEQUENCE: 349
acaagagcga gaugaucugg a                                              21

<210> SEQ ID NO 350
<211> LENGTH: 21
<212> TYPE: RNA
<213> ORGANISM: Homo sapiens

<400> SEQUENCE: 350
caagaacaua ccuuggaauu u                                              21

<210> SEQ ID NO 351
<211> LENGTH: 21
<212> TYPE: RNA
<213> ORGANISM: Homo sapiens

<400> SEQUENCE: 351
cggccaaguu caucaagaac a                                              21

<210> SEQ ID NO 352
<211> LENGTH: 21
<212> TYPE: RNA
<213> ORGANISM: Homo sapiens

<400> SEQUENCE: 352
cuguguuccu ggagcauuug u                                              21

<210> SEQ ID NO 353
<211> LENGTH: 21
<212> TYPE: RNA
<213> ORGANISM: Homo sapiens

<400> SEQUENCE: 353
caagagcgag augaucugga a                                              21

<210> SEQ ID NO 354
<211> LENGTH: 21
<212> TYPE: RNA
<213> ORGANISM: Homo sapiens

<400> SEQUENCE: 354
caacuacgag gccaguguag a                                              21

<210> SEQ ID NO 355
<211> LENGTH: 21
<212> TYPE: RNA
<213> ORGANISM: Homo sapiens

<400> SEQUENCE: 355
ggcccguuuu ccacuaagag a                                              21
```

-continued

<210> SEQ ID NO 356
<211> LENGTH: 21
<212> TYPE: RNA
<213> ORGANISM: Homo sapiens

<400> SEQUENCE: 356
gcaaccuucu caucgaguac u                                              21

<210> SEQ ID NO 357
<211> LENGTH: 21
<212> TYPE: RNA
<213> ORGANISM: Homo sapiens

<400> SEQUENCE: 357
cgagaugauc uggaacuucc a                                              21

<210> SEQ ID NO 358
<211> LENGTH: 21
<212> TYPE: RNA
<213> ORGANISM: Homo sapiens

<400> SEQUENCE: 358
acuuccacug cuggguggag u                                              21

<210> SEQ ID NO 359
<211> LENGTH: 21
<212> TYPE: RNA
<213> ORGANISM: Homo sapiens

<400> SEQUENCE: 359
aaccccaagu uccugaagaa c                                              21

<210> SEQ ID NO 360
<211> LENGTH: 21
<212> TYPE: RNA
<213> ORGANISM: Homo sapiens

<400> SEQUENCE: 360
augaucugga acuuccacug c                                              21

<210> SEQ ID NO 361
<211> LENGTH: 21
<212> TYPE: RNA
<213> ORGANISM: Homo sapiens

<400> SEQUENCE: 361
gaacuuccac ugcugggugg a                                              21

<210> SEQ ID NO 362
<211> LENGTH: 21
<212> TYPE: RNA
<213> ORGANISM: Homo sapiens

<400> SEQUENCE: 362
uggaacuucc acugcugggu g                                              21

<210> SEQ ID NO 363
<211> LENGTH: 21
<212> TYPE: RNA
<213> ORGANISM: Homo sapiens

<400> SEQUENCE: 363
agcgagauga ucuggaacuu c                                              21

```
<210> SEQ ID NO 364
<211> LENGTH: 21
<212> TYPE: RNA
<213> ORGANISM: Homo sapiens

<400> SEQUENCE: 364
gaugaucugg aacuuccacu g                                              21

<210> SEQ ID NO 365
<211> LENGTH: 21
<212> TYPE: RNA
<213> ORGANISM: Homo sapiens

<400> SEQUENCE: 365
agagcgagau gaucuggaac u                                              21

<210> SEQ ID NO 366
<211> LENGTH: 21
<212> TYPE: RNA
<213> ORGANISM: Homo sapiens

<400> SEQUENCE: 366
cuggaacuuc cacugcuggg u                                              21

<210> SEQ ID NO 367
<211> LENGTH: 21
<212> TYPE: RNA
<213> ORGANISM: Homo sapiens

<400> SEQUENCE: 367
ugaucuggaa cuuccacugc u                                              21

<210> SEQ ID NO 368
<211> LENGTH: 21
<212> TYPE: RNA
<213> ORGANISM: Homo sapiens

<400> SEQUENCE: 368
aagagcgaga ugaucuggaa c                                              21

<210> SEQ ID NO 369
<211> LENGTH: 21
<212> TYPE: RNA
<213> ORGANISM: Homo sapiens

<400> SEQUENCE: 369
cagcuuugug cugggccacu u                                              21

<210> SEQ ID NO 370
<211> LENGTH: 21
<212> TYPE: RNA
<213> ORGANISM: Homo sapiens

<400> SEQUENCE: 370
gcuuugugcu gggccacuuc a                                              21

<210> SEQ ID NO 371
<211> LENGTH: 21
<212> TYPE: RNA
<213> ORGANISM: Homo sapiens

<400> SEQUENCE: 371
agaugaucug gaacuuccac u                                              21
```

-continued

```
<210> SEQ ID NO 372
<211> LENGTH: 21
<212> TYPE: RNA
<213> ORGANISM: Homo sapiens

<400> SEQUENCE: 372
cuuugugcug ggccacuuca u                                              21

<210> SEQ ID NO 373
<211> LENGTH: 21
<212> TYPE: RNA
<213> ORGANISM: Homo sapiens

<400> SEQUENCE: 373
gcgagaugau cuggaacuuc c                                              21

<210> SEQ ID NO 374
<211> LENGTH: 21
<212> TYPE: RNA
<213> ORGANISM: Homo sapiens

<400> SEQUENCE: 374
aucuggaacu uccacugcug g                                              21

<210> SEQ ID NO 375
<211> LENGTH: 21
<212> TYPE: RNA
<213> ORGANISM: Homo sapiens

<400> SEQUENCE: 375
ucuggaacuu ccacugcugg g                                              21

<210> SEQ ID NO 376
<211> LENGTH: 21
<212> TYPE: RNA
<213> ORGANISM: Homo sapiens

<400> SEQUENCE: 376
gaucuggaac uuccacugcu g                                              21

<210> SEQ ID NO 377
<211> LENGTH: 21
<212> TYPE: RNA
<213> ORGANISM: Homo sapiens

<400> SEQUENCE: 377
gagaugaucu ggaacuucca c                                              21

<210> SEQ ID NO 378
<211> LENGTH: 21
<212> TYPE: RNA
<213> ORGANISM: Homo sapiens

<400> SEQUENCE: 378
agcuuugugc ugggccacuu c                                              21

<210> SEQ ID NO 379
<211> LENGTH: 21
<212> TYPE: RNA
<213> ORGANISM: Homo sapiens

<400> SEQUENCE: 379
gagcgagaug aucuggaacu u                                              21
```

```
<210> SEQ ID NO 380
<211> LENGTH: 21
<212> TYPE: RNA
<213> ORGANISM: Homo sapiens

<400> SEQUENCE: 380
aacuuccacu gcugggugga g                                              21

<210> SEQ ID NO 381
<211> LENGTH: 21
<212> TYPE: RNA
<213> ORGANISM: Homo sapiens

<400> SEQUENCE: 381
aaggaucagg cagaugucua g                                              21

<210> SEQ ID NO 382
<211> LENGTH: 21
<212> TYPE: RNA
<213> ORGANISM: Homo sapiens

<400> SEQUENCE: 382
uaccuagcau guugucaguu g                                              21

<210> SEQ ID NO 383
<211> LENGTH: 21
<212> TYPE: RNA
<213> ORGANISM: Homo sapiens

<400> SEQUENCE: 383
guauguucuu gaugaacuug g                                              21

<210> SEQ ID NO 384
<211> LENGTH: 21
<212> TYPE: RNA
<213> ORGANISM: Homo sapiens

<400> SEQUENCE: 384
uugacaucua gaaggaucag g                                              21

<210> SEQ ID NO 385
<211> LENGTH: 21
<212> TYPE: RNA
<213> ORGANISM: Homo sapiens

<400> SEQUENCE: 385
uccagaucau cucgcucuug u                                              21

<210> SEQ ID NO 386
<211> LENGTH: 21
<212> TYPE: RNA
<213> ORGANISM: Homo sapiens

<400> SEQUENCE: 386
aaauuccaag guauguucuu g                                              21

<210> SEQ ID NO 387
<211> LENGTH: 21
<212> TYPE: RNA
<213> ORGANISM: Homo sapiens

<400> SEQUENCE: 387
uguucuugau gaacuuggcc g                                              21
```

```
<210> SEQ ID NO 388
<211> LENGTH: 21
<212> TYPE: RNA
<213> ORGANISM: Homo sapiens

<400> SEQUENCE: 388
acaaaugcuc caggaacaca g                                              21

<210> SEQ ID NO 389
<211> LENGTH: 21
<212> TYPE: RNA
<213> ORGANISM: Homo sapiens

<400> SEQUENCE: 389
uuccagauca ucucgcucuu g                                              21

<210> SEQ ID NO 390
<211> LENGTH: 21
<212> TYPE: RNA
<213> ORGANISM: Homo sapiens

<400> SEQUENCE: 390
ucuacacugg ccucguaguu g                                              21

<210> SEQ ID NO 391
<211> LENGTH: 21
<212> TYPE: RNA
<213> ORGANISM: Homo sapiens

<400> SEQUENCE: 391
ucucuuagug gaaaacgggc c                                              21

<210> SEQ ID NO 392
<211> LENGTH: 21
<212> TYPE: RNA
<213> ORGANISM: Homo sapiens

<400> SEQUENCE: 392
aguacucgau gagaagguug c                                              21

<210> SEQ ID NO 393
<211> LENGTH: 21
<212> TYPE: RNA
<213> ORGANISM: Homo sapiens

<400> SEQUENCE: 393
uggaaguucc agaucaucuc g                                              21

<210> SEQ ID NO 394
<211> LENGTH: 21
<212> TYPE: RNA
<213> ORGANISM: Homo sapiens

<400> SEQUENCE: 394
acuccaccca gcaguggaag u                                              21

<210> SEQ ID NO 395
<211> LENGTH: 21
<212> TYPE: RNA
<213> ORGANISM: Homo sapiens

<400> SEQUENCE: 395
guucuucagg aacuuggggu u                                              21
```

```
<210> SEQ ID NO 396
<211> LENGTH: 21
<212> TYPE: RNA
<213> ORGANISM: Homo sapiens

<400> SEQUENCE: 396
gcaguggaag uuccagauca u                                              21

<210> SEQ ID NO 397
<211> LENGTH: 21
<212> TYPE: RNA
<213> ORGANISM: Homo sapiens

<400> SEQUENCE: 397
uccacccagc aguggaaguu c                                              21

<210> SEQ ID NO 398
<211> LENGTH: 21
<212> TYPE: RNA
<213> ORGANISM: Homo sapiens

<400> SEQUENCE: 398
cacccagcag uggaaguucc a                                              21

<210> SEQ ID NO 399
<211> LENGTH: 21
<212> TYPE: RNA
<213> ORGANISM: Homo sapiens

<400> SEQUENCE: 399
gaaguuccag aucaucucgc u                                              21

<210> SEQ ID NO 400
<211> LENGTH: 21
<212> TYPE: RNA
<213> ORGANISM: Homo sapiens

<400> SEQUENCE: 400
caguggaagu uccagaucau c                                              21

<210> SEQ ID NO 401
<211> LENGTH: 21
<212> TYPE: RNA
<213> ORGANISM: Homo sapiens

<400> SEQUENCE: 401
aguuccagau caucucgcuc u                                              21

<210> SEQ ID NO 402
<211> LENGTH: 21
<212> TYPE: RNA
<213> ORGANISM: Homo sapiens

<400> SEQUENCE: 402
acccagcagu ggaaguucca g                                              21

<210> SEQ ID NO 403
<211> LENGTH: 21
<212> TYPE: RNA
<213> ORGANISM: Homo sapiens

<400> SEQUENCE: 403
agcaguggaa guuccagauc a                                              21
```

```
<210> SEQ ID NO 404
<211> LENGTH: 21
<212> TYPE: RNA
<213> ORGANISM: Homo sapiens

<400> SEQUENCE: 404
guuccagauc aucucgcucu u                                              21

<210> SEQ ID NO 405
<211> LENGTH: 21
<212> TYPE: RNA
<213> ORGANISM: Homo sapiens

<400> SEQUENCE: 405
aaguggccca gcacaaagcu g                                              21

<210> SEQ ID NO 406
<211> LENGTH: 21
<212> TYPE: RNA
<213> ORGANISM: Homo sapiens

<400> SEQUENCE: 406
ugaaguggcc cagcacaaag c                                              21

<210> SEQ ID NO 407
<211> LENGTH: 21
<212> TYPE: RNA
<213> ORGANISM: Homo sapiens

<400> SEQUENCE: 407
aguggaaguu ccagaucauc u                                              21

<210> SEQ ID NO 408
<211> LENGTH: 21
<212> TYPE: RNA
<213> ORGANISM: Homo sapiens

<400> SEQUENCE: 408
augaaguggc ccagcacaaa g                                              21

<210> SEQ ID NO 409
<211> LENGTH: 21
<212> TYPE: RNA
<213> ORGANISM: Homo sapiens

<400> SEQUENCE: 409
ggaaguucca gaucaucucg c                                              21

<210> SEQ ID NO 410
<211> LENGTH: 21
<212> TYPE: RNA
<213> ORGANISM: Homo sapiens

<400> SEQUENCE: 410
ccagcagugg aaguuccaga u                                              21

<210> SEQ ID NO 411
<211> LENGTH: 21
<212> TYPE: RNA
<213> ORGANISM: Homo sapiens

<400> SEQUENCE: 411
cccagcagug gaaguuccag a                                              21
```

```
<210> SEQ ID NO 412
<211> LENGTH: 21
<212> TYPE: RNA
<213> ORGANISM: Homo sapiens

<400> SEQUENCE: 412
cagcagugga aguuccagau c                                              21

<210> SEQ ID NO 413
<211> LENGTH: 21
<212> TYPE: RNA
<213> ORGANISM: Homo sapiens

<400> SEQUENCE: 413
guggaaguuc cagaucaucu c                                              21

<210> SEQ ID NO 414
<211> LENGTH: 21
<212> TYPE: RNA
<213> ORGANISM: Homo sapiens

<400> SEQUENCE: 414
gaaguggccc agcacaaagc u                                              21

<210> SEQ ID NO 415
<211> LENGTH: 21
<212> TYPE: RNA
<213> ORGANISM: Homo sapiens

<400> SEQUENCE: 415
aaguuccaga ucaucucgcu c                                              21

<210> SEQ ID NO 416
<211> LENGTH: 21
<212> TYPE: RNA
<213> ORGANISM: Homo sapiens

<400> SEQUENCE: 416
cuccacccag caguggaagu u                                              21
```